(12) United States Patent
Stock et al.

(10) Patent No.: US 10,117,904 B2
(45) Date of Patent: *Nov. 6, 2018

(54) USE OF ANTI-BACTERIAL AGENTS FOR THE TREATMENT OF EPITHELIAL-RELATED CONDITIONS

(71) Applicant: Signum Biosciences, Inc., Princeton, NJ (US)

(72) Inventors: Jeffry B. Stock, Princeton, NJ (US); Maxwell Stock, Princeton, NJ (US)

(73) Assignee: Signum Biosciences, Inc., Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/221,380

(22) Filed: Jul. 27, 2016

(65) Prior Publication Data

US 2017/0049841 A1    Feb. 23, 2017

Related U.S. Application Data

(63) Continuation of application No. 12/945,813, filed on Nov. 12, 2010, now Pat. No. 9,415,026.

(60) Provisional application No. 61/260,401, filed on Nov. 12, 2009.

(51) Int. Cl.
| | | |
|---|---|---|
| *A61K 38/05* | (2006.01) | |
| *A61K 31/198* | (2006.01) | |
| *A61K 31/341* | (2006.01) | |
| *A61K 31/381* | (2006.01) | |
| *A61K 31/4045* | (2006.01) | |
| *A61K 31/5375* | (2006.01) | |
| *A61K 9/00* | (2006.01) | |
| *A61K 31/165* | (2006.01) | |

(52) U.S. Cl.
CPC ............ *A61K 38/05* (2013.01); *A61K 9/007* (2013.01); *A61K 9/0014* (2013.01); *A61K 31/165* (2013.01); *A61K 31/198* (2013.01); *A61K 31/341* (2013.01); *A61K 31/381* (2013.01); *A61K 31/4045* (2013.01); *A61K 31/5375* (2013.01)

(58) Field of Classification Search
CPC .. A61K 31/165; A61K 31/198; A61K 31/341; A61K 31/381; A61K 31/4045; A61K 31/5375; A61K 38/05; A61K 9/0014; A61K 9/007
See application file for complete search history.

(56) References Cited

U.S. PATENT DOCUMENTS

| | | |
|---|---|---|
| 2005/0277694 A1 | 12/2005 | Stock et al. |
| 2006/0128623 A1 | 6/2006 | Modlin et al. |
| 2006/0287232 A1 | 12/2006 | Clayberger et al. |
| 2010/0184768 A1 | 7/2010 | Stock et al. |
| 2010/0247461 A1 | 9/2010 | Voronkov et al. |
| 2011/0217249 A1 | 9/2011 | Dreher |

FOREIGN PATENT DOCUMENTS

| | | |
|---|---|---|
| WO | 2005/123103 | 12/2005 |
| WO | 2009/102997 | 8/2009 |
| WO | 2010/056778 | 5/2010 |
| WO | 2010/090845 | 8/2010 |

OTHER PUBLICATIONS

Jappe et al. (British J of Dermatology, 2002, 146, 202-209).*
Ding J et al, "Farnesyl-L-Cysteine Analogs Can Inhibit or Initiate Superoxide Release by Human Neutrophils", Journal of Biological Chemistry, American Society for Biochemistry and Molecular Biology, US, vol. 269, No. 24, Jun. 17, 1994, pp. 16837-16844.
Gordon Joel S. et al., "Topical N-acetyl-S-farnesyl-L-cysteine Inhibits Mouse Skin Inflammation, and Unlike Dexamethasone, its Effects Are Restricted to the Application site", Journal of Investigative Dermatology, Nature Publishing Group, GB, vol. 128, No. 3, Jan. 1, 2008, pp. 643-654.

* cited by examiner

*Primary Examiner* — Umamaheswari Ramachandran
(74) *Attorney, Agent, or Firm* — McCarter & English, LLP; Peter Tu; Maneesh Gulati

(57) ABSTRACT

Disclosed herein are methods of inactivating and/or decolonizing bacteria on a surface. The present invention also discloses methods for treatment of epithelial conditions caused or aggravated by bacteria, such as acne vulgaris, in a subject in need thereof. The present invention additionally discloses inventive compounds and compositions that exhibit anti-bacterial and/or anti-inflammatory effects.

17 Claims, 16 Drawing Sheets

| Compound | IC 50 (µg/mL) |
|---|---|
| BPO | 1 |
| Deoxycycline | 3 |
| AFC | 3 |
| Compound A | 1 |
| Compound B | 1 |
| Compound C | 3 |
| Compound D | 1 |
| Compound E | 3 |
| Compound F | 3 |
| Compound G | 3 |
| Compound H | 3 |
| Compound I | 2 |
| Compound J | 3 |
| Compound K | 3 |
| Compound L | 3 |

IC50 Range 1 is >100 µg/mL
IC50 Range 2 is 20-100 µg/mL
IC50 Range 3 is <20 µg/mL

Figure 1

| COMPOUND | ACTIVITY RANGE |
|---|---|
| Dexamethasone | 1 |
| Clobetasol | 1 |
| Salicylic Acid | 2 |
| AFC | 1 |
| Compound A | 1 |
| Compound D | 1 |
| Compound F | 1 |
| Compound G | 2 |
| Compound I | 1 |
| Compound B | 2 |
| Compound J | 2 |
| Compound K | 1 |
| Compound L | 2 |

Activity Range 1 is >40% (Active anti-acne)
Activity Range 2 is 30-40% (Moderately active anti-acne)
*Activity is Percent Inhibition in MPO Assay

Figure 4

| COMPOUND | ACTIVITY RANGE |
|---|---|
| Dexamethasone | 1 |
| Clobetasol | 1 |
| Salicylic Acid | 2 |
| AFC | 1 |
| Compound A | 1 |
| Compound D | 1 |
| Compound F | 1 |
| Compound G | 1 |
| Compound I | 2 |
| Compound B | 2 |
| Compound J | 1 |
| Compound K | 1 |
| Compound L | 1 |

Activity Range 1 is >30% (Active anti-acne)
Activity Range 2 is 20-30% (Moderately active anti-acne)
*Activity is Percent Inhibition of IL-6 levels.

Figure 5

| COMPOUND | ACTIVITY RANGE |
|---|---|
| Dexamethasone | 2 |
| Clobetasol | 1 |
| AFC | 1 |
| Compound A | 1 |
| Compound F | 2 |
| Compound G | 2 |
| Compound B | 2 |
| Compound J | 1 |
| Compound K | 1 |
| Compound L | 1 |

Activity Range 1 is >60% (Active anti-acne)
Activity Range 2 is 40-60% (Moderately active anti-acne)
*Activity is Percent Inhibition of TNF-α levels.

Figure 6

| COMPOUND | ACTIVITY RANGE |
|---|---|
| Dexamethasone | 1 |
| Clobetasol | 1 |
| Salicylic Acid | 2 |
| AFC | 1 |
| Compound A | 1 |
| Compound D | 2 |
| Compound F | 2 |
| Compound G | 2 |
| Compound I | 2 |
| Compound B | 2 |
| Compound J | 1 |
| Compound K | 1 |
| Compound L | 1 |

Activity Range 1 is >30% (Active anti-acne)
Activity Range 2 is 0-30% (Moderately active anti-acne)
*Activity is Percent Inhibition of IL-8 levels.

Figure 7

| COMPOUND | ACTIVITY RANGE |
|---|---|
| Dexamethasone | 1 |
| Clobetasol | 1 |
| Salicylic Acid | 2 |
| AFC | 1 |
| Compound A | 1 |
| Compound D | 1 |
| Compound F | 1 |
| Compound G | 1 |
| Compound I | 2 |

Activity Range 1 is >40% (Active anti-acne)
Activity Range 2 is 0-40% (Moderately active anti-acne)
*Activity is Percent Inhibition of IL-1β levels.

Figure 8

USE OF ANTI-BACTERIAL AGENTS FOR THE TREATMENT OF EPITHELIAL-RELATED CONDITIONS

CROSS-REFERENCE TO RELATED APPLICATIONS

This application claims priority to U.S. provisional application Ser. No. 61/260,401, filed Nov. 12, 2009, the entirety of which is hereby incorporated herein by reference.

BACKGROUND

Difficulties associated with the treatment of conditions related to bacterial colonization of mammalian epithelium are well-appreciated amongst dermatologists. This is particularly true in the case of skin and wound antisepsis, where the most effective treatment of epithelial conditions caused or aggravated by bacterial colonization, often includes the use of a topical anti-bacterial agent. However, the emergence of bacterial resistance to commonly-used antibiotics has posed an ever-increasing challenge in the treatment, prevention and containment of epithelial-related conditions, caused or aggravated by bacteria. There is a clear and urgent need for innovative and cost-effective methods for an efficacious treatment, prevention and/or management of such conditions.

Other background and methods may be found in U.S. Pat. Nos. 5,043,268, 5,202,456, 5,705,528; United States Patent Publications: 2005/0277694, 2007/0004803, 2009/0155186, 2009/0170917; U.S. patent application Ser. No. 12/867,796 (based on World Publication WO 2009/102997), and United States Patent Publication No. 2010/0184768, each of which is hereby incorporated by reference in its entirety.

SUMMARY

The present invention encompasses the recognition that there exists a need for new compounds, compositions, and methods for treating, preventing, and/or managing bacterial-associated conditions.

The present invention, provides, inter alia, methods to kill, inactivate, decolonize and/or inhibit the growth of bacteria on a surface.

In some embodiments, the present invention provides methods to treat, prevent or ameliorate the symptoms of epithelial-related conditions, caused or aggravated by bacteria in a subject in need thereof.

In some embodiments, the present invention provides methods to treat, prevent and/or ameliorate symptoms of inflammation associated with epithelial-related conditions, caused or aggravated by bacteria.

In some embodiments, epithelial-related conditions include skin conditions. In some embodiments, epithelial-related conditions include respiratory conditions. In some embodiments, epithelial-related conditions include nasal conditions. In some embodiments, epithelial-related conditions include ocular conditions. In some embodiments, epithelial-related conditions include oral conditions. In some embodiments, epithelial-related conditions include conditions of the external ear. In some embodiments, epithelial-related conditions include vaginal conditions. In some embodiments, epithelial-related conditions include genitourinary conditions. In some embodiments, epithelial-related conditions include rectal conditions.

In some embodiments, skin conditions include impetigo; acne vulgaris; eczema; atopic dermatitis; infective dermatitis; psoriasis; rosacea; erythema; necrotizing cellulitis; cutaneous anthrax; cellulitis; erysipelas; ecthyma; cutaneous anthrax; necroticizing fasciitis; gangrene; septicaemia; pyoderma; endocarditis; toe web infections; sycosis barbae; furuncles and carbuncles; Staphylococcal scalded skin syndrome; blistering distal dactylitis; acute paronychia; folliculitis; cutaneous diphtheria; erythrasma; bacterial colonization of open wounds (e.g., cuts, lesions, scrapes, burns, lacerations, chronic wounds, infected animal bites, ulcerations, etc.).

In some embodiments, respiratory conditions include pneumonia; hypersensitivity pneumonitis; upper and lower respiratory tract infections (e.g., secondary bacterial infections in chronic bronchitis and asma; chronic obstructive pulmonary disease); diphtheria; bronchopulmonary dysplasia; pertussis; legionellosis (e.g., Legionnaires' disease, Pontiac fever; pharyngitis, etc.).

In some embodiments, nasal conditions include bacterial rhinitis; paranasal sinusitis, etc.

In some embodiments, ocular conditions include chronic blepharitis; endophthalmitis, etc.

In some embodiments, oral conditions include gingivitis; dental caries; early childhood caries, etc.

In some embodiments, conditions of the external ear include otitis media, etc.

In some embodiments, vaginal conditions include bacterial vaginosis; chanchroid; syphilis; donovanosis; gonorrhea; lymphogranuloma venereum; non-gonococcal urethritis; staphylococcal infection; vulvovaginitis, etc.

In some embodiments, genitourinary conditions include for example, *Granuloma* inquinale, perianal infections, etc.

In some embodiments, bacteria is *Propionibacterium acnes*.

In some embodiments, epithelial-related conditions may be associated with clinical indications (e.g., infection).

In some embodiments, epithelial-related conditions may not be associated with clinical indications (e.g., infection).

In some embodiments, epithelial-related conditions are associated with clinical indications (e.g., infection).

In some embodiments, methods of the present invention are useful in treating epithelial-related conditions in animals, including humans in need of treatment thereof.

In some embodiments, methods of the present invention are useful in treating epithelial-related conditions in animals, including veterinary animals in need of treatment thereof.

In some embodiments, methods described herein comprise a step of administering to an animal, including a human, in need thereof, an effective amount of a compound of formulae I, Ia, Ib, Ic, Id, Ie, If and/or II and/or in described classes and subclasses thereof.

In some embodiments, provided herein, is a method for disinfection of a surface such as skin or surface of a medical device, etc.

In some embodiments, the present invention also provides a compound of formula I:

$$\underset{R^3}{\overset{Z\diagdown R^2}{\bigvee}}R^1 \quad \text{I}$$

wherein Z, $R^1$, $R^2$, and $R^3$ are defined herein.

In some embodiments, the present invention also provides a compound of formula II:

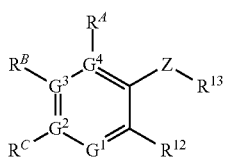

II wherein, Z, $G^{1-4}$, $R^{12}$, $R^{13}$, $R^A$, $R^B$, and $R^C$ are as defined herein.

In some embodiments, described isoprenyl compounds exhibit anti-inflammatory activity. In certain embodiments, described isoprenyl compounds are considered to be anti-inflammatory agents. In some embodiments, described isoprenyl compounds exhibit anti-bacterial activity. In certain embodiments, described isoprenyl compounds are considered to be anti-bacterial agents. In some embodiments, described isoprenyl compounds exhibit both anti-inflammatory as well as anti-bacterial activity.

In some embodiments, described isoprenyl compounds exhibit an anti-acne effect and are useful in the treatment, prevention or amelioration of symptoms associated with inflamed acne vulgaris. In some embodiments, the present invention provides methods to treat, prevent and/or ameliorate the symptoms of acne vulgaris caused or aggravated by *P. acnes*. In some embodiments, described isoprenyl compounds are considered to exhibit anti-acne activity. In certain embodiments, described isoprenyl compounds are considered to be anti-acne agents.

In some embodiments, the invention provides a pharmaceutical composition useful in accordance with the present invention, wherein the composition comprises one or more described isoprenyl compounds of any of formulae I, Ia, Ib, Ic, Id, Ie, If and/or II as described and defined in classes and subclasses herein, and a pharmaceutically acceptable carrier.

In some embodiments, the invention provides a cosmetic composition useful in accordance to the present invention, wherein the composition comprises a compound of any of formulae I, Ia, Ib, Ic, Id, Ie, If and/or II as described and defined in classes and subclasses herein, and a cosmeceutically acceptable carrier.

In some embodiments, the invention provides a topical composition useful in accordance with the present invention, wherein the composition comprises a described isoprenyl compound of any of formulae I, Ia, Ib, Ic, Id, Ie, If and/or II as described and defined in classes and subclasses herein, and a carrier.

In some embodiments, described isoprenyl compounds exhibit antiseptic property. In some embodiments, described isoprenyl compounds may be useful as antiseptic agents.

In some embodiments, described isoprenyl compounds and compositions thereof are useful for disinfection, for example disinfectant compositions. In some embodiments, described isoprenyl compounds may be useful as disinfectant agents.

In some embodiments, described isoprenyl compounds and compositions thereof may be suitable for use on surfaces (e.g., epithelial surfaces; medical devices, etc.).

In some embodiments, described isoprenyl compounds and compositions thereof may be suitable for use on epithelial surfaces (e.g.; skin; mucous membranes, etc.).

In some embodiments, described isoprenyl compounds and compositions thereof may be suitable for use on mucous membranes of (e.g. respiratory tract; nasal cavity; ocular; mouth; vaginal; genitourinary, etc.).

In some embodiments, described isoprenyl compounds kill bacteria. In some embodiments, described isoprenyl compounds inactivate bacteria. In some embodiments, described isoprenyl compounds inhibit growth of bacteria. In some embodiments, described isoprenyl compounds decolonize bacteria. In some embodiments, described isoprenyl compounds decolonize bacteria in biofilms on a surface. In some embodiments, described isoprenyl compounds prevent formation of biofilms on a surface.

Definitions

"N-acetyl-farnesyl-S-cysteine compound" or a "AFC compound" or a "described AFC compound" or a "isoprenyl compound" or a "described isoprenyl compound": As used herein, an "N-acetyl-farnesyl-S-cysteine compound" (or an "AFC compound" or "a described AFC compound" or an "isoprenyl compound" or a "described isoprenyl compound"), is a small molecule compound that is structurally related to N-acetyl-farnesyl-S-cysteine (AFC). For example, in some embodiments, a described isoprenyl compound has the structure set forth in formula I or formula II. In some embodiments, a described isoprenyl compound has the structure set forth in any of structures Ia-If. In some particular such embodiments, X is —OH. In some embodiments, a described isoprenyl compound is selected from the group consisting of those depicted in Table 1. In some embodiments, a described isoprenyl compound is AFC.

In some embodiments, the term "isoprenyl compound" may encompass prodrugs and/or esters of compounds of formula I, formula II, and Ia-If. As discussed herein, isoprenyl compounds may be provided in salt form. In particular, in some embodiments, a isoprenyl compound is provided as a pharmaceutically acceptable salt of a compound of any one of the above-listed formulae or classes and subclasses of formulae as described and defined herein.

The described isoprenyl compounds may exist in particular geometric or stereoisomeric forms. The present invention contemplates all such isoprenyl compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. In certain embodiments, the present invention relates to a isoprenyl compound represented by any of the structures outlined herein, wherein the compound is a single stereoisomer.

"Acyl": As used herein, the term "acyl" refers to a radical formed from an organic acid by removal of a hydroxyl group.

"Additional active ingredient": As used herein, the phrase "additional active ingredient" refers to an agent, other than a described isoprenyl compound, that exerts a pharmacological, dermatological or any other beneficial activity. It is to be understood that "other beneficial activity" may be one that is only perceived as such by the subject using the inventive compositions. Typically, an additional active ingredient, as that term is used herein, refers to a pharmaceutically active agent that is administered in combination with a described isoprenyl compound of the present invention.

"Aliphatic": The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, cycloalkynyl moieties. Thus, as used herein, the term "alkyl" includes straight, branched and cyclic alkyl groups (see below). An analogous convention applies to other generic terms such as "alkenyl", "alkynyl", and the like. Furthermore, as used herein, the terms "alkyl", "alkenyl", "alkynyl", and the like encompass both substituted and unsubstituted groups. In some embodiments, an aliphatic group contains 1-25 aliphatic carbon atoms. In some embodiments, an aliphatic group contains from 1 to 25, from 1 to 24, from 1 to 23, from 1 to 22, from 1 to 21, from 1 to 20, from 1 to 19, from 1 to 18, from 1 to 17, from 1 to 16, from 1 to 15, from 1 to 14, from 1 to 13, from 1 to 12, from 1 to 11, from 1 to 10, from 1 to 9, from 1 to 8, from 1 to 7, from 1 to 6, from 1 to 5, from 1 to 4, from 1 to 3, from 1 to 2, from 2 to 3, or 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, 20 to 21, 21 to 22, 22 to 23, 23 to 24, or 24 to 25 aliphatic carbon atoms. In certain embodiments, as used herein, "lower alkyl" is used to indicate those alkyl groups (cyclic, acyclic, substituted, unsubstituted, branched, or unbranched) having 1-6 carbon atoms. In some embodiments, wherein a portion of a term such as alkyl, alkenyl, alkynyl, cycloalkyl, cycloalkenyl, cycloalkynyl is used within a different generic term (e.g., dialkylamino, alkoxy, alkylthio, alkylamino), then it is understood that an analogous convention applies with respect to the number of carbon atoms present. In some embodiments, wherein a portion of a term such as alkyl, alkenyl, alkynyl, cycloalkyl, cycloalkenyl, cycloalkynyl is used within a different generic term (e.g., dialkylamino, alkoxy, alkylthio, alkylamino), then it is understood that an analogous convention applies with respect to the number of carbon atoms present.

"Alkenyl": As used herein, the term "alkenyl" denotes a monovalent group derived from a straight- or branched-chain aliphatic moiety having at least one carbon-carbon double bond by the removal of a single hydrogen atom. In some embodiments, the alkenyl group employed in the invention contains 10-25 carbon atoms. In some embodiments, the alkenyl group employed in the invention contains 10-20 carbon atoms. In some embodiments, the alkenyl group employed contains 10 carbon atoms. In some embodiments, the alkenyl group employed contains 15 carbon atoms. In some embodiments, the alkenyl group employed contains 20 carbon atoms. Alkenyl groups include, for example, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, and polyunsaturated alkenes including octadec-9,12-dienyl, octadec-9,12,15-trienyl, and eicos-5,8,11,14-tetraenyl, and the like.

"Alkyl": As used herein, the term "alkyl" means saturated, straight- or branched-chain hydrocarbon radicals derived from an aliphatic moiety containing between one and twenty-five carbon atoms by removal of a single hydrogen atom. In some embodiments, the alkyl group employed in the invention contains 10-25 carbon atoms. In some embodiments, the alkyl group employed in the invention contains 10-20 carbon atoms. In some embodiments, the alkyl group employed contains 10 carbon atoms. In some embodiments, the alkyl group employed contains 15 carbon atoms. In some embodiments, the alkyl group employed contains 20 carbon atoms. In some embodiments, the alkyl group employed in the invention contains 1-3 carbon atoms. In some embodiments, the alkyl group employed contains 1-2 carbon atoms. In some embodiments, the alkyl group contains 1 carbon atom. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, tridecyl, tetradecyl, pentadecyl, hexadecyl, heptadecyl, octadecyl, nonadecyl, eicosyl, heneicosyl, docosyl, tricosyl, teteracosyl, pentacosyl, farnesyl, phytyl, geranyl, geranylgeranyl, and the like.

"Alkylamino": The term "alkylamino" refers to a group having the structure —NHR', wherein R' is aliphatic, as defined herein. In some embodiments, the aliphatic group contains 1-20 aliphatic carbon atoms. In certain other embodiments, the aliphatic group contains 1-10 aliphatic carbon atoms. In yet other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like. In certain embodiments, the "alkyl" portion of an "alkylamino" group contains 1-20 aliphatic carbon atoms.

"Alkylene": The term "alkylene" refers to a bivalent substituted or unsubstituted alkyl group. Unless otherwise specified, the alkylene group contains 1-25 aliphatic carbon atoms. An "alkylene chain" is a polymethylene group, i.e., —$(CH_2)_n$—, wherein n is a positive integer, preferably from 1 to 6, from 1 to 5, from 1 to 4, from 1 to 3, from 1 to 2, from 2 to 3, or 3 to 4, 4 to 5, 5 to 6. A substituted alkylene chain is a polymethylene group in which one or more methylene hydrogen atoms are replaced with a substituent. Suitable substituents include those described herein for a substituted aliphatic group.

"Alkynyl": As used herein, the term "alkynyl" denotes a monovalent group derived from a straight- or branched-chain hydrocarbon moiety containing at least one carbon-carbon triple bond by removal of a single hydrogen atom. In some embodiments, an alkynyl group employed in the invention contains 10-25 carbon atoms. In some embodiments, an alkynyl group employed in the invention contains 10-20 carbon atoms. In some embodiments, an alkynyl group employed contains 10 carbon atoms. In some embodiments, an alkynyl group employed contains 15 carbon atoms. In some embodiments, an alkynyl group employed contains 20 carbon atoms. In some embodiments, an alkynyl group employed in the invention contains 2-3 carbon atoms. In some embodiments, an alkynyl group employed contains 2 carbon atoms. In some embodiments, an alkynyl group employed contains 3 carbon atoms. Representative alkynyl groups include, but are not limited to, ethynyl, 2-propynyl (propargyl), 1-propynyl, and the like.

"Alkoxy", or "Thioalkyl": The term "alkoxy", or "thioalkyl" as used herein refers to an alkyl group, as previously defined, attached to the parent molecule through an oxygen atom or through a sulfur atom. In some embodiments, the alkyl, alkenyl, and alkynyl groups contain 1-20 alipahtic carbon atoms. In certain other embodiments, the alkyl, alkenyl, and alkynyl groups contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of alkoxy include but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like. In certain embodiments, the "alk" or "alkyl" portion of an "alkoxy" or "thioalkyl" group contains 1-20 aliphatic carbon atoms.

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). A non-human animal may be a transgenic animal. In some embodiments, the term animal is used to refer to veterinary animals (e.g., a bird, a horse, a cow, a primate, a dog, a cat, a mouse, a rodent or a pig).

"Anti-acne agent": As used herein, the term "anti-acne agent" refers to a group of chemical substances that when topically administered at the site of acne comedomes or microcomedomes, leads to a visible reduction of symptoms associated with the epithelial condition of acne vulgaris. Representative anti-acne agents include, for example, keratolytics, such as salicylic acid, sulfur, glycolic, pyruvic acid, resorcinol, and N-acetylcysteine; and retinoids such as retinoic acid and its derivatives (e.g., cis and trans, esters).

"Anti-bacterial agent": As used herein, the term "anti-bacterial agent" refers to an agent that inhibits the growth of a bacterium or kills a bacterium or results in bacterial decolonization of a surface. In some embodiments, the anti-bacterial agent can have bactericidal effect. In some embodiments, the anti-bacterial agent can have bacteristatic effect. In some embodiments, the anti-bacterial agent can have both bactericidal and bacteristatic effects. As used herein, the term "anti-bacterial agent" refers to both an antibacterial compound or pharmaceutically acceptable salts thereof.

"Antibiotic agent": As used herein, the term "antibiotic agent" means any of a group of chemical substances, isolated from natural sources or derived from antibiotic agents isolated from natural sources, having the capacity to inhibit the growth of, or to destroy bacteria, and other microorganisms, used chiefly in the treatment of infectious diseases. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, sulfonamides, fluoroquinolones, and lincosamides.

"Antiseptic agent": As used herein, the term, "antiseptic agent" refers to a chemical agent that kills pathogenic or non-pathogenic bacteria. Antiseptic agents are sometimes referred to as "disinfectant agents", particularly when used to treat hard surfaces.

"Anti-dandruff agent": As used herein, the term "anti-dandruff agent" is an agent that reduces, eliminates or prevents a scurf from forming on skin, especially of the scalp, that comes off in small white or grayish scales. Exemplary anti-dandruff ingredients usable in context of the present invention include, without limitation, butoconazole, climbazole, coal tar, clotrimazole, dichlorophenyl imidazolodioxalan, imidazoles (e.g., fluconazole, ketoconazole, itraconazole, miconazole, miconazolenitrite, povidone-iodine, sulconazole, tioconazole), salicylic acid, selenium sulfide, shale oil and the like (e.g., sulfonated shale oil), sulfur, zinc pyrithione, and the like, and any possible stereo isomers thereof such as anthralin, piroctone olamine (Octopirox), selenium sulfide, and ciclopiroxolamine, and combinations thereof.

"Antihistamine agent": As used herein, the term "antihistamine agent" is an agent that counteracts histamine in the body and that is used for treating allergic reactions (such as hay fever) and cold symptoms. Non-limiting examples of antihistamines usable in context of the present invention include astemizole, brompheniramine, chlorpheniramine, clemastine, dexchlorpheniramine, diphenhydramine, loratadine, piperidines, piperazines, promethazine, terfenadine and tripolidine and combinations thereof.

"Anti-irritant": The term "anti-irritant", as used herein, is an agent that prevents or reduces soreness, roughness, or inflammation of a bodily part (e.g., skin). Presently known anti-irritants can be divided into water-soluble anti-irritants and water-insoluble anti-irritants. Representative examples of such compositions are described, for example, in U.S. Pat. No. 5,482,710, which is herein incorporated by reference. Suitable anti-irritants that can be used in the context of the present invention include, for example, steroidal and non steroidal anti-inflammatory agents or other materials such as allantoin, aloe vera, alpha-bisabolol, caffeine, chamomile, cola nitida extract, green tea extract, glycyrrhizic acid, licorice extract, tea tree oil, or other xanthines, and combinations thereof.

"Anti-oxidant agent": As used herein, the term "anti-oxidant agent" is an agent that inhibits oxidation or reactions promoted by oxygen or peroxides or other free radicals and/or free radical intermediates. Non-limiting examples of anti-oxidants that are usable in the context of the present invention include amines (e.g., N,N-diethylhydroxylamine, amino-guanidine), arginine pilolate, ascorbic acid (vitamin C) and its salts, ascorbyl esters of fatty acids, ascorbic acid and the like (e.g., magnesium ascorbyl phosphate, sodium ascorbyl phosphate, ascorbyl sorbate), bioflavonoids, butylated hydroxy benzoic acids and their salts, curcumin, dihydroxy fumaric acid and its salts, gallic acid and its alkyl esters (e.g., propyl gallate, uric acid and its salts and alkyl esters), glycine pidolate, grape skin/seed extracts, 6-hydroxy-2,5,7,8-tetramethylchroman-2-carboxylic acid (commercially available under the tradename Trolox®), lipoic acid, lysine, melanin, methionine, nordihydroguaiaretic acid, proline, rosemary extracts, silymarin, sorbic acid and its salts, sulfhydryl compounds (e.g., glutathione), superoxide dismutase, tea extracts, tocopherol acetate, tocopherol (vitamin E), tocopherol sorbate, and other esters of tocopherol and combinations thereof.

"Anti-skin atrophy agents": As used herein, the term "anti-skin atrophy agent" is an agent that is effective in replenishing or rejuvenating the epidermal layer by promoting or maintaining the natural process of desquamation. Examples of antiwrinkle and antiskin atrophy actives which can be used in context of the present invention include alpha-hydroxy acids (e.g. glycolic acid, and lactic acid), lipoic acid, lysophosphatidic acid, phytic acid, retinoic acid, its prodrugs, isomers (e.g., cis and trans) and analogues thereof, salicylic acid and the like, sclerosing agents or sclerosants, skin peel agents (e.g., phenol and the like), sulfur-containing D and L amino acids and the like and related salts, (e.g., N-acetyl derivatives, such as N-acetyl L-cysteine), and thiols (e.g. ethane thiol).

"Anesthetic agents": The term "anesthetic agent" as used herein is an agent that results in a reduction or loss of sensation. Non-limiting examples of anesthetic drugs that are suitable for use in the context of the present invention include pharmaceutically acceptable salts of bupivacaine, chlorprocaine, cocaine, dibucaine, dyclonine, etidocaine, hexylcaine, ketamine, lidocaine, mepivacaine, phenol, pramoxine, procaine, and tetracaine.

"Aryl" and "Heteroaryl": In general, the terms "aryl" and "heteroaryl" used alone or as part of a larger moiety as in "arylalkyl", "aryloxy", "heteroaryloxy" or "heteroarylalkyl" as used herein, refer to stable mono- or polycyclic, heterocyclic, and polyheterocyclic unsaturated moieties having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In some embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In some embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. The term "aryl" may be used interchangeably with the term "aryl ring." The term "heteroaryl" may be used interchangeably with the term "heteroaryl ring."

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments described herein.

"Arylene" and "Heteroarylene": The term "arylene" refers to an unsubstituted or substituted divalent group that is carbocyclic and aromatic. In some embodiments, rings in an arylene group are fused to one another. In some embodiments rings in an arylene group are not fused, but are nonetheless connected. In some embodiments, an arylene group includes some fused rings and some connected rings. In some embodiments, an arylene group includes aromatic rings. In some embodiments, an arylene group includes non-aromatic rings. In some embodiments, an arylene group includes some aromatic rings and some non-aromatic rings. In some embodiments, the arylene group has up to 5 rings, up to 4 rings, up to 3 rings, up to 2 rings, or one aromatic ring. For example, the arylene group can be phenylene. Exemplary arylene groups include any of the "aryl" moieties listed herein with the understanding that divalency is required to arrive at a corresponding "arylene" group from an "aryl" group. Exemplary substituents of "arylene" groups include replacement of one, two, three, or more of the hydrogen atoms thereon independently with any one or more of the moieties applicable for "aryl" and "heteroaryl," as defined herein. It will be appreciated by one skilled in the art that a carbon ring atom of an "arylene" can be replaced by one, two or three heteroatoms independently selected from S, O, and N while the remaining ring atoms are carbon, the divalent group being joined to the rest of the molecule via any two ring atoms, to form a "heteroarylene". Exemplary "heteroarylene" groups include any of the "heteroaryl" moieties listed herein with the understanding that divalency is required to arrive at a corresponding "heteroarylene" group from a "heteroaryl" group.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Astringent": As used herein, the term "astringent" is an agent that draws together or constricts body tissues and is effective in stopping the flow of blood or other secretions. In some embodiments, an astringent coagulate blood, and therefore can be used to arrest hemorrhage. In some embodiments, an astringent promotes healing, toughens skin and/or to decreases sweating. In some embodiments astringents are protein precipitants. Typically, astringents have low cell penetrability such that their action is limited to the cell surface and/or interstitial spaces. In some embodiments, astringent action is accompanied by contraction and wrinkling of tissues to which astringents are applied. In some embodiments, application of astringents is accompanied by blanching of recipient tissue. In some embodiments, astringents include one or more agents such as aluminum, bismuth, iron, manganese, zinc. Alternatively and/or additionally, such agents can be provided in any of a variety of forms including, for example, pharmaceutically acceptable salt forms.

"Bivalent, branched or unbranched, saturated or unsaturated, C$_2$-C$_6$ (e.g., C$_2$, C$_3$, C$_4$, C$_5$, or C$_6$) hydrocarbon chain": As used herein, the term "bivalent, branched or unbranched, saturated or unsaturated, $C_2$-$C_6$ (e.g., $C_2$, $C_3$, $C_4$, $C_5$, or $C_6$) hydrocarbon chain", refers to bivalent alkylene, alkenylene, and alkynylene chains that are straight or branched as defined herein.

"Carrier": The term "carrier" is used in accordance with its art-understood meaning, to refer to a material that is included in a pharmaceutical composition but does not abrogate the biological activity of pharmaceutically active agent(s) that are also included within the composition. Typically, carriers have very low toxicity to the animal to which such compositions are to be administered. In some embodiments, carriers are inert. In some embodiments, carriers are affirmatively beneficial (e.g., providing pharmaceutical and/or cosmetic benefits). In some embodiments, described isoprenyl compounds of Formulae I, I' and/or Ia, act as acceptable carriers. In some embodiments, AFC acts as an acceptable carrier. In some embodiments, the term "carrier" when used in the pharmaceutical context (e.g., pharmaceutically acceptable carrier) means that an agent is present in a composition but does not abrogate the biological activity of another agent(s) present in a composition. In some embodiments, the term "carrier" when used in a cosmetic context (e.g., cosmetically acceptable carrier) means that an agent is present in a composition but does not but does not abrogate the biological activity and/or aesthetic effect of another agent(s) present in a composition. In some embodiments, a cosmetically acceptable carrier is used to topically administer cosmetics with which described isoprenyl compounds will remain stable and bioavailable. It will be understood that "cosmetically acceptable carriers" and "carriers" as defined herein are similar, if not often identical, in nature. In some embodiments, the term "carrier" when used in a cosmeceutical context (e.g., cosmeceutical carrier) means that an agent is present in a composition but does not abrogate the biological activity and aesthetic effect of another agent(s) present in a composition.

"Caustic agents": As used herein, the term "caustic agent" is an agent that is capable of destroying or eating away epithelial tissue by chemical action. Caustic agents can be used to remove dead skin cells. For example, beta-hydroxy acids, naturally derived acids with a strong kerolytic effect, are useful for problem skin or peeling.

"Chelating Agent": The term "chelating agent" as used herein, is an agent that binds to a metal ion such as calcium ($Ca^{2+}$), magnesium ($Mg^{2+}$) and copper ($Cu^{2+}$), forming a metal complex known as a chelate. In some embodiments, a chelating agent is a ligand. In some embodiments, a chelating agent is an atom. In some embodiments, a chelating agent is an ion. In some embodiments, a chelating agent is an electron donor. In some embodiments, a pharmaceutical composition may contain a chelating agent (e.g., a mild agent, such as, ethylenediaminetetraacetic acid ("EDTA"), EDTA derivatives, or combinations thereof). In some embodiments, a chelating agent enhances a preservative or preservative system of the composition.

"Colorants": As used herein, the term "colorant" refers to pigments and/or dyes or a combination thereof, that are used to change hair color as cosmetic benefit requires. In some embodiments, pigments included in "colorants" include, but are not limited to, iron oxides, and titanium oxides. In some embodiments, dyes included in "colorants" include D&C approved colorants, FD&C approved colorants, and those approved for use in Europe and Japan. See Marmion, D. M., Handbook of US Colorants for Food, Drugs, Cosmetics, and Medical Devices, 3rd ed, 1991 herein incorporated by reference.

"Compatible": The term "compatible" as used herein means that the components of such a composition are capable of being combined with each other in a manner such that there is no interaction that would substantially reduce the efficacy of the composition under ordinary use conditions.

"Decolonization": As used herein, the term "decolonization" refers to the reduction in the number of bacteria present in or on a tissue, such as on the surface of skin, that do not necessarily cause immediate clinical symptoms.

"Demulcent": As used herein, the term "demulcent" is an agent used to primarily alleviate irritation, particularly mucous membranes or abraded tissues. Exemplary demulcents include acacia, agar, alginates, mucilages, benzoin, carbomer, gelatin, glycerin, gums, hydroxyethyl cellulose, hydroxypropyl cellulose, hydroxypropyl methylcellulose, hydrogels, dextrins, starches, certain sugars, and polymeric polyhydric glycols, propylene glycol, sodium alginate, tragacanth, and combinations thereof.

"Deodorant agent": As used herein, the term "deodorant agent" refers to a substance for inhibiting or masking perspiration or other bodily odors. Representative examples of deodorant agents that are usable in the context of the present invention include, without limitation, quaternary ammonium compounds such as benzethonium chloride, cetyl pyridinium chloride, cetyl-trimethylammonium bromide, diisobutyl phenoxy ethoxy ethyl dimethyl benzyl ammonium chloride, lauroyl sarcosine, sodium aluminum chlorohydroxy lactate, sodium N-lauryl sarcosine, sodium N-palmlthyl sarcosine, N-myristoyl glycine, potassium N-lauryl sarcosine, stearyl, trimethyl ammonium chloride, tricetylmethyl ammonium chloride, 2,4,4'-trichloro-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Other deodorant agents include, without limitation, odor absorbing materials such as carbonate and bicarbonate salts (e.g. as the alkali metal carbonates and bicarbonates, ammonium and tetraalkylammonium carbonates and bicarbonates, especially the sodium and potassium salts) or combination thereof.

"Dialkylamino": The term "dialkylamino" refers to a group having the structure —NRR', wherein R and R' are each an aliphatic group, as defined herein. R and R' may be the same or different in a dialkylamino moiety. In some embodiments, the aliphatic groups contain 1-20 aliphatic carbon atoms. In certain other embodiments, the aliphatic groups contain 1-10 aliphatic carbon atoms. In yet other embodiments, the aliphatic groups employed in the invention contain 1-8 aliphatic carbon atoms. In still other embodiments, the aliphatic groups contain 1-6 aliphatic carbon atoms. In yet other embodiments, the aliphatic groups contain 1-4 aliphatic carbon atoms. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In some embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl. In certain embodiments, the "alkyl" portion of an "dialkylamino" group contains 1-20 aliphatic carbon atoms.

"Effective amount": In general, the "effective amount" of an active agent (e.g., a therapeutic agent, composition, and/or formulation) refers to an amount sufficient to elicit the desired biological response. In some embodiments, a therapeutically effective amount of a substance is an amount that is sufficient, when administered to a subject suffering from or susceptible to a disease, disorder, and/or condition, to treat, diagnose, prevent, and/or delay the onset of one or more symptoms of the disease, disorder, and/or condition. As will be appreciated by those of ordinary skill in this art, and effective amount of a substance may vary depending on such factors as the desired biological endpoint, the substance to be delivered, the pharmacokinetics of the compound, the target cell or tissue, the disease being treated, the mode of administration, and the patient, etc. For example, the effective amount of a composition and/or formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. Those of ordinary skill in the art will appreciate that, commonly, a therapeutically effective amount will be administered over a series of individual doses. In some embodiments, the term "effective amount" when used in a pharmaceutical context (e.g., pharmaceutically effective amount) means that an agent is present in an amount sufficient to achieve a desired therapeutic effect. In some embodiments, the term "effective amount" when used in a cosmetic context (e.g., cosmetically effective amount) means that an agent is present in an amount sufficient to achieve an aesthetic effect. In some embodiments, the term "effective amount" when used in a cosmeceutical context (e.g., cosmeceutically effective amount) means that an agent is present in an amount sufficient to achieve a therapeutic and/or aesthetic effect.

"Emollients": As used herein, the term "emollients" refers to an agent that increases tissue moisture content, thereby rendering skin softer and more pliable. Increased moisture content in the skin can be achieved by preventing water loss with an occlusive water-immiscible barrier, by increasing the water-holding capacity in the skin with humectants, or by altering the desquamation of the outermost skin layer, the stratum corneum. In some embodiments, "emollients" are typically bland, fatty or oleaginous materials which can be applied locally, particularly to the skin. Useful emollients include cetyl alcohol, glycerin, hydrophilic petrolatum, isopropyl myristate, lanolin, mineral oil, myristyl alcohol, oleyl alcohol, paraffin, petrolatum, spermaceti, vegetable oils, waxes, white ointment, white petroleum, yellow ointment or combinations thereof.

"Emulsifier": The term "emulsifier" as used herein promotes formation and stabilization of an emulsion. Suitable emulsifiers may be finely divided solids, natural materials, or synthetic materials. Natural emulsifying agents may be derived from either animal or vegetable sources. Those from animal sources include casein, cholesterol, egg yolk, gelatin, or wool fat or combinations thereof. Those from vegetable sources include acacia, chondrus, pectin or tragacanth or combinations thereof. Vegetable sources specifically from cellulose derivatives include carboxymethyl cellulose and methyl cellulose to increase the viscosity. Finely divided emulsifiers include aluminum hydroxide, bentonite, magnesium hydroxide, or magnesium trisylicate. Synthetic agents include anionic, cationic or nonionic agents, and include benzalkonium chloride, polyethylene glycol 400 monostearate, sodium lauryl sulfate, or combinations thereof.

"Fragrance": As used herein, the term "fragrance" refers to an agent having a pleasant aroma. Suitable fragrances include, but are not limited to, camphor synthetic, chamomile, clove oil, eucalyptus oil, lavender, peppermint oil, and the like.

"Hair Conditioning Agents": As used herein, the term "hair conditioning agent" refers to an agent that is suitable for use in conditioning hair (e.g., so as to further improve the condition of the hair). In some embodiments, representative hair conditioning agents include, for example, one or more alkoxylated alcohols, alkoxylated amides, alkoxylated carboxylic acids, cationic surfactants, collagens, dimethicone polyols, esters (e.g., glyceryl esters), halogenated quaternary ammonium compounds, keratins, modified silicones, proteins, polymeric ethers, quaternary ammonium compounds, or sorbitan derivatives, or combinations thereof.

"Halo" and "Halogen": The terms "halo" and "halogen" as used herein refer to an atom selected from fluorine, chlorine, bromine, and iodine.

"Heteroaliphatic": The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In some embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments described herein.

"Heteroatom": As used herein, the term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$_x$ (as in N-substituted pyrrolidinyl)).

"Heterocycle" or "Heterocyclyl": As used herein, the terms "heterocycle", "heterocyclyl", "heterocyclic radical", and "heterocyclic ring" are used interchangeably and refer to a stable 3- to 7-membered monocyclic or 7-10-membered bicyclic heterocyclic moiety that is either saturated or partially unsaturated, and having, in addition to carbon atoms, one or more, preferably one to four heteroatoms independently selected from nitrogen, oxygen, or sulfur. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N (as in 3,4-dihydro-2H-pyrrolyl), NH (as in pyrrolidinyl), or $NR_x$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. In certain embodiments, one or more carbon atoms may be substituted with an oxo group in the heterocyclyl ring. Examples of such groups include, without limitation, an isoindolin-1,3-dione moiety. A heterocyclyl group may be mono- or bicyclic. The term "heterocyclylalkyl" refers to an alkyl group substituted by a heterocyclyl, wherein the alkyl and heterocyclyl portions independently are optionally substituted.

"Hormone": As used herein, the term "hormone" refers to natural substances produced by organs of the body that travel by blood to trigger activity in other locations or their synthetic analogs. Suitable hormones for use in the context of the present invention include, but are not limited to, calciferol (Vitamin $D_3$) and its products, androgens, estrogens and progesterones.

"Hydrocarbon": The term "hydrocarbon", as used herein, refers to any chemical group comprising hydrogen and carbon. In some embodiments, a hydrocarbon consists of hydrogen and carbon. A hydrocarbon may be substituted or unsubstituted. A hydrocarbon may be unsaturated, saturated, branched, unbranched, cyclic, or polycyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions. As used herein, a "bivalent hydrocarbon" refers to alkylene, alkenylene, or alkynylene, etc.

"Hypopigmenting agents": As used herein, the term "hypopigmenting agents" refers to substances capable of depigmenting the skin. Suitable hypopigmenting agents include hydroquinones, mequinol, and various protease inhibitors including serine protease inhibitors, active soy and retinoic acid.

"In combination": As used herein, the phrase "in combination" refers to agents that are simultaneously administered to a subject. It will be appreciated that two or more agents are considered to be administered "in combination" whenever a subject is simultaneously exposed to both (or more) of the agents. Each of the two or more agents may be administered according to a different schedule; it is not required that individual doses of different agents be administered the same time, or in the same composition. Rather, so long as both (or more) agents remain in the subject's body, they are considered to be administered "in combination".

"Independently selected": The term "independently selected" is used herein to indicate that the R groups can be identical or different.

"Irritant": As used herein, the term "irritant" is a material that acts locally on the skin to induce, based on irritant concentration, hyperemia, inflammation, and desiccation. Irritant agents include, but are not limited to, alcohol, aromatic ammonia spirits, benzoin tincture, camphor capsicum, and coal tar extracts. In some embodiments, the irritant is a rubefacient.

"Keratolytics": As used herein, "keratolytics" (desquamating agents) act to remove outer layers of the stratum corneum. This is particularly useful in hyperkeratotic areas. The keratolytics include benzoyl peroxide, fluorouracil, resorcinol, salicylic acid, tretinoin, and the like.

"Moisturizing agent": As used herein a "moisturizing agent" is a substance that adds or restores moisture to the skin. Representative examples of moisturizing or humectant agents that are usable in the present invention include, without limitation, acetamide monoethanolamine urazole, aloe vera in any of its variety of forms (e.g., aloe vera gel), allantoin, guanidine, glycolic acid and glycolate salts (e.g. ammonium salt and quaternary alkyl ammonium salt), hyaluronic acid, lactamide monoethanolamine, polyethylene glycols, polyhydroxy alcohols (e.g., sorbitol, glycerol, hexanetriol, propylene glycol, butylene glycol, hexylene glycol and the like), sugars and starches, sugar and starch derivatives (e.g., alkoxylated glucose), and any combination thereof.

"Non-steroidal anti-inflammatory agents": As used herein, the term "non-steroidal anti-inflammatory agents" refers to a large group of agents that are aspirin-like in their action, including acetaminophen, Advil®, Aleve®, ibuprofen, naproxen sodium and Tylenol® Additional examples of non-steroidal anti-inflammatory agents that are usable in the context of the present invention include, without limitation, acetic acid derivatives (e.g., acematacin, clindanac, diclofenac, felbinac, fenclofenac, fentiazac, furofenac, indomethacin, isoxepac, ketorolac, oxepinac, sulindac, tiopinac, tolmetin, zidometacin and zomepirac), benorylate, diflunisal, disalcid, fenamates (e.g., flufenamic, meclofenamic, mefenamic, niflumic and tolfenamic acids), fendosal, oxicams (e.g., CP-14,304, isoxicam, piroxicam, sudoxicam, and tenoxicam), propionic acid derivatives (e.g., alminoprofen, benoxaprofen, carprofen, fenbufen, fenoprofen, flurbiprofen, ibuprofen, indopropfen, ketoprofen, miroprofen, naproxen, oxaprozin, pirprofen, pranoprofen, suprofen, tiaprofenic and tioxaprofen), pyrazoles (e.g., azapropazone, feprazone, oxyphenbutazone, phenylbutazone and trimethazone), safapryn, solprin, trilisate.

"Penetration enhancer" and "pharmaceutically acceptable penetration enhancer": The term "penetration enhancer" and "pharmaceutically acceptable penetration enhancer" as used herein is a non-toxic agent that improves bioavailability of a topical composition. In some embodiments, a penetration enhancer is known to accelerate the delivery of a substance through the skin (e.g., disrupting the barrier function of the skin without compromising its barrier effects on microorganisms and toxins). Typically, a penetration enhancer is selected to be non-toxic to skin of the intended recipient (e.g., human). A penetration enhancer is also desirably compatible with any pharmaceutically active agent with which it is administered. Representative penetration enhancers include, for example, and without limitation, such agents as 1-substituted azacycloheptane-2-ones (e.g., 1-n-dodecyl-cyclazacycloheptan-2-one, available under the trademark Azone® from Whitby Research Incorporated, Richmond, Va.), dipolar-aprotic solvents (e.g., N,N-dimethylacetamide ("DMA"), decylmethylsulfoxide ("$C_{10}$ MSO"), dimethyl formamide ("DMF"), dimethylsulfoxide ("DMSO") and N-methyl-2-pyrrolidone ("NMP")), phospholipids (e.g., allantoin, fatty acid alcohols, lecithin, alcohols including glycerols such as polyethylene glycol monolaurate ("PGML"), glycerol monolaurate ("GML"), urazole, and the like). Penetration enhancer also can be a vegetable oil, such as, but not limited to, corn oil, cottonseed oil, safflower oil, and olive oil. Additional penetration enhancers generally can be found in Remington: The Science and Practice of Pharmacy, 20$^{th}$ ed. (Gennaro, A. R., et al., eds.) Lippincott Williams & Wilkins: Philadelphia (2000), which is incorporated herein by reference.

"pH adjusting agent": As used herein, the term "pH adjusting agent" as used herein is an agent that imparts suitable pH characteristics to compositions provided herein, (e.g., a substantially neutral pH), the pH of which depends on the specific utilization of the composition. In some embodiments, as the pH of skin is 5.5, it may be desireable to formulate compositions for topical skin application (to avoid irritation) having a pH value in a range of from about 4.0 to about 7.0, or in a range of from about 5.0 and 6.0, or about 5.5, or substantially 5.5. Suitable pH adjusting agents include, for example, but are not limited to, one or more adipic acids, buffers, citric acids, calcium hydroxides, glycines, magnesium aluminometasilicates, or combinations thereof.

"Pharmaceutically acceptable ester": The term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl moiety advantageously has not more than 6 carbon atoms. Examples of particular esters include formates, acetates, propionates, butyrates, acrylates, and ethylsuccinates. In some embodiments, the esters are cleaved by enzymes such as esterases.

"Pharmaceutically acceptable prodrugs": The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

"Preservative": As used herein, the term "preservative" has its art-understood meaning and refers to an agent that protects against undesirable chemical modifications of one or more components in a composition (e.g., protection against an undesirable chemical modification of an active ingredient). Suitable preservatives for use in the compositions of the present invention include, but are not limited to, one or more alkanols, disodium EDTA, EDTA salts, EDTA fatty acid conjugates, isothioazolinone, parabens such as methylparaben and propylparaben, polypropylene glycols, sorbates, urea derivatives such as diazolindinyl urea, or combinations thereof.

"Propellant": As used herein, the term "propellant" refers to an agent that propels the delivery of a composition in, e.g., a vaporized, aerosol nebulized, or spray form. Propellants often are used in metered-dose inhalers for the treatment of asthma and other respiratory disorders and for systemic treatments such as insulin for diabetes. Propellants also are used, for example, in nasal inhalers for treatment of allergic rhinitis, topical sprays, oral sprays, and other aerosol applications. An example of such propellants, without limitation, are the Dymel® pharmaceutical propellants manufactured by DuPont™ (Wilmington, Del.).

"Protecting group": One of ordinary skill in the art will appreciate that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, a-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4- methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMB S), benzylsulfonamide, trifluoromethylsulfonamide, and phenacylsulfonamide. Exemplary protecting groups are detailed herein. However, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

"Protective": As used herein, the term "protective" refers to an agent that isolates exposed surface of skin or other membrane from harmful or annoying stimuli. Exemplary protectives include dusting powders, adsorbents, mechanical protective agents, and plasters. Mechanical protectives are generally either collodions or plasters, and include, for example aluminum hydroxide gel, collodium, dimethicone, petrolatum gauze, absorbable gelatin film, absorbable gelatin sponge, zinc gelatin, kaolin, lanolin, anhydrous lanolin, mineral oil, mineral oil emulsion, mineral oil light, olive oil, peanut oil, petrolatum, silicones, hydrocolloids and the like. In some embodiments, a protective includes an adherent, continuous film that may be flexible or semi-rigid depending on the materials and the formulations as well as the manner in which they are applied. In some embodiments, a "protective" may be a "demulscent" as described herein.

"Racemic": As used herein, a racemic mixture means about 50% of one enantiomer and about 50% of its corresponding enantiomer relative to all chiral centers in a molecule. Compounds of the present invention may encompass enantiomerically pure, enantiomerically enriched, and racemic mixtures.

"Sclerosing agent": As used herein, the term "sclerosing agent" is an agent (e.g., chemical irritant) that is injected into a vein in sclerotherapy. Exemplary sclerosants include laureth 9 and ethanolamine oleate, morrhuate sodium, sodium tetradecyl sulfate.

"Small Molecule": In general, as used herein, the term "small molecule" refers to an organic compound either synthesized in the laboratory or found in nature. Typically, a small molecule is characterized in that it contains several carbon-carbon bonds, and has a molecular weight of less than 1500, although this characterization is not intended to be limiting for the purposes of the present invention. Small molecules that act as binding agents as described herein are typically small molecules having a basic nitrogen moiety.

"Solubilizing agent": As used herein, the term "solubilizing agent" are those substances that enable solutes to dissolve. Representative examples of solubilizing agents that are usable in the context of the present invention include, without limitation, complex-forming solubilizers (e.g., citric acid, ethylenediamine-tetraacetate, sodium meta-phosphate, succinic acid, urea, cyclodextrin, polyvinylpyrrolidone, diethylammonium-ortho-benzoate, etc.), n-alkyl amine n-oxides, micelle-forming solubilizers (e.g., TWEEN®, including TWEEN 80®), organic solvents (e.g., acetone, phospholipids and cyclodextrins), polyoxamers, polyoxyethylene n-alkyl ethers, and polyoxyethylene sorbitan fatty acid ester.

"Steroidal anti-inflammatory agent": As used herein, the term "steroidal anti-inflammatory agent", refers to any one of numerous compounds containing a 17-carbon 4-ring system and includes the sterols, various hormones (as anabolic steroids), and glycosides. Representative examples of steroidal anti-inflammatory drugs include, without limitation, corticosteroids such as alpha-methyl dexamethasone, amcinafel, amcinafide, beclomethasone dipropionates, beclomethasone dipropionate, betamethasone and the balance of its esters, chloroprednisone, chlorprednisone acetate, clescinolone, clobetasol valerate, clocortelone, cortisone, cortodoxone, desonide, desoxycorticosterone acetate, desoxymethasone, dexamethasone, dexamethasone-phosphate, dichlorisone, dichlorisone, diflorasone diacetate, diflucortolone valerate, difluorosone diacetate, diflurosone diacetate, diflurprednate, fluadrenolone, flucetonide, fluclorolone acetonide, flucloronide, flucortine butylesters, fludrocortisone, fludrocortisone, fludrocortisone, flumethasone pivalate, flunisolide, fluocinonide, fluocortolone, fluoromethalone, fluosinolone acetonide, fluperolone, fluprednidene (fluprednylidene) acetate, fluprednisolone, fluradrenolone acetonide, fluradrenolone, flurandrenolone, halcinonide, hydrocortamate, hydrocortisone acetate, hydrocortisone butyrate, hydrocortisone valerate, hydrocortisone cyclopentylpropionate, hydrocortisone, hydroxyltriamcinolone, medrysone, meprednisone, methylprednisolone, paramethasone, prednisolone, prednisone, triamcinolone acetonide, triamcinolone, and combinations thereof.

"Substituted": It will be appreciated that the compounds, as described herein, may be substituted with any number of substituents or functional moieties. In general, the term "substituted" whether preceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

"Thickeners": As used herein, the term "thickener" refers to agents that make a composition more dense or viscous in consistency. Suitable thickeners that can be used in the context of the present invention include, for example, non-ionic water-soluble polymers such as hydroxyethylcellulose (commercially available under the Trademark Natrosol® 250 or 350), cationic water-soluble polymers such as Polyquat 37 (commercially available under the Trademark Synthalen® CN), fatty alcohols, fatty acids, anionic polymers, and their alkali salts and mixtures thereof.

"Thio": The term "thio" used alone or as part of a larger moiety as in "alkylthio", "arylthio", "heteroalkylthio", or "heteroarylthio" refers to presence of a sulfur atom (e.g., as replacement of an oxygen). For example, "alkylthio" refers to an alkyl group, as previously defined, attached to the parent molecule through a sulfur atom. Similarly, "arylthio" refers to an aryl group, as previously defined, attached to the parent molecule through a sulfur atom.

"Treat," "treating" and "treatment": As used herein, the terms "treat," "treating" and "treatment," contemplate an action that occurs while a patient is suffering from the specified disease or disorder, which reduces the severity of the disease or disorder. Thus, "treat", "treating", and "treatment" refer to any type of treatment that imparts a benefit to a subject afflicted with a disease, including improvement in the condition of the subject (e.g., in one or more symptoms), delay in the progression of the disease, prevention or delay of the onset of the disease, etc.

"Vitamin": As used herein, the term "vitamin" refers to any of various organic substances essential in minute quantities to the nutrition of most animals act especially as coenzymes and precursors of coenzymes in the regulation of metabolic processes. Non-limiting examples of vitamins usable in context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin B$_3$ (niacinamide and its derivatives), alpha hydroxy acids (such as glycolic acid, lactic acid, tartaric acid, malic acid, citric acid, etc.) and beta hydroxy acids (such as salicylic acid and the like).

DESCRIPTION OF THE DRAWING

FIG. 1 presents a table depicting the range of IC50 results (µg/mL) obtained for BPO, Deoxycycline, AFC, compound A, compound B, compound C, compound D, compound E, compound F, compound G, compound H, compound I, compound J, compound K, and compound L, demonstrating the anti-bacterial property.

FIG. 4 presents a table summarizing the activity ranges determined from an MPO activity assay using a *P. acnes*-induced mouse ear inflammation model, determined with dexamethasone (administered at a dose of 1.6 mg/20 µL), clobetasol (administered at a dose of 0.1 mg/20 µL), salicylic acid (administered at a dose of 0.4 mg/20 µL), AFC (administered at a dose of 0.8 mg/20 µL), compound A (administered at a dose of 0.8 mg/20 µL), compound B (administered at a dose of 0.4 mg/20 µL), compound D (administered at a dose of 0.4 mg/20 µL), compound F (administered at a dose of 0.4 mg/20 µL), compound G (administered at a dose of 0.4 mg/20 µL), compound I (administered at a dose of 0.4 mg/20 µL), compound J (administered at a dose of 0.4 mg/20 µL), compound K (administered at a dose of 0.4 mg/20 µL), and compound L (administered at a dose of 0.4 mg/20 µL), demonstrating that exemplary inventive compounds have high or moderate anti-acne activity.

FIG. 5 presents a table summarizing the activity ranges determined from an IL-6 cytokine release assay using a *P. acnes*-induced mouse ear inflammation model, determined with dexamethasone (administered at a dose of 1.6 mg/20 µL), clobetasol (administered at a dose of 0.1 mg/20 µL), salicylic acid (administered at a dose of 0.4 mg/20 µL), AFC (administered at a dose of 0.8 mg/20 µL), compound A (administered at a dose of 0.8 mg/20 µL), compound B (administered at a dose of 0.4 mg/20 µL), compound D (administered at a dose of 0.4 mg/20 µL), compound F (administered at a dose of 0.4 mg/20 µL), compound G (administered at a dose of 0.4 mg/20 µL), compound I (administered at a dose of 0.4 mg/20 µL), compound J (administered at a dose of 0.4 mg/20 µL), compound K (administered at a dose of 0.4 mg/20 µL), and compound L (administered at a dose of 0.4 mg/20 µL), demonstrating that exemplary inventive compounds have high or moderate anti-acne activity.

FIG. 6 presents a table summarizing the activity ranges determined from an TNF-α cytokine release assay using a *P. acnes*-induced mouse ear inflammation model, determined with dexamethasone (administered at a dose of 1.6 mg/20 µL), clobetasol (administered at a dose of 0.1 mg/20 µL), salicylic acid (administered at a dose of 0.4 mg/20 µL), AFC (administered at a dose of 0.8 mg/20 µL), compound A (administered at a dose of 0.8 mg/20 µL), compound B (administered at a dose of 0.4 mg/20 µL), compound D (administered at a dose of 0.4 mg/20 µL), compound F (administered at a dose of 0.4 mg/20 µL), compound G (administered at a dose of 0.4 mg/20 µL), compound I (administered at a dose of 0.4 mg/20 µL), compound J (administered at a dose of 0.4 mg/20 µL), compound K (administered at a dose of 0.4 mg/20 µL), and compound L (administered at a dose of 0.4 mg/20 µL), demonstrating that exemplary inventive compounds have high or moderate anti-acne activity.

FIG. 7 presents a table summarizing the activity ranges determined from an IL-8 cytokine release assay using a *P. acnes*-induced mouse ear inflammation model, determined with dexamethasone (administered at a dose of 1.6 mg/20 µL), clobetasol (administered at a dose of 0.1 mg/20 µL), salicylic acid (administered at a dose of 0.4 mg/20 µL), AFC (administered at a dose of 0.8 mg/20 µL), compound A (administered at a dose of 0.8 mg/20 µL), compound B (administered at a dose of 0.4 mg/20 µL), compound D (administered at a dose of 0.4 mg/20 µL), compound F (administered at a dose of 0.4 mg/20 µL), compound G (administered at a dose of 0.4 mg/20 µL), compound I (administered at a dose of 0.4 mg/20 µL), compound J (administered at a dose of 0.4 mg/20 µL), compound K (administered at a dose of 0.4 mg/20 µL), and compound L (administered at a dose of 0.4 mg/20 µL), demonstrating that exemplary inventive compounds have high or moderate anti-acne activity.

FIG. 8 presents a table summarizing the activity ranges determined from an IL-1β cytokine release assay using a *P. acnes*-induced mouse ear inflammation model, determined with dexamethasone (administered at a dose of 1.6 mg/20 µL), clobetasol (administered at a dose of 0.1 mg/20 µL), salicylic acid (administered at a dose of 0.4 mg/20 µL), AFC (administered at a dose of 0.8 mg/20 µL), compound A (administered at a dose of 0.8 mg/20 µL), compound D (administered at a dose of 0.8 mg/20 µL), compound F (administered at a dose of 0.4 mg/20 µL), compound G (administered at a dose of 0.4 mg/20 µL), and compound I (administered at a dose of 0.4 mg/20 µL), demonstrating that exemplary inventive compounds have high or moderate anti-acne activity.

DETAILED DESCRIPTION OF SOME EMBODIMENTS

Figure 2:
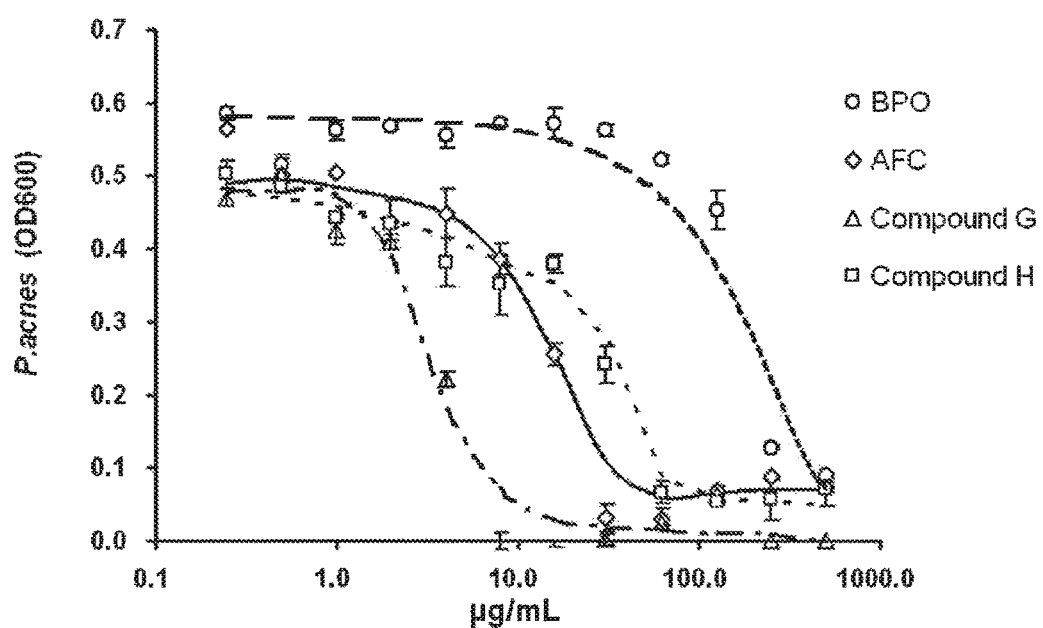
FIG. 2 presents a line graph depicting the growth curves for *Propiniobacterium acnes* obtained with BPO, AFC, compound G and compound H, demonstrating the anti-bacterial property.

Surprisingly, the inventors have discovered that certain isoprenyl compounds exhibit anti-bacterial activity, and, therefore, may be referred to as anti-bacterial agents. Such anti-bacterial agents are useful in the inhibition of bacterial cell growth or bacterial cell death or bacterial decolonization from surfaces, and/or in the treatment, prevention and management of bacterial-associated conditions.

As described herein, the present invention relates to certain compounds that are related to AFC and are therefore referred to as isoprenyl compounds.

Methods of the Present Invention

In some embodiments, the present invention provides, inter alia, methods to treat, prevent or ameliorate the symptoms of epithelial-related diseases, disorders, or conditions, caused or aggravated by bacteria in animals, particularly humans, in need of treatment thereof. In some embodiments, provided methods are useful for epithelial-related conditions (e.g. skin conditions, respiratory conditions, nasal conditions, ocular conditions, oral conditions, conditions of the external ear, vaginal conditions, genitourinary conditions, rectal conditions, bacterial-related conditions of similar tissues, etc.).

In some embodiments, exemplary skin conditions include impetigo; acne vulgaris; eczema; atopic dermatitis; infective dermatitis; psoriasis; rosacea; erythema; necrotizing cellulitis; cutaneous anthrax; cellulitis; erysipelas; ecthyma; cutaneous anthrax; necroticizing fasciitis; gangrene; septicaemia; pyoderma; endocarditis; toe web infections; sycosis barbae; furuncles and carbuncles; Staphylococcal scalded skin syndrome; blistering distal dactylitis; acute paronychia; folliculitis; cutaneous diphtheria; erythrasma; bacterial colonization of open wounds (e.g., cuts, lesions, scrapes, burns, lacerations, chronic wounds, infected animal bites, ulcerations, etc.).

In some embodiments, exemplary respiratory conditions include pneumonia; hypersensitivity pneumonitis; upper and lower respiratory tract infections (e.g., secondary bacterial infections in chronic bronchitis, asma, etc.); chronic obstructive pulmonary disease; diphtheria; bronchopulmonary dysplasia; pertussis; legionellosis (e.g., Legionnaires' disease, Pontiac fever; pharyngitis, etc.).

In some embodiments, exemplary nasal conditions include bacterial rhinitis; paranasal sinusitis, etc.

In some embodiments, exemplary ocular conditions include chronic blepharitis; endophthalmitis, etc.

In some embodiments, exemplary oral conditions include gingivitis; dental caries; early childhood caries, etc.

In some embodiments, exemplary conditions of the external ear include otitis media, etc.

In some embodiments, exemplary vaginal conditions include bacterial vaginosis; chanchroid; syphilis; donovanosis; gonorrhea; lymphogranuloma venereum; non-gonococcal urethritis; staphylococcal infection, vulvovaginitis; etc.

In some embodiments, exemplary genitourinary conditions include for example, *Granuloma inquinale*, perianal infections, etc.

In some embodiments, bacteria include Gram positive bacteria. In some embodiments, bacteria include Gram negative bacteria. In some embodiments, bacteria include Gram variable. Particularly relevant Gram positive bacteria include for example *Actinomyces* sp. (e.g., *Actinomyces israelli*, etc.); *Bacillus* sp. (e.g., *Bacillus anthracis*, etc.); *Corynebacterium* sp. (e.g., *Corynebacterium diphtheriae*, etc.); *Enterococcus* sp. (e.g., *Enterococcus faecalis*, etc.); *Gardnerella* sp. (e.g., *Gardnerella vaginalis*, etc.); *Mobiluncus* sp. (e.g., *Mobiluncus curtisii*, *Mobiluncus mulieris*, etc.); *Mycobacterium* sp. (e.g., *Mycobacterium immunogenum*, *Mycobacterium tuberculosis*, etc.); *Mycoplasma* sp. (e.g., *Mycoplasma pneumonia*, *Mycoplasma hyopneumoniae*, *Mycoplasma gallisepticum*, *Mycoplasma synoviae*, *Mycoplasma meleagridis*, *Mycoplasma gallinarum*, *Mycoplasma anatis*, *Mycoplasma hominis*, etc.); *Nocardia* sp. (e.g., *Nocardia asteroides*, *Nocardia brasiliensis*, *Nocardia caviae*, etc.); *Propionibacterium* sp. (e.g., *Propionibacterium acnes*, *Propionibacterium propionicus*, *Propionibacterium freudenreichii*, etc.); *Staphylococcus* sp. (e.g., *Staphylococcus aureus*, *Staphylococcus pseudintermedius*, *Staphylococcus epidermidis*, *Staphylococcus saprophyticus*, *Staphylococcus pyogenes*, etc.); *Streptococcus* sp. (e.g., *Streptococcus pneumoniae*, *Streptococcus mutans*, *Streptococcus mitis*, *Streptococcus salivarius*, *Streptococcus pyogenes*, etc.).

Particularly relevant Gram negative bacteria include for example *Actinobacillus* sp. (e.g., *Actinobacillus pleuropneumoniae*, etc.); *Bordatella* sp. (e.g., *Bordatella pertussis*, etc.); *Branhamella (Moraxella)* sp. (e.g., *Branhamella catarrhalis*, etc.); *Calymmatobacterium* sp. (e.g., *Calymmatobacterium granulomatis*, etc.); *Chlamydia* sp. (e.g., *Chlamydia trachomatis*, etc.); *Chlamydophila* sp. (e.g., *Chlamydophila pneumoniae*, etc.); *Eikenella* sp. (e.g., *Eikenella corrodens*, etc.); *Enterobacter* sp. (e.g., *Enterobacter aerogenes*, *Enterobacter cloacae*, etc.); *Escherichia* sp. (e.g., *Escherichia coli*, etc.); *Fusobacterium* sp. (e.g., *Fusobacterium nucleatum*, etc.); *Gardnerella* sp. (e.g., *Gardnerella vaginalis*, etc.); *Haemophilus* sp. (e.g., *Haemophilus influenzae*, *Haemophilus ducreyi*, etc.); *Histophilus* sp. (e.g., *Histophilus somnus*, etc.); *Klebsiella* sp. (e.g., *Klebsiella pneumoniae*, etc.); *Legionella* sp. (e.g., *Legionella pneumophila*, etc.); *Mannheimia* sp. (e.g., *Mannheimia haemolytica*, etc.); *Neisseria* sp. (e.g., *Neisseria gonorrhoeae*, etc.); *Ornithobacterium* sp. (e.g., *Ornithobacterium rhinotracheale*, etc.); *Pasteurella* sp. (e.g., *Pasteurella multocida*, etc.); *Pneumocystis* sp. (e.g., *Pneumocystis carinii*, etc.); *Prevotella* sp. (e.g., *Prevotella melaninogenica*, *Prevotella intermedia*, etc.); *Proteus* sp. (e.g., *Proteus vulgaris*, *Proteus mirabilis*, *Proteus penneri*, etc.); *Psuedomonas* sp. (e.g., *Psuedomonas aeruginosa*, etc.); *Treponema* sp. (e.g., *Treponema pallidum*, etc.); *Ureaplasma* sp. (e.g., *Ureaplasma urealyticum*, etc.); *Vibrio* sp. (e.g., *Vibrio vulnificus*, etc.); *Yersinia* sp. (e.g., *Yersinia pestis*, etc.), etc. Particularly relevant Gram variable bacteria include for example *Gardnerella* sp. (e.g., *Gardnerella vaginalis*, etc.).

In some embodiments, epithelial-related conditions may be associated with clinical indications (e.g., infection). In some embodiments, epithelial-related conditions may not be associated with clinical indications (e.g., infection). In some embodiments, epithelial-related conditions are associated with clinical indications (e.g., infection).

In some embodiments, methods of the present invention are useful in treating epithelial-related conditions in animals, including humans in need of treatment thereof. In some embodiments, methods of the present invention are useful in treating epithelial-related conditions in animals, including veterinary animals in need of treatment thereof.

In some embodiments, methods described herein comprise a step of administering to an animal, including a human, in need thereof, an effective amount of a compound of formulae I, Ia, Ib, Ic, Id, Ie, If and/or II and/or in described classes and subclasses thereof.

In some embodiments, provided herein, is a method for disinfection of a surface such as skin or surface of a medical device, etc.

In some embodiments, provided methods kill, inactivate, inhibit the growth of and/or decolonize bacteria on a surface. In some embodiments, provided methods are useful in killing, inactivating, inhibiting the growth of and/or decolonizing bacteria in biofilms on a surface. In some embodiments, provided methods are useful in preventing growth or colonization of bacteria to form biofilms on a surface.

In some embodiments, the present invention encompasses the finding that certain isoprenyl compounds exhibit superior anti-bacterial activity, as measured by the effect of administering such compounds on bacterial growth, when compared to anti-bacterial agents known in the art. Exemplary described isoprenyl compounds having improved anti-bacterial properties relative to, for instance, benzoyl peroxide (BPO), include, but are not limited to, compound A, compound B, compound C, compound D, compound E, compound F, compound G, compound H, compound I, compound J, compound K, and compound L. In some embodiments, isoprenyl compounds are administered to a subject suffering from or susceptible to one or more conditions, caused or aggravated by bacteria. In some embodiments, isoprenyl compounds are administered on a surface (e.g, epithelial surface) colonized with bacteria or susceptible to bacterial colonization, wherein the isoprenyl compound has a disinfectant effect.

Without wishing to be bound by any particular theory, it is believed that bacterial challenge triggers certain signal transduction cascades eliciting certain immune and/or inflammatory responses, which result in the release of a set of inflammatory mediators, such as cytokines and chemokines. In some embodiments, described isoprenyl compounds and compositions thereof modulate levels of inflammatory mediators, for example, cytokines. Non-limiting examples of inflammatory mediators modulated by described isoprenyl compounds and compositions thereof include, but are not limited to, IL-1α, IL-1β, IL-2, IL-3, IL-4, IL-5, IL-6, IL-7, IL-8, IL-9, IL-10, IL-11, IL-12/IL-23 p40, IL13, IL-17, IL-18, TGF-β, IFN-γ, GM-CSF, Groα, MCP-1 and TNF-α. Without wishing to be bound by any particular theory, it is believed that described isoprenyl compounds and compositions thereof modulate levels of inflammatory mediators that are associated with a variety of signal transduction pathways. Non-limiting examples of signal transduction pathways that result in release of inflammatory mediators such as cytokines, include but are not limited to G-protein-mediated, PPAR-mediated, Toll-like receptors-mediated, and TNF-α receptor-mediated. Without wishing to be bound by any particular theory, it is believed that certain isoprenyl compounds and compositions thereof modulate T-helper cell infiltration and accumulation.

In some embodiments, described isoprenyl compounds are capable of effectively inhibiting inflammatory responses triggered by bacterial challenge by decreasing levels or production of inflammatory mediators such as inflammatory cytokines, for example TNF IL-1α, IL-1β, IL-2, IL-3, IL-4, IL-5, IL-6, IL-7, IL-8, IL-9, IL-10, IL-11, IL-12/IL-23 p40, IL13, IL-17, IL-18, TGF-β, IFN-γ, GM-CSF, Groα, MCP-1 and TNF-α. In particular, the present invention encompasses the finding that certain described isoprenyl compounds have superior activity, as measured by percent inhibition of levels or production of proinflammatory cytokines in animal and cell-based inflammatory models, than other compounds in the same class. In some embodiments, described isoprenyl compounds are administered to a subject suffering from or susceptible to one or more conditions caused or aggravated by bacteria and associated with inflammation.

In some embodiments, described isoprenyl compounds are capable of effectively inhibiting inflammatory responses that are triggered by bacterial challenges. Thus, described isoprenyl compounds are inhibitors of infiltration and activation of inflammatory cells such as neutrophils (as measured by the activity of myeloperoxidase), lymphocytes, monocytes, mast cells, etc., and/or inhibitors of expression and activation of cell surface adhesion molecules (e.g. VCAM-1 and ICAM-1), and are therefore useful for treating one or more conditions caused or aggravated by bacteria and associated with inflammation, as described herein.

In general, the actual quantity of described isoprenyl compounds administered to a particular patient will vary depending on the severity and type of indication, the mode of administration, the particular compound used, the formulation used, and the response desired, and may optionally be further influenced by the condition of the patient, including other medications the patient may be receiving, the patient's habits or overall health, etc.

As will be appreciated by those of skill in the art, an appropriate dosage for treatment is administration, by any of the foregoing means or any other means known in the art, of an amount sufficient to bring about the desired therapeutic effect. Thus, a therapeutically effective amount includes an amount of a complex or composition that is sufficient to induce a desired effect, including specifically an anti-bacterial effect, an anti-inflammation effect or an anti-bacterial and an anti-inflammation effect. In general, complexes of the invention are highly active. For example, a described isoprenyl compound can be administered at about 10 μg/kg to about 50 mg/kg body weight, depending on the specific complex selected, the desired therapeutic response, the route of administration, the formulation and other factors known to those of skill in the art.

Acne Vulgaris

Acne Vulgaris (acne) is one of the most common skin disorders, affecting about 40-50 million people in the United States (James, W. D., *N Engl J Med*, 2005, 352: 1463-1472). The etiology of acne is now believed to involve genetic, hormonal, microbiological as well as immunological mechanisms (reviewed in Akhavan et al., *Am J Clin Dermatol*, 2003, 4: 473-492). The pathogenesis of acne is initiated by the follicular occlusion of adherent keratinocytes and hormone-triggered secretion of sebum resulting in the formation of pathophysiological microstructures called microcomedomes. These may enlarge to form visible non-inflammatory acne lesions, often referred to as open or closed comedomes. Conversion of such non-inflammatory acne lesions to an inflamed acne stage occurs principally as a result of the colonization of microcomedomes and comedomes with *Propionibacterium acnes*, an aerotolerant anerobic Gram-positive bacterium, which is largely commensal and constitutes a part of the human skin flora. Exemplary inflammatory mediators, for example cytokines whose levels may be elevated during the inflamed stages of acne (upon *P. acnes* colonization of microcomedomes and comedones) include TNFα, IL13, IL-6, IL-8, MCP-1 and Groα.

The most common topical acne treatment options include topical antibiotics, topical retinoids, benzoyl peroxide, salicylic acid, sulfur and azelaic acid, which either have anti-bacterial effects or anti-inflammatory effects but not both. In addition, the most-commonly-used anti-inflammatory treatment options for acne have little no effect on inflammatory mediator release.

Surprisingly, the inventors have discovered that certain described isoprenyl compounds exhibit an anti-bacterial effect and a bacteria-triggered anti-inflammatory effect and are therefore useful in the treatment, prevention and/or amelioration of symptoms of acne. In such embodiments, described isoprenyl compounds are therefore considered to be anti-acne agents. In some embodiments, described isoprenyl compounds of the present invention exhibit an anti-inflammatory effect, wherein the level of inflammatory mediators is inhibited. In some embodiments, described isoprenyl compounds of the present invention have a superior anti-bacterial effect when compared to other anti-bacterial compounds known in the art, such as benzoyl peroxide (BPO).

According to one aspect, the present invention provides methods of treating, preventing or ameliorating the symptoms of an epithelial-related condition, such as acne vulgaris, caused and aggravated by bacteria, such as *Propionibacterium acnes* in a subject in need thereof, wherein the method comprises of the step of administering to a subject in need thereof a therapeutically effective dose of one or more described isoprenyl compounds of any of formulae I, Ia, Ib, Ic, Id, Ie, If and/or II as described in classes and subclasses herein, having an anti-bacterial effect, as measured by the IC50, on bacterial growth of less than about 300 μg/mL. In certain embodiments, the present invention provides methods of treating, preventing or ameliorating the symptoms of an epithelial-related condition, such as acne vulgaris, caused and aggravated by bacteria, such as *Propionibacterium acnes* in a subject in need thereof, wherein the method comprises the step of administering to a subject in need thereof a therapeutically effective dose of one or more described isoprenyl compounds of any of formulae I, Ia, Ib, Ic, Id, Ie, If and/or II as described in classes and subclasses herein, having an anti-bacterial effect, as measured by the minimum bactericidal concentration of less than about 200 μg/mL.

According to one aspect, the present invention provides methods of treating, preventing or ameliorating the symptoms of an epithelial-related condition, such as acne vulgaris, caused and aggravated by bacteria, such as *Propionibacterium acnes* in a subject in need thereof, wherein the method comprises of the step of administering to a subject in need thereof a therapeutically effective dose of a described isoprenyl compound of any of formulae I, Ia, Ib, Ic, Id, Ie, If and/or II as described in classes and subclasses herein, having an anti-inflammatory effect, as exemplified by the inhibition of neutrophil infiltration, as measured by an inhibition of more than about 30% in an MPO activity assay, as determined using an in vivo mouse ear model in which inflammation is induced by *P. acnes* challenge. In certain embodiments, the present invention provides methods of treating, preventing or ameliorating the symptoms of an epithelial-related condition, such as acne vulgaris, caused and aggravated by bacteria, such as *Propionibacterium acnes* in a subject in need thereof, wherein the method comprises of the step of administering to a subject in need thereof a therapeutically effective dose of a described isoprenyl compound of any of formulae I, Ia, Ib, Ic, Id, Ie, If and/or II as described in classes and subclasses herein, having an anti-inflammatory effect, as exemplified by the inhibition of inflammatory mediator release, as measured by an inhibition of more than about 30% in a mediator release assay, as determined using mouse ear model or cell-based models. Exemplary inflammatory mediators such as, for instance, cytokines, include 11-6, TNF-α, IL-8. IL-β, MCP-1 and Groα.

Isoprenyl Compounds

Isoprenyl compounds for use in accordance with the present invention include compounds with structural similarity to N-acetyl-farnesyl-cysteine ("AFC", also referred to as N-acetyl-S-trans or trans-farnesyl-L-cysteine).

According to the present invention, described isoprenyl compounds include, for example, compounds of formula I:

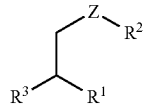

wherein:

$R^1$ is —C(O)X, wherein X is independently a protecting group, a halogen, R, —OR, —SR, —N(R)$_2$, a substituted or unsubstituted hydrazine, a substituted or unsubstituted 6-10 membered aryl ring, a substituted or unsubstituted 5-6 membered heteroaryl ring having 1-4 heteroatoms independently selected from nitrogen, oxygen, or sulfur; —NO$_2$; —PO$_3$H; —SO$_3$H; —CN; substituted or unsubstituted heteroaryl; or one of the following moieties:

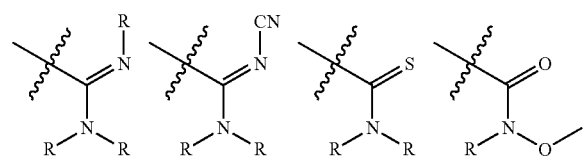

-continued

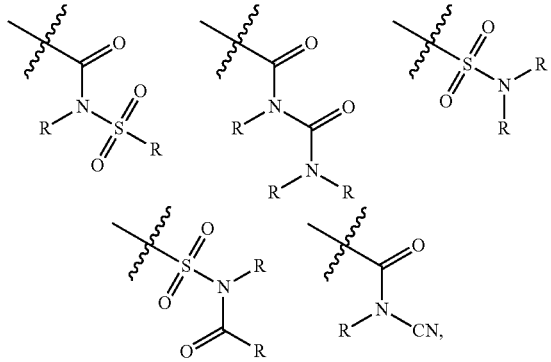

wherein each R is independently hydrogen or an optionally substituted group selected from $C_{1-6}$ aliphatic, $C_{1-6}$ heteroaliphatic, aryl, heteroaryl, or a cyclic radical;

$R^2$ is a substituted or unsubstituted, branched or unbranched $C_{10}$-$C_{25}$ aliphatic moiety;

$R^3$ is —NH$_2$, a peptide, or —N(R$^4$)(R$^5$);

$R^4$ is hydrogen or an optionally substituted group selected from $C_{1-6}$ aliphatic, $C_{1-6}$ heteroaliphatic, a cyclic radical, aryl or heteroaryl;

$R^5$ is heteroaryl; —C(=N—R$^6$)(R$^7$), wherein R$^6$ is selected from hydrogen, aliphatic, and —N(R)$_2$, and R$^7$ is selected from hydrogen, aliphatic, aryl, cyano, and —SO$_2$R; or C(O)LR$^8$, wherein L is a covalent bond or a bivalent, branched or unbranched, saturated or unsaturated, $C_2$-$C_6$ hydrocarbon chain wherein one or more methylene units of L is independently replaced by —O—, —S—, —NH—, —C(O)—, —C(=CH$_2$)—, or $C_3$-$C_6$ cycloalkylene, wherein L is optionally substituted by one or more groups selected from halogen, phenyl, an 8-10 membered bicyclic aryl ring, a 5-6 membered heteroaryl ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, a 5- to 7-membered monocyclic having 1-2 heteroatoms independently selected from nitrogen, oxygen, or sulfur or a 7-10 membered bicyclic heterocyclyl ring having 1-2 heteroatoms independently selected from nitrogen, oxygen, or sulfur; and R$_8$ is —R, —OR, —N(R)$_2$, a cyclic radical, aryl, heteroaryl, wherein each R is independently hydrogen or an optionally substituted group selected from $C_{1-6}$ aliphatic, $C_{1-6}$ heteroaliphatic, aryl, heteroaryl, or a cyclic radical; or a substituted or unsubstituted peptidic moiety; and Z is —S—, —O—, —NH—, —Se—, —S(=O)—, —S(=N)—, —SO$_2$—, —Se(=O)—, or —SeO$_2$—.

In some embodiments, a described isoprenyl compound has a structure depicted in formula Ia:

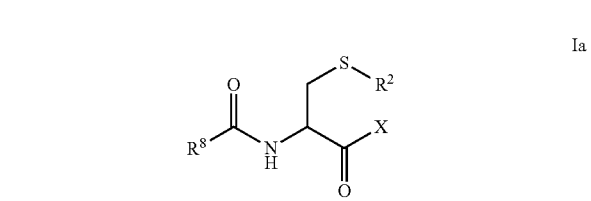

wherein R$^2$ is as defined herein;

X is —OH, halogen, methyl, —SH, —NH$_2$, or —N(R)$_2$, wherein R is hydrogen or $C_{1-3}$ alkyl; and R$^8$ is $C_{1-3}$ alkyl.

In some embodiments, a described isoprenyl compound has a structure depicted in formula Ib:

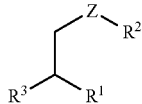

Ib wherein

R¹ is —CO₂H, —CO₂R, —CONH₂, —NO₂, —PO₃H, —CN, or —SO₃H, where R is as defined herein;

R² is farnesyl, phytyl, geranylgeranyl, substituted farnesyl, substituted phytyl, or substituted geranylgeranyl; and R³ is —NH₂ or a peptide.

In some embodiments, a described isoprenyl compound has a structure depicted in formula Ic:

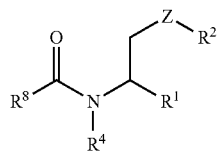

Ic wherein R² and R⁸ are as described herein;

R¹ is substituted or unsubstituted heteroaryl, or one of the following moieties:

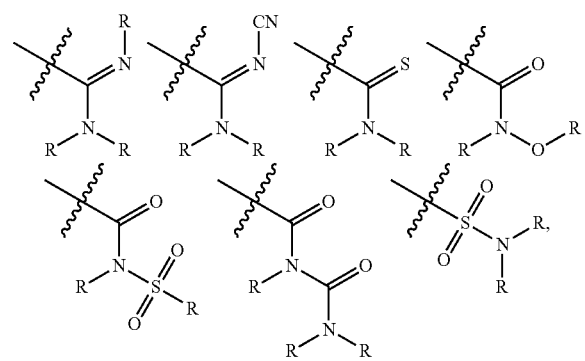

wherein R is as described herein; and

Z is —S—, —O—, —Se—, —SO—, —SO₂—, or —NH—.

In some embodiments, a described isoprenyl compound has a structure depicted in formula Id:

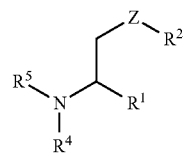

Id wherein R² and R⁴ are as described herein;

R¹ is substituted or unsubstituted heteroaryl, or one of the following moieties:

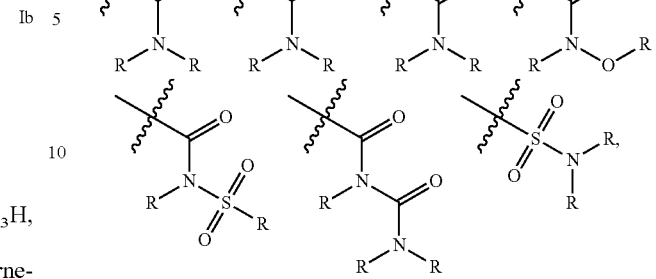

wherein R is as described herein;

R⁵ is heteroaryl or —C(=NR⁶)(R⁷), where R⁶ and R⁷ are as described herein; and

Z is —S—, —O—, —Se—, —SO—, —SO₂—, or —NH—.

In some embodiments, a described isoprenyl compound has a structure depicted in formula Ie:

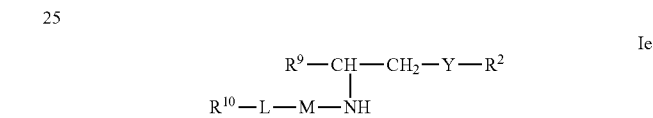

Ie

Wherein,

R² is as described herein;

R⁹ is —C(O)X, wherein X is independently R, —C(O)NHNH₂, —OR, a hydrogen, aryloxy, amino, alkylamino, dialkylamino, heteroaryloxy, hydrazine, a 6-10 membered aryl ring, a 5-6 membered heteroaryl ring having 1-4 heteroatoms independently selected from nitrogen, oxygen, or sulfur, wherein each R is independently hydrogen or an optionally substituted group selected from C₁₋₆ aliphatic or C₁₋₆ heteroaliphatic;

L is a bivalent, branched or unbranched, saturated or unsaturated, C₂-C₆ hydrocarbon chain wherein one or more methylene units of L is independently replaced by —O—, —S—, —NH—, —C(O)—, —CF₂—, —C(=CH₂)—, —CH=CH—, or an optionally substituted arylene, heteroarylene, C₃-C₆ cycloalkylene, C₃-C₆ heterocycloalkylene, or an 8-10-membered bicyclic heterocyclic moiety, and wherein L is optionally substituted by one or more groups selected from halogen, C₁-C₆ alkyl, phenyl, biphenyl, -benzyl, —CH₂-phenol, —CH(phenyl)₂, —OH, —NH₂, —NHC(O)CH₃, —NHC(O)NHCH₂CH₃, —C(O)NH₂, —C(O)NHCH₂CH₃, —CH₂C(O)OCH₂phenyl, —(CH₂)₂SCH₃, —(CH₂)₂C(O)NH₂, —(CH₂)₂C(O)OH, an 8-10 membered bicyclic aryl ring, a 5-6 membered heteroaryl ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, a 5- to 7-membered monocyclic having 1-2 heteroatoms independently selected from nitrogen, oxygen, or sulfur or a 7-10 membered bicyclic heterocyclyl ring having 1-2 heteroatoms independently selected from nitrogen, oxygen, or sulfur;

M is —C(O)—, —C(S), or —SO₂—;

R¹⁰ is hydrogen, F, CF₃, C₁-C₄ alkyl, —OH, —C(O)CH₃, —NH(OR^E), —NR^E₂, —NHNR^E₂, —SO₂R^E, —NH-phenyl, —SO₂-phenyl, -phenyl-NO₂, or —OR^E, wherein each $R^E$ is independently hydrogen, oxygen, or an optionally substituted group selected from $C_{1-6}$ aliphatic or $C_{1-6}$ heteroaliphatic;

Y is —O—, —N—, —S—, —Se—, —S(O)—, —S(=N)—, —SO$_2$—, —Se(O)—, or —Se(O)$_2$—;

In some embodiments, a described isoprenyl compound has a structure depicted in formula If:

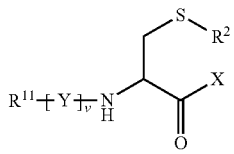

If wherein

Y is a natural or unnatural amino acid;

v is an integer between 1 and 100, inclusive; and $R^{11}$ is hydrogen, a protecting group, or an optionally substituted group selected from $C_{1-6}$ aliphatic, $C_{1-6}$ heteroaliphatic, aryl or heteroaryl.

In some embodiments of any of the foregoing structures I and Ia-If, $R^1$ is an optionally substituted heteroaryl moiety of one of the formulae:

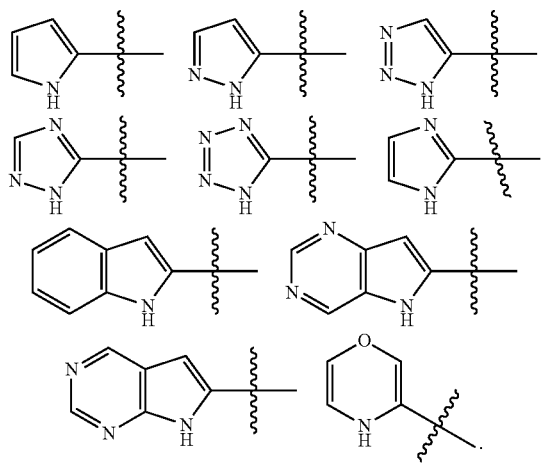

In some embodiments, $R^1$ is —CO$_2$H.

In some embodiments, described isoprenyl compounds of the above-described Formula are provided with the proviso that L and $R^{10}$ cannot together be $C_1$-$C_3$ unsubstituted non-halogenated alkyl.

In some embodiments, described isoprenyl compounds are of any of formulae I and/or Ia-If, wherein $R^2$ is a farnesyl group.

In some embodiments, described isoprenyl compounds are of any of formulae I and/or Ia-If, wherein $R^3$ is —NHCOCH$_3$.

In some embodiments, described isoprenyl compounds are of any of formulae I and/or Ia-If, wherein Z is —S.

In some embodiments, described isoprenyl compounds are of any of formulae I and/or Ia-If, wherein X is —OH.

In some embodiments, a described isoprenyl compound has a structure depicted in formula II:

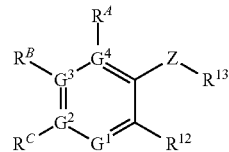

II wherein each of $G^1$, $G^2$, $G^3$, and $G^4$ is N or $CR^D$;

Z is S, O, Se, SO, SO$_2$, or NH;

$R^{12}$ is —C(O)X, wherein X is independently a protecting group, a halogen, R, —OR, —SR, —N(R)$_2$, a substituted or unsubstituted hydrazine, a substituted or unsubstituted 6-10 membered aryl ring, a substituted or unsubstituted 5-6 membered heteroaryl ring having 1-4 heteroatoms independently selected from nitrogen, oxygen, or sulfur; —NO$_2$; —PO$_3$H; —SO$_3$H; —CN; substituted or unsubstituted heteroaryl; or one of the following moieties:

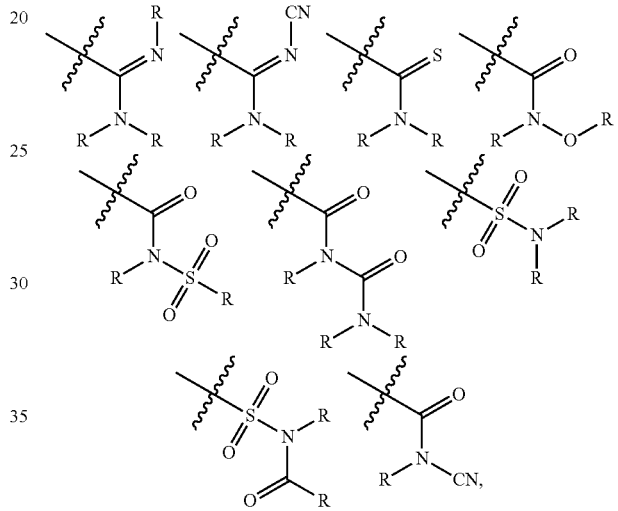

wherein each R is as described herein;

$R^{13}$ is an optionally substituted aliphatic group;

$R^A$, $R^B$, $R^C$, and $R^D$ are independently H, —NO$_2$, —OR$^{14}$, halogen, alkylN(R$^{14}$)$_2$, —N(R$^{14}$)$_2$, —C(=O)R$^{14}$, —C(=O)OR$^{14}$, —S(R$^{14}$), azido, —S—C≡N, alkyl, aryl, alkenyl, alkynyl, or a cyclic radical, wherein $R^A$, $R^B$, $R^C$, and $R^D$ are further optionally substituted;

$R^{14}$ is H, alkyl, aryl, alkenyl, alkynyl, or a cyclic radical, wherein $R^{14}$ is further optionally substituted.

In some embodiments, at least one of $G^1$, $G^2$, $G^3$, and $G^4$ is N; in some embodiments, at least two of $G^1$, $G^2$, $G^3$, and $G^4$ are N; in some embodiments, at least three of $G^1$, $G^2$, $G^3$, and $G^4$ are N; in some embodiments, at least four of $G^1$, $G^2$, $G^3$, and $G^4$ are N. In some embodiments, $G^1$ is N. In some embodiments, $G^1$ is N and at least one of $G^2$, $G^3$, and $G^4$ is N.

AFC, and many isoprenyl compounds are characterized by an ability to reduce methylation of a protein having a carboxyl-terminal -CAAX motif, wherein C=cysteine, A=any aliphatic amino acid, and X=any amino acid. (See Rando, U.S. Pat. No. 5,202,456). The methylation reaction which is inhibited is part of a series of post-translational modifications involving the -CAAX motif. These modifications include polyisoprenylation of the cysteine of the -CAAX motif (on the sulfur), proteolysis of the carboxyl-terminal three amino acids (-AAX) and methylation of the carboxyl group of cysteine.

Exemplary isoprenyl compounds for use in accordance with the present invention are set forth in Table 1 below.

TABLE 1
Exemplary Compounds:
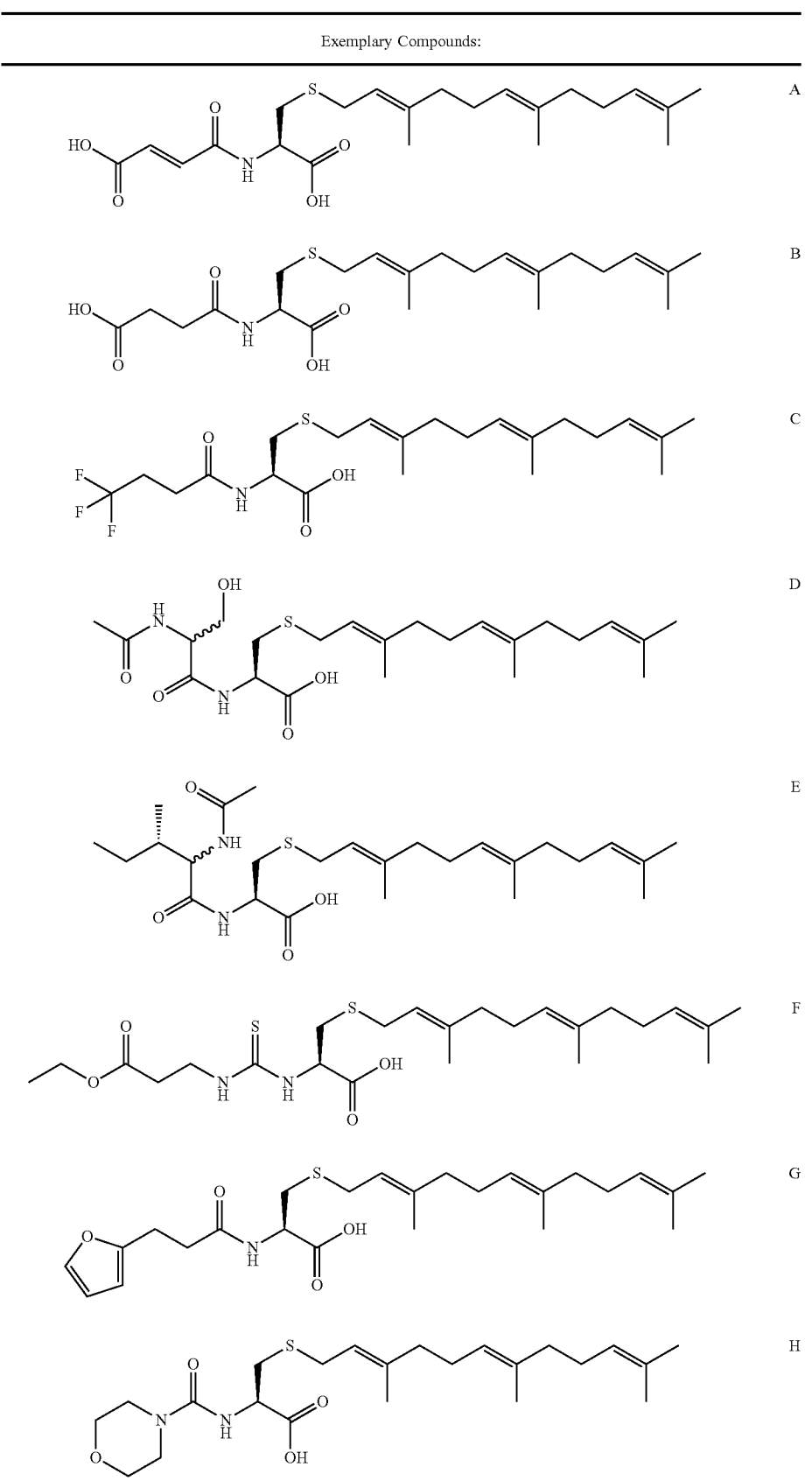

TABLE 1-continued

Exemplary Compounds:

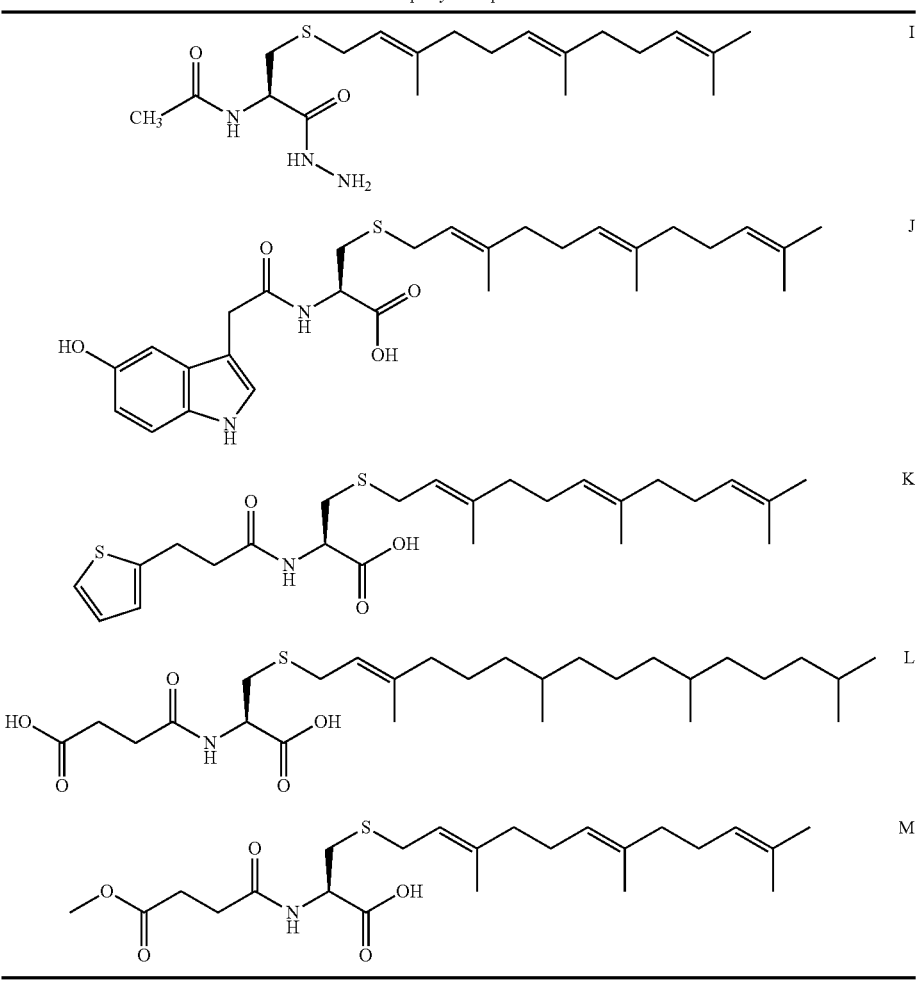

In some embodiments, the present invention contemplates the use of an isoprenyl compound as depicted in Table 1, above, or a pharmaceutically acceptable salt thereof.

In some embodiments wherein the present invention contemplates the use of an isoprenyl compound as depicted in Table 1, the compound is selected from the group consisting of A, B, C, D, and E. In certain embodiments wherein the present invention contemplates the use of an isoprenyl compound as depicted in Table 1, the compound is selected from the group consisting of A, C, and E.

In some embodiments wherein the present invention contemplates the use of an isoprenyl compound as depicted in Table 1, the compound is selected from the group consisting of A, C, D, E and I. In certain embodiments wherein the present invention contemplates the use of an isoprenyl compound as depicted in Table 1, the compound is selected from the group consisting of D, E and I.

In some embodiments wherein the present invention contemplates the use of an isoprenyl compound as depicted in Table 1, the compound is selected from the group consisting of G, H, I, J, K, L, and M. In certain embodiments wherein the present invention contemplates the use of an isoprenyl compound as depicted in Table 1, the compound is selected from the group consisting of G and H. In certain embodiments wherein the present invention contemplates the use of an isoprenyl compound as depicted in Table 1, the compound is selected from the group consisting of I, J, K, L, and M. In certain embodiments wherein the present invention contemplates the use of an isoprenyl compound as depicted in Table 1, the compound is selected from the group consisting of G, J, and K. In certain embodiments wherein the present invention contemplates the use of an isoprenyl compound as depicted in Table 1, the compound is selected from the group consisting of J, K, L, and M.

In some embodiments, the present invention contemplates the use of an isoprenyl compound as depicted in Table 1, wherein the compound is selected from the group consisting of A, C, G, H, and I. In certain embodiments wherein the present invention contemplates the use of an isoprenyl compound as depicted in Table 1, the compound is selected from the group consisting of G, H, and I.

Compounds of formulae I, Ia, Ib, Ic, Id, Ie, If and/or II, as disclosed herein, are provided according to the present invention in any of a variety of useful forms, for example as pharmaceutically acceptable salts, as particular crystal forms, etc. In some embodiments, prodrugs of one or more compounds of formulae I, Ia, Ib, Ic, Id, Ie, If and/or II are provided. Various forms of prodrugs are known in the art, for example as discussed in Bundgaard (ed.), *Design of Prodrugs*, Elsevier (1985); Widder et al. (ed.), *Methods in*

*Enzymology*, vol. 4, Academic Press (1985); Kgrogsgaard-Larsen et al. (ed.); *"Design and Application of Prodrugs"*, *Textbook of Drug Design and Development*, Chapter 5, 113-191 (1991); Bundgaard et al., *Journal of Drug Delivery Reviews*, 8:1-38 (1992); Bundgaard et al., *J. Pharmaceutical Sciences*, 77:285 et seq. (1988); and Higuchi and Stella (eds.), *Prodrugs as Novel Drug Delivery Systems*, American Chemical Society (1975).

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Unless otherwise indicated, the present invention encompasses racemic forms of compounds depicted herein as well as all enantiomers and stereoisomers, that is, both the stereomerically pure form (e.g., geometrically pure, enantiomerically pure, or diastereomerically pure) and enantiomeric and stereoisomeric mixtures.

A compound may be considered optically active or enantiomerically pure (i.e., substantially the R-form or substantially the S-form) with respect to a chiral center when a compound is present in about 90% ee (enantiomeric excess) or greater, preferably, equal to or greater than 95% ee with respect to a particular chiral center. A compound may be considered to be in enantiomerically enriched form when a compound is present in an enantiomeric excess of greater than about 80% ee, preferably greater than about 85% ee. As used herein, a racemic mixture means about 50% of one enantiomer and about 50% of its corresponding enantiomer relative to all chiral centers in the molecule. Thus, compounds of the present invention may encompass enantiomerically pure, enantiomerically enriched, and racemic mixtures.

Enantiomeric and stereoisomeric mixtures may be resolved into their component enantiomers or stereoisomers by well known methods, such as chiral-phase gas chromatography, chiral-phase high performance liquid chromatography, crystallizing a compound as a chiral salt complex, or crystallizing a compound in a chiral solvent or by enzymatic resolution of a compound, its precursor or its derivative. Enantiomers and stereoisomers may also be obtained from stereomerically or enantiomerically pure intermediates, reagents, and catalysts by well-known asymmetric synthetic methods.

Additionally, unless otherwise stated, the present invention encompasses compounds that differ from those explicitly depicted herein only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In some embodiments, the $R^1$ group of formulae I, Ia, Ib, Ic, Id, Ie, If and/or II comprises one or more deuterium atoms. In some embodiments, the $R^2$ group of formulae I, Ia, Ib, Ic, Id, Ie, If and/or II comprises one or more deuterium atoms. In some embodiments, the $R^3$ group of formulae I, Ia, Ib, Ic, Id, le, If and/or II comprises one or more deuterium atoms.

Mixtures of isomeric forms may be separated and/or purified by techniques as would be known to one skilled in this art, including but not limited to column chromatography.

In some embodiments, activity of described isoprenyl compounds may be characterized using a variety of in vitro or in vivo assays, involving a variety of cell-based or animal-based models.

In some embodiments, described isoprenyl compounds of formulae I, Ia, Ib, Ic, Id, Ie, If and/or II are anti-bacterial agents. In certain embodiments, described isoprenyl compounds exhibit an anti-bacterial effect. For example, ability of described isoprenyl compounds to kill, inactivate, and/or inhibit bacterial growth may be assessed using one or more assays that measure the amount of isoprenyl compound required to attain 50% inhibition of bacterial growth (IC50). One such exemplary assay is described herein in Example 14. In some embodiments, described isoprenyl compounds are considered to be inhibitors of bacterial growth, when they result in an IC50 of about 0.5 µg/mL, 1.0 µg/mL, 2.0 µg/mL, 5.0 µg/mL, 10.0 µg/mL, 20.0 µg/mL, 30.0 µg/mL, 40.0 µg/mL, 50.0 µg/mL, 100.0 µg/mL, 200.0 µg/mL or 300.0 µg/mL. In some embodiments, for example, ability of described isoprenyl compounds to kill, inactivate, and/or inhibit bacterial growth may be assessed, for example using one or more assays that measure the minimum concentration of isoprenyl compound resulting in inhibition of bacterial growth (Minimum Bactericidal Concentration or "MBC"). One such exemplary assay is described herein in Example 15. In some embodiments, described isoprenyl compounds are considered to be inhibitors of bacterial growth when they result in an MBC of about 0.5 µg/mL, 1.0 µg/mL, 2.0 µg/mL, 5.0 µg/mL, 10.0 µg/mL, 20.0 µg/mL, 30.0 µg/mL, 40.0 µg/mL, 50.0 µg/mL, 100.0 µg/mL, 200.0 µg/mL or 300.0 µg/mL.

In certain embodiments, described isoprenyl compounds exhibit an anti-inflammatory effect. For example, ability of described isoprenyl compounds to modulate inflammatory responses upon bacterial challenge may be assessed using one or more assays that assess inhibition of myeloperoxidase ("MPO"). One such exemplary assay is described herein in Example 16. In some embodiments, described isoprenyl compounds are considered to be inhibitors of inflammation when they show a percent inhibition in an MPO activity assay of at least about 10, 20, 30, 40, 50, 60, 70, 80, 90 or 95%, for example when provided at a dose of 0.8 mg/20 µL. In some embodiments, described isoprenyl compounds are considered to be inhibitors of inflammation when they show a percent inhibition in an MPO activity assay of at least about 5, 10, 15, 20, 25, 30, 35, 40, 50, 60, 70, 80, 90, or 95%, for example when provided at a dose of 0.4 mg/20 µL. In some embodiments, described isoprenyl compounds are considered to be inhibitors of inflammation when they show a percent inhibition in an MPO activity assay of at least about 5, 10, 15, 20, 25, 30, 35, 40, 50, 60, 70, 80, 90, or 95%, for example when provided at a dose of 0.2 mg/20 µL.

In some embodiments, the ability of described isoprenyl compounds to exhibit an anti-inflammatory effect upon bacterial challenge may be assessed, for example, by their ability to modulate the levels of inflammatory mediators such as, for instance, cytokines. Exemplary such cytokines include, but are not limited to, IL-1α, IL-1β, IL-2, IL-3, IL-4, IL-5, IL-6, IL-7, IL-8, IL-9, IL-10, IL-11, IL-12/IL-23 p40, IL13, IL-17, IL-18, TGF-β, IFN-γ, GM-CSF, Groα, MCP-1 and TNF-α. In further embodiments, described isoprenyl compounds modulate levels of inflammatory mediators such as cytokines that are induced by G-protein-mediated pathways. In further embodiments, described isoprenyl compounds modulate levels of inflammatory mediators such as cytokines that are induced by other signal transduction pathways involving, for example, Toll-like receptors ("TLRs"). In further embodiments, described isoprenyl compounds modulate levels of inflammatory mediators such as cytokines that are induced by other signal transduction pathways involving, for example, ATPγS-purinergic receptors. In further embodiments, described isoprenyl compounds modulate levels of inflammatory mediators such as cytokines that are induced by other signal transduction pathways involving, for example, TNFα receptors. In some embodiments, described isoprenyl compounds modulate levels of inflammatory mediators such as cytokines that are triggered by chemicals such as TPA.

The ability of described isoprenyl compounds to modulate inflammatory responses upon bacterial challenge may be assessed using one or more assays that measure the levels of inflammatory cytokines, for example using in vivo or cell-based inflammatory models. Certain exemplary such models include, for instance, a P. acnes-induced mouse ear inflammatory model to measure inhibition of inflammatory mediators such as IL-6, TNF-α, IL-8 and IL-1β, as described in Example 17, or a P. acnes-induced cytokine release inflammatory model in Normal Human Epidermal Keratinocyte ("NHEK") cell cultures to measure inhibition of inflammatory mediators such as IL-8, as described in Example 18, or an LPS-TLR4-induced cytokine release inflammatory model in Human Microvascular Endothelial cell lines ("HMEC-1") to measure inhibition of inflammatory mediators such as IL-8, as described in Example 19, or a PGN-TLR2-induced cytokine release inflammatory model in Normal Human Epidermal Keratinocyte ("NHEK") cell cultures to measure inhibition of inflammatory mediators such as IL-8, as described in Example 20, or an ATPγS-purinergic receptor-induced cytokine release inflammatory model in HMEC-1 cell lines to measure the inhibition of inflammatory mediators such as IL-8, MCP-1 and Groα, as described in Example 21, or a TPA-induced cytokine release inflammatory model in Normal Human Epidermal Keratinocyte cell lines ("NHEK") to measure the inhibition of inflammatory mediators such as IL-8 and TNF-α, as described in Example 22, or a TNF-alpha induced cytokine release model in Human Umbilical Vein Endothelial cell (HUVEC) cultures, as described in Example 23.

In some embodiments, described isoprenyl compounds are considered inhibitors of inflammation when they show a percent inhibition of inflammatory mediators, such as TNF-α, IL-β, IL-8/KC, and IL-6, in a P. acne-induced mouse ear inflammatory model of at least about 5, 10, 15, 20, 25, 30, 35, 40, 45, 50, 55, 60, 65, 70, 75, 80, 85, 90 or 95%, for example when provided at a dosage of 0.2 mg/20 µL. In some embodiments, described isoprenyl compounds are considered inhibitors of inflammation when they show a percent inhibition of cytokine release in a P. acne-induced mouse ear inflammatory model of at least about 5, 10, 15, 20, 25, 30, 35, 40, 45, 50, 55, 60, 65, 70, 75, 80, 85, 90 or 95%, for example when provided at a dosage of 0.4 mg/20 µL. In some embodiments, described isoprenyl compounds are considered inhibitors of inflammation when they show a percent inhibition of cytokine release in a P. acne-induced mouse ear inflammatory model of at least about 5, 10, 15, 20, 25, 30, 35, 40, 45, 50, 55, 60, 65, 70, 75, 80, 85, 90 or 95%, for example when provided at a dosage of 0.8 mg/20 µL.

In some embodiments, described isoprenyl compounds are considered inhibitors of inflammation when they show a percent inhibition of inflammatory mediators, such as IL-8, in a P. acnes-induced cytokine release inflammatory model in NHEK cell line of at least about 5, 10, 15, 20, 25, 30, 35, 40, 45, 50, 55, 60, 65, 70, 75, 80, 85, 90 or 95%, for example when provided at a dosage of at least about 0.001 µg/20 µL, 0.0025 µg/20 µL, 0.005 µg/20 µL, 0.0075 µg/20 µL, 0.01 µg/20 µL, 0.001 µg/20 µL, 0.025 µg/20 µL, 0.05 µg/20 µL, 0.075 µg/20 µL, 0.1 µg/20 µL, 0.25 µg/20 µL, 0.5 µg/20 µL, 0.75 µg/20 µL, 1 µg/20 µL, 10 µg/20 µL, 25 µg/20 µL, 50 µg/20 µL, 0.1 mg/20 µL, 0.2 mg/20 µL, 0.4 mg/20 µL, or 0.8 mg/20 µL.

In some embodiments, described isoprenyl compounds are considered inhibitors of inflammation when they show a percent inhibition of inflammatory mediators, such as IL-8, in a LPS-TLR4-induced cytokine release inflammatory model in HMEC-1 cell line of at least about 5, 10, 15, 20, 25, 30, 35, 40, 45, 50, 55, 60, 65, 70, 75, 80, 85, 90 or 95%, for example when provided at a dosage of 0.2 mg/20 µL. In some embodiments, described isoprenyl compounds are considered inhibitors of inflammation when they show a percent inhibition of inflammatory mediators, such as IL-8, in a LPS-TLR4-induced cytokine release inflammatory model in HMEC-1 cell line of at least about 5, 10, 15, 20, 25, 30, 35, 40, 45, 50, 55, 60, 65, 70, 75, 80, 85, 90 or 95%, for example when provided at a dosage of 0.4 mg/20 µL. In some embodiments, described isoprenyl compounds are considered inhibitors of inflammation when they show a percent inhibition of inflammatory mediators, such as IL-8, in a LPS-TLR4-induced cytokine release inflammatory model in HMEC-1 cell line of at least about 5, 10, 15, 20, 25, 30, 35, 40, 45, 50, 55, 60, 65, 70, 75, 80, 85, 90 or 95%, for example when provided at a dosage of 0.8 mg/20 µL.

In some embodiments, described isoprenyl compounds are considered inhibitors of inflammation when they show a percent inhibition of inflammatory mediators, such as IL-8, in a PGN-TLR2-induced cytokine release inflammatory model in NHEK cell line of at least about 5, 10, 15, 20, 25, 30, 35, 40, 45, 50, 55, 60, 65, 70, 75, 80, 85, 90 or 95%, for example when provided at a dosage of at least about 0.001 µg/20 µL, 0.0025 µg/20 jL, 0.005 µg/20 µL, 0.0075 µg/20 µL, 0.01 µg/20 µL, 0.001 µg/20 µL, 0.025 µg/20 µL, 0.05 µg/20 µL, 0.075 µg/20 µL, 0.1 µg/20 µL, 0.25 µg/20 µL, 0.5 µg/20 µL, 0.75 µg/20 µL, 1 µg/20 µL, 10 µg/20 µL, 25 µg/20 µL, 50 µg/20 µL, 0.1 mg/20 µL, 0.2 mg/20 µL, 0.4 mg/20 µL, or 0.8 mg/20 µL.

In some embodiments, described isoprenyl compounds are considered inhibitors of inflammation when they show a percent inhibition of inflammatory mediators, such as IL-8, MCP-1 and Groα, in an ATPγS-purinergic receptor-induced cytokine release inflammatory model in HMEC-1 cell line of at least about 5, 10, 15, 20, 25, 30, 35, 40, 45, 50, 55, 60, 65, 70, 75, 80, 85, 90 or 95%, for example when provided at a dosage of 0.2 mg/20 µL. In some embodiments, described isoprenyl compounds are considered inhibitors of inflammation when they show a percent inhibition of inflammatory mediators, such as such as IL-8, MCP-1 and Groα, in an ATPγS-purinergic receptor-induced cytokine release inflammatory model in HMEC-1 cell line of at least about 5, 10, 15, 20, 25, 30, 35, 40, 45, 50, 55, 60, 65, 70, 75, 80, 85, 90 or 95%, for example when provided at a dosage of 0.4 mg/20 µL. In some embodiments, described isoprenyl compounds are considered inhibitors of inflammation when they show a percent inhibition of inflammatory mediators, such as such as IL-8, MCP-1 and Groα, in an ATPγS-purinergic receptor-induced cytokine release inflammatory model in HMEC-1 cell line of at least about 5, 10, 15, 20, 25, 30, 35, 40, 45, 50, 55, 60, 65, 70, 75, 80, 85, 90 or 95%, for example when provided at a dosage of 0.8 mg/20 µL.

In some embodiments, described isoprenyl compounds are considered inhibitors of inflammation when they show a percent inhibition of inflammatory mediators, such as such as IL-8 and TNF-α, in a TPA-induced cytokine release inflammatory model in NHEK cell line of at least about 5, 10, 15, 20, 25, 30, 35, 40, 45, 50, 55, 60, 65, 70, 75, 80, 85, 90 or 95%, for example when provided at a dosage of 0.2 mg/20 μL. In some embodiments, described isoprenyl compounds are considered inhibitors of inflammation when they show a percent inhibition of inflammatory mediators, such as such as IL-8 and TNF-α, in a TPA-induced cytokine release inflammatory model in NHEK cell line of at least about 5, 10, 15, 20, 25, 30, 35, 40, 45, 50, 55, 60, 65, 70, 75, 80, 85, 90 or 95%, for example when provided at a dosage of 0.4 mg/20 μL. In some embodiments, described isoprenyl compounds are considered inhibitors of inflammation when they show a percent inhibition of inflammatory mediators, such as such as IL-8 and TNF-α, in a TPA-induced cytokine release inflammatory model in NHEK cell line of at least about 5, 10, 15, 20, 25, 30, 35, 40, 45, 50, 55, 60, 65, 70, 75, 80, 85, 90 or 95%, for example when provided at a dosage of 0.8 mg/20 μL.

In certain embodiments, described isoprenyl compounds are considered inhibitors of inflammation when they show a percent inhibition of cytokine release in a TNFα-induced cytokine release model, as determined using HUVEC cells of at least about 5, 10, 15, 20, 25, 30, 35, 40, 45, 50, 55, 60, 65, 70, 75, 80, 85, 90 or 95%, for example when provided at a dosage of 0.25%. In certain embodiments, described isoprenyl compounds are considered inhibitors of inflammation when they result in an $ED_{50}$ in a TNFα-induced cytokine release model, as determined using HUVEC cells, of at least about 0.01, 0.05, 0.10, 0.15, 0.20, 0.25, 0.30, 0.35 or 0.40 μg cytokine/mouse ear, for example when provided at a dosage of 0.25%. In certain embodiments, described isoprenyl compounds are considered inhibitors of inflammation when they show a percent inhibition of cytokine release in a TNFα-induced cytokine release model, as determined using HUVEC cells, of at least about 5, 10, 15, 20, 25, 30, 35, 40, 45, 50, 55, 60, 65, 70, 75, 80, 85, 90 or 95%, for example when provided at a dosage of 0.50%. In certain embodiments, described isoprenyl compounds are considered inhibitors of inflammation when they result in an $ED_{50}$ in a TNFα-induced cytokine release model, as determined using HUVEC cells, of at least about 0.01, 0.05, 0.10, 0.15, 0.20, 0.25, 0.30, 0.35 or 0.40 μg cytokine/mouse ear, for example when provided at a dosage of 0.50%. In certain embodiments, described isoprenyl compounds are considered inhibitors of inflammation when they show a percent inhibition of cytokine release in a TNFα-induced cytokine release model, as determined using HUVEC cells, of at least about 5, 10, 15, 20, 25, 30, 35, 40, 45, 50, 55, 60, 65, 70, 75, 80, 85, 90 or 95%, for example when provided at a dosage of 1.00%. In certain embodiments, described isoprenyl compounds are considered inhibitors of inflammation when they result in an $ED_{50}$ in a TNFα-induced cytokine release model, as determined using HUVEC cells, of at least about 0.01, 0.05, 0.10, 0.15, 0.20, 0.25, 0.30, 0.35 or 0.40 μg cytokine/mouse ear, for example when provided at a dosage of 1.00%.

In certain embodiments, described isoprenyl compounds are considered inhibitors of inflammation when they show a percent inhibition of cytokine release in a TPA-induced cytokine release model, as determined using NHEK cells of at least about 5, 10, 15, 20, 25, 30, 35, 40, 45, 50, 55, 60, 65, 70, 75, 80, 85, 90 or 95%, for example when provided at a dosage of 0.25%. In certain embodiments, described isoprenyl compounds are considered inhibitors of inflammation when they result in an $ED_{50}$ in a TPA-induced cytokine release model, as determined using NHEK cells, of at least about 0.01, 0.05, 0.10, 0.15, 0.20, 0.25, 0.30, 0.35 or 0.40 μg cytokine/mouse ear, for example when provided at a dosage of 0.25%. In certain embodiments, described isoprenyl compounds are considered inhibitors of inflammation when they show a percent inhibition of cytokine release in a TPA-induced cytokine release model, as determined using NHEK cells, of at least about 5, 10, 15, 20, 25, 30, 35, 40, 45, 50, 55, 60, 65, 70, 75, 80, 85, 90 or 95%, for example when provided at a dosage of 0.50%. In certain embodiments, described isoprenyl compounds are considered inhibitors of inflammation when they result in an $ED_{50}$ in a TPA-induced cytokine release model, as determined using NHEK cells, of at least about 0.01, 0.05, 0.10, 0.15, 0.20, 0.25, 0.30, 0.35 or 0.40 μg cytokine/mouse ear, for example when provided at a dosage of 0.50%. In certain embodiments, described isoprenyl compounds are considered inhibitors of inflammation when they show a percent inhibition of cytokine release in a TPA-induced cytokine release model, as determined using NHEK cells, of at least about 5, 10, 15, 20, 25, 30, 35, 40, 45, 50, 55, 60, 65, 70, 75, 80, 85, 90 or 95%, for example when provided at a dosage of 1.00%. In certain embodiments, described isoprenyl compounds are considered inhibitors of inflammation when they result in an $ED_{50}$ in a TPA-induced cytokine release model, as determined using NHEK cells, of at least about 0.01, 0.05, 0.10, 0.15, 0.20, 0.25, 0.30, 0.35 or 0.40 μg cytokine/mouse ear, for example, when provided at a dosage of 1.00%.

In certain embodiments, described isoprenyl compounds are considered inhibitors of inflammation when they show a percent inhibition of cytokine release in a TNFα-induced cytokine release model, as determined using HUVEC cells of at least about 5, 10, 15, 20, 25, 30, 35, 40, 45, 50, 55, 60, 65, 70, 75, 80, 85, 90 or 95%, for example when provided at a dosage of 0.25%. In certain embodiments, described isoprenyl compounds are considered inhibitors of inflammation when they result in an $ED_{50}$ in a TNFα-induced cytokine release model, as determined using HUVEC cells, of at least about 0.01, 0.05, 0.10, 0.15, 0.20, 0.25, 0.30, 0.35 or 0.40 μg cytokine/mouse ear, for example when provided at a dosage of 0.25%. In certain embodiments, described isoprenyl compounds are considered inhibitors of inflammation when they show a percent inhibition of cytokine release in a TNFα-induced cytokine release model, as determined using HUVEC cells, of at least about 5, 10, 15, 20, 25, 30, 35, 40, 45, 50, 55, 60, 65, 70, 75, 80, 85, 90 or 95%, for example when provided at a dosage of 0.50%. In certain embodiments, described isoprenyl compounds are considered inhibitors of inflammation when they result in an $ED_{50}$ in a TNFα-induced cytokine release model, as determined using HUVEC cells, of at least about 0.01, 0.05, 0.10, 0.15, 0.20, 0.25, 0.30, 0.35 or 0.40 μg cytokine/mouse ear, for example when provided at a dosage of 0.50%. In certain embodiments, described isoprenyl compounds are considered inhibitors of inflammation when they show a percent inhibition of cytokine release in a TNFα-induced cytokine release model, as determined using HUVEC cells, of at least about 5, 10, 15, 20, 25, 30, 35, 40, 45, 50, 55, 60, 65, 70, 75, 80, 85, 90 or 95%, for example when provided at a dosage of 1.00%. In certain embodiments, described isoprenyl compounds are considered inhibitors of inflammation when they result in an $ED_{50}$ in a TNFα-induced cytokine release model, as determined using HUVEC cells, of at least about 0.01, 0.05, 0.10, 0.15, 0.20, 0.25, 0.30, 0.35 or 0.40 µg cytokine/mouse ear, for example when provided at a dosage of 1.00%.

Dosages of a described isoprenyl compound utilized in accordance with the present invention may vary with the form of administration and/or with the particular subject being treated. In general, a described isoprenyl compound is most desirably administered at a concentration level that will afford effective results without causing any harmful or deleterious side-effects. In some embodiments, a described isoprenyl compound is administered in doses ranging from about 0.5 to about 500 mg/kg/day. In some embodiments, a described isoprenyl compound is administered in doses ranging from about 5 to about 100 mg/kg/day. In some embodiments, a described isoprenyl compound is administered in doses ranging from about 10 to about 100 mg/kg/day. In some embodiments, a described isoprenyl compound is administered in doses ranging from about 20 to about 100 mg/kg/day. In some embodiments, a described isoprenyl compound is administered in doses ranging from about 30 to about 100 mg/kg/day. In some embodiments, a described isoprenyl compound is administered in doses ranging from about 40 to about 100 mg/kg/day. In some embodiments, a described isoprenyl compound is administered in doses ranging from about 50 to about 100 mg/kg/day. In some embodiments, a described isoprenyl compound is administered in doses ranging from about 60 to about 100 mg/kg/day. In some embodiments, a described isoprenyl compound is administered in doses ranging from about 70 to about 100 mg/kg/day. In some embodiments, a described isoprenyl compound is administered in doses ranging from about 80 to about 100 mg/kg/day. In some embodiments, a described isoprenyl compound is administered in doses ranging from about 90 to about 100 mg/kg/day. In some embodiments, a described isoprenyl compound is administered in doses of less than about 20 mg/day. In some embodiments, a described isoprenyl compound is administered in doses ranging from about 1 mg/kg/day to about 50 mg/kg/day. In some embodiments, a described isoprenyl compound is administered in doses ranging from about 1 mg/kg/day to about 40 mg/kg/day. In some embodiments, a described isoprenyl compound is administered in doses ranging from about 1 mg/kg to about 30 mg/kg/day. In some embodiments, a described isoprenyl compound is administered in doses ranging from about 1 mg/kg/day to about 20 mg/kg/day. In some embodiments, a described isoprenyl compound is administered in doses ranging from about 1 mg/kg/day to about 10 mg/kg/day. In some embodiments, a described isoprenyl compound is administered in doses ranging from about 10 mg/kg/day to about 50 mg/kg/day. In some embodiments, a described isoprenyl compound is administered in doses ranging from about 10 mg/kg/day to about 40 mg/k/day. In some embodiments, a described isoprenyl compound is administered in doses ranging from about 10 mg/kg/day to about 30 mg/kg/day. In some embodiments, a described isoprenyl compound is administered in doses ranging from about 10 mg/kg/day to about 20 mg/kg/day. In some embodiments, a described isoprenyl compound is administered in doses ranging from about 20 mg/kg/day to about 50 mg/kg/day. In some embodiments, a described isoprenyl compound is administered in doses ranging from about 20 mg/kg/day to about 40 mg/kg/day. In some embodiments, a described isoprenyl compound is administered in doses ranging from about 20 mg/kg/day to about 30 mg/kg/day. In some embodiments, a described isoprenyl compound is administered in doses ranging about 25 mg/kg/day to about 50 mg/kg/day. In some embodiments, a described isoprenyl compound is administered in doses ranging about 30 mg/kg/day to about 50 mg/kg/day. In some embodiments, a described isoprenyl compound is administered in doses ranging from about 30 mg/kg/day to about 40 mg/kg/day. In some embodiments, a described isoprenyl compound is administered in doses ranging from about 40 mg/kg/day to about 50 mg/kg/day. In some embodiments, a described isoprenyl compound is administered in doses less than about 10 mg/kg/day. In some embodiments, a described isoprenyl compound is administered in doses less than about 5 mg/kg/day. In some embodiments, a described isoprenyl compound is administered in doses less than about 2 mg/kg/day. In some embodiments, a described isoprenyl compound is administered in doses less than about 1 mg/kg/day. In some embodiments, a described isoprenyl compound is administered in doses less than about 0.1 mg/kg/day. In some embodiments, a described isoprenyl compound is administered in doses less than about 0.01 mg/kg/day. In some embodiments, a described isoprenyl compound is administered in doses less than about 0.001 mg/kg/day. In some embodiments, a described isoprenyl compound is administered in doses of about 0.1, 0.2, 0.3, 0.4, 0.5, 0.6, 0.7, 0.8, 0.9, or 1.0 mg/kg/day. In some embodiments, a described isoprenyl compound is administered in doses of about 0.01, 0.02, 0.03, 0.04, 0.05, 0.06, 0.07, 0.08, or 0.09 mg/kg/day. In some embodiments, a described isoprenyl compound is administered in doses ranging from about 0.1 mg/kg/day to about 1 mg/kg/day. In some embodiments, a described isoprenyl compound is administered in doses ranging from about 0.01 mg/kg/day to about 0.1 mg/kg/day. In some embodiments, a described isoprenyl compound is administered in doses ranging from about 0.001 mg/kg/day to about 0.01 mg/kg/day.

Topical dosages of a described isoprenyl compound utilized in accordance with the present invention may vary with the form of administration and/or with the particular subject being treated. In general, a described isoprenyl compound is most desirably topically administered at a concentration level that will afford effective results without causing any harmful or deleterious side-effects. In some embodiments, a described isoprenyl compound is administered in topical doses ranging from about 0.25 to about 25 mg/cm$^2$ per application. In some embodiments, a described isoprenyl compound is administered in doses ranging from about 1 to about 10 mg/cm$^2$ per application. In some embodiments, a described isoprenyl compound is administered in topical doses ranging from about 2.5 to about 5 mg/cm$^2$ per application. In some embodiments, a described isoprenyl compound is administered in doses ranging from about 5 to about 25 mg/cm$^2$ per application. In some embodiments, application frequency of a described isoprenyl compound ranges from occasional (<once a week) to four times daily. In some embodiments, application frequency of a described isoprenyl compound is once or twice daily.

The efficacy of described isoprenyl compounds in the treatment, prevention, and/or management of symptoms of diseases, disorders, and/or conditions according to the present invention may be evaluated and followed using any method known in the medical arts. In some embodiments, described isoprenyl compounds are used in the treatment of symptoms associated with skin conditions and may be evaluated using any methods known to those of skill in the dermatological arts. Exemplary such methods include, for example, physical examination, subject evaluations, photography, and dermospectrophotometer readings, etc., as described herein in Example 24.

Methods of Synthesis

Described isoprenyl compounds may be prepared or synthesized according to methods known in the art, disclosed in one or more of U.S. Pat. Nos. 5,043,268, 5,202,456, 5,705,528, United States Patent Publication No. 2005/0277694, United States Patent Publication No. 2007/0004803, United States Patent Publication No. 2009/0155186, United States Patent Publication No. 2009/0170917, World Publication No. WO 2009/102997, and U.S. patent application Ser. No. 12/616,781, the disclosures of which are incorporated by reference herein. As will be appreciated by one of skill in the art, the synthetic methods as described may be modified without departing from the scope of the present invention. For example, different starting materials and/or different reagents may be used in the inventive synthetic methods.

Compositions

The present invention provides compositions comprising isoprenyl compounds as described herein. In some embodiments, provided compositions contain additional components. In some embodiments, all such additional components are pharmaceutically acceptable and provided compositions are pharmaceutical compositions. In some embodiments, all such additional components are cosmetically acceptable and provided compositions are cosmetic compositions. In some embodiments, all such additional components are cosmeceutically acceptable and provided compositions are cosmeceutical compositions.

In some embodiments, pharmaceutical, cosmetic or cosmeceutical compositions of the present invention comprise one or more isoprenyl compounds, a pharmaceutically acceptable inert ingredient (e.g., a carrier) and optionally an additional active ingredient. In certain embodiments, the isoprenyl compound is a compound of Formulae Ia, Ib, Ic, Id, Ie or If and/or II. In certain embodiments, the isoprenyl compound is a compound of Formulae Ia, Ib, Ic, Id, Ie or If and/or II.

In general, one or more compounds of the present invention may be formulated into pharmaceutical compositions comprising at least one described isoprenyl compound together with one or more pharmaceutically acceptable carriers, including excipients, such as diluents, binders and the like, and additives, such as stabilizing agents, preservatives, solubilizing agents, and buffers, as desired. Formulation excipients may include, for instance, polyvinylpyrrolidone, gelatin, hydroxy cellulose, acacia, polyethylene glycol, manniton, sodium chloride and sodium citrate. In some embodiments, compositions comprising one or more of a described isoprenyl compound contain a pharmaceutically acceptable carrier. In some embodiments, the compositions comprising one or more of a described isoprenyl compound include a cosmetically acceptable carrier. In some embodiments, compositions comprising one or more of a described isoprenyl compound include a cosmeceutically acceptable carrier.

Pharmaceutical carriers are typically of sufficiently high purity and sufficiently low toxicity to render the one or more carriers suitable for administration to the subject being treated. Pharmaceutical carriers further maintain stability and bioavailability of an active agent (e.g., a described isoprenyl compound). Pharmaceutical carriers can be liquid or solid and are selected with the planned manner of administration in mind, to provide for the desired bulk, consistency, etc., when combined with an active agent and/or other components of a given composition.

A carrier in certain compositions according to the present invention may include liquid and, in particular may comprise a buffered, isotonic, aqueous solution.

A carrier, including a pharmaceutically acceptable carrier, may be, or include, an excipient, such as a diluent, binder (e.g., binding agent) and the like, and or an additive, such as a stabilizing agent, preservative, solubilizing agent, and/or buffer as hereafter described. Pharmaceutical carriers include, without limitation, a binding agent (e.g., hydroxypropyl methylcellulose, polyvinylpyrrolidone, or pregelatinised maize starch, etc.); a filler (e.g., calcium hydrogen phosphate calcium sulfate, ethyl cellulose, gelatin, lactose and other sugars, microcrystalline cellulose, pectin, polyacrylates, etc.); a disintegrant (e.g., glycolate, sodium starch, starch, etc.); a lubricant (e.g., colloidal silicon dioxide, corn starch, hydrogenated vegetable oils, polyethylene glycols, magnesium stearate, metallic stearates, silica, sodium benzoate, sodium acetate, stearic acid, talc, etc.); or a wetting agent (e.g., sodium lauryl sulphate, etc.). Additional pharmaceutically acceptable carriers include, for example, petroleum jelly (Vaseline™), and petroleum.

Additional suitable carriers for the compositions of the present invention include, but are not limited to, alcohols, amyloses, animal oil, anti-irritants, chelating agents, colorants, deodorant agents, emulsifiers, fragrances, gelatins, hair conditioning agents, hydroxymethylcelluloses, magnesium stearates moisturizing agents (e.g., humectants), microcrystalline, mineral oil, natural polymers (e.g., collagen, gum arabic, polyols, and xanthanes, and the like), organic, ozocerite wax, and inorganic waxes, paraffin, penetration enhancers, pH adjusting agents, preservatives, propellants, salt solutions, silicic acids, surfactants talcs, solubilizing agents, thickeners, viscous paraffins, and water, and combinations thereof. In some embodiments, isoprenyl compounds of the present invention act as acceptable carrier(s) and/or excipient(s). In cerain embodiments, isoprenyl acts as an acceptable carrier and/or excipient. In some embodiments, it may be desirable to use the carriers in cosmetic compositions, as described in the CTFA International Cosmetic Ingredient Dictionary and Handbook, 8th edition, edited by Wenninger and Canterbery, (The Cosmetic, Toiletry, and Fragrance Association, Inc., Washington, D.C., 2000), which is herein incorporated by reference. Also included are the carriers described hereinabove.

In some embodiments, pharmaceutically acceptable carriers of the composition include a sustained release or delayed release carrier. Such carriers can be any material capable of sustained or delayed release of described isoprenyl compounds to provide a more efficient administration resulting in less frequent and/or decreased dosage of provided isoprenyl compounds, ease of handling, and extended or delayed effects on diseases, disorders, conditions, syndromes, and the like, being treated, prevented or promoted. Non-limiting examples of such carriers include liposomes, microsponges, microspheres, or microcapsules of natural and synthetic polymers and the like. Liposomes which may enhance the localized delivery of the one or more provided isoprenyl compounds within skin layers, may be formed from a variety of phospholipids, such as cholesterol, stearylamines or phosphatidylcholines.

For injection or other liquid administration formulations, water containing at least one or more buffering constituents is commonly utilized, and stabilizing agents, preservatives and solubilizing agents may also be employed. In some embodiments, a provided pharmaceutical composition is or comprises an isotonic solution.

For solid administration formulations, any of a variety of thickening, filler, bulking and carrier additives may be employed, such as starches, sugars, fatty acids and the like. Topical compositions of the present invention can be applied locally to the skin or mucosa and may be in any form including solutions, oils, creams, ointments, gels, lotions, shampoos, milks, cleansers, moisturizers, sprays, skin patches and the like.

For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a described compound over a period of time. For example, gelatin, sodium carboxymethylcellulose and/or other cellulosic excipients may be included to provide time-release or slower-release formulations, especially for administration by subcutaneous and intramuscular injection.

In practical use, described isoprenyl compounds can be combined as the active ingredient(s) in an admixture with a pharmaceutical carrier according to conventional pharmaceutical compounding techniques. Pharmaceutical compositions of the present invention may be formulated for delivery by any of a variety of routes including, for example, oral, parenteral (including intravenous), urethral, vaginal, nasal, topical (e.g., dermal, transdermal), pulmonary, deep lung, inhalation, buccal, sublingual routes, or the like.

In preparing compositions containing one or more described isoprenyl compounds for cutaneous administration, such as topical (i.e., local), such compositions can include pharmaceutical carriers (e.g., sterile and non-sterile aqueous solutions, non-aqueous solutions in common solvents such as alcohols, or solutions of described isoprenyl compounds in liquid or solid oil bases). Such pharmaceutical carrier solutions also can contain buffers, diluents and other suitable additives.

In preparing compositions containing described isoprenyl compounds for parenteral administration (e.g., intramuscular or subcutaneous administration), such compositions can include pharmaceutical carriers (e.g., sterile and non-sterile aqueous solutions, non-aqueous solutions in common solvents such as alcohols, or solutions of described isoprenyl compounds in liquid or solid oil bases). Such pharmaceutical carrier solutions also can contain buffers, diluents and other suitable additives.

Representative compositions suitable for oral use include, for example, mouthwash, rinse, oral spray, suspension, dental gel, and the like. Typical oral carriers known in the art may be used in the present invention. Exemplary pharmaceutical and/or cosmetic carriers are water, ethanol, and water-ethanol mixtures. The water-ethanol mixtures are generally employed in a weight ratio from about 1:1 to about 20:1, preferably from about 3:1 to about 20:1, and most preferably from about 3:1 to about 10:1, respectively. The pH value of the oral vehicle is generally from about 4 to about 7, and preferably from about 5 to about 6.5. An oral topical vehicle having a pH value below about 4 is generally irritating to the oral cavity and an oral vehicle having a pH value greater than about 7 generally results in an unpleasant mouth feel.

Oral topical compositions comprising one or more described isoprenyl compounds may also contain conventional additives normally employed in those products. Conventional additives as desribed herein include a coloring agents, emulsifiers, fluorine providing compounds, humectants, sweetening agents, and pH adjusting agents, provided that such additives do not interfere with the therapeutic, cosmetically, or cosmeceutically beneficial properties of compositions comprising one or more described isoprenyl compounds. Additional ingredients that may be used in compositions of the present invention include fluorine providing compounds, additional active ingredients, new excipients, protectives, and demulcents, as described herein.

Fluorine providing compounds may be fully or slightly water soluble and are characterized by their ability to release fluoride ions or fluoride containing ions in water and by their lack of reaction with other components in the composition. Typical fluorine providing compounds include alkali metal fluorides, inorganic fluoride salts such as water-soluble alkali metal, alkaline earth metal, heavy metal salts, for example, aluminum mono- and di-fluorophosphates, ammonium fluoride, ammonium fluorosilicate, barium fluoride, cuprous fluoride, fluorinated sodium calcium pyrophosphate, potassium fluoride, sodium fluoride, sodium fluorosilicate, sodium fluorozirconate, sodium monofluorophosphate, stannic fluoride, stannous fluoride and zinc fluoride, monofluorophosphates, such as sodium and stannous fluoride, sodium monofluorophosphate, tin fluoride and combinations thereof.

Amounts of fluorine providing compounds present in oral, topical inventive compositions provided herein depend upon the type of fluorine providing compound employed, solubility of the fluorine compound, and the nature of the final oral inventive composition. Amount of fluorine providing compounds used must be a nontoxic amount. In general, fluorine providing compounds when used will be present in an amount up to about 1%, from about 0.001% to about 0.1%, and rom about 0.001% to about 0.05%, by weight of oral topical inventive compositions provided herein.

Typical sweetening agents (sweeteners) that are well known in the art include those that are both natural and artificial sweeteners, may be employed. Sweetening agent used may be selected from a wide range of materials including water-soluble sweetening agents, water-soluble artificial sweetening agents, water-soluble sweetening agents derived from naturally occurring water-soluble sweetening agents, dipeptide based sweetening agents, and protein based sweetening agents, including mixtures thereof.

In some embodiments, compositions of the present invention can further include one or more additional ("compatible", as defined herein) active ingredients which are aimed at providing compositions with another pharmaceutical, cosmetic, or cosmeceutical effect, in addition to that provided by an isoprenyl compound of compositions provided herein.

Additional active ingredients according to the present invention include, without limitation, one or more, in any combination, of a protective agent, an emollient, an astringent, an irritant, a keratolytic, a sun screening agent, a sun tanning agent, an antibiotic agent, an antifungal agent, an antiviral agent, an antiprotozoal agent, an anesthetic agent, a steroidal anti-inflammatory agent, a non-steroidal anti-inflammatory agent, an antipruritic agent, an anti-oxidant agent, a chemotherapeutic agent, an anti-histamine agent, a vitamin, a hormone, an anti-dandruff agent, an anti-wrinkle agent, an anti-skin atrophy agent, a sclerosing agent, a cleansing agent, a caustic agent and a hypo-pigmenting agent.

In some embodiments, at least one described isoprenyl compound of compositions provided herein is an active ingredient.

Compositions according to the present invention, which further include one or more additional active ingredients, can therefore be further efficiently used, in addition to their use as a treatment for an epithelial-related condition, in the treatment of any medical, cosmetic and/or cosmeceutical condition in which applying the additional active ingredient is beneficial.

Protectives as described herein may take the form of dusting powders, adsorbents, mechanical protective agents, and plasters. Dusting powders are relatively inert and insoluble materials that are used to cover and protect epithelial surfaces, ulcers and wounds. Usually, these substances are finely subdivided powders that absorb moisture and can act as a dessicant. The absorption of skin moisture decreases friction and also discourages certain bacterial growth. Some of the materials used as protective adsorbents include bentonite, insoluble salts of bismuth, boric acid, calcium carbonate, (precipitated), cellulose, corn starch, magnesium stearate, talc, titanium dioxide, zinc oxide, and zinc stearate.

In some embodiments, protectives also can be administered to the skin to form an adherent, continuous film that may be flexible or semi-rigid depending on the materials and the formulations as well as the manner in which they are applied. This material may serve several purposes including providing occlusion from the external environment, providing chemical support, and serving as vehicles for other medicaments.

In some embodiments, protectives included in compositions of the present invention are demulcents. Demulcents often are applied to the surface in a viscid, sticky preparation that covers the area readily and may be medicated. A number of chemical substances possess demulcent properties.

In practical use, described isoprenyl compounds herein can be combined as an active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, dermal, transdermal, pulmonary, deep lung, inhalation, buccal, sublingual, or the like.

In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets. Tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and/or a sweetening agent such as sucrose, lactose or saccharin. Capsules may contain, in addition to materials of the above type, a liquid carrier such as a fatty oil.

In some embodiments, a described isoprenyl compound, carrier and, optionally, additional active ingredients are formed into a composition in the form of a solution, emulsion or gel suspension, as will be further described herein.

In some embodiments, a described isoprenyl compound, a pharmaceutical or cosmetic carrier and, optionally, one or more additional active ingredients, are in the form of a solution. A solution can be prepared by mixing a solute or dissolved substance (such as a described isoprenyl compound of the invention and, optionally, one or more active ingredient(s)) uniformly throughout a solvent carrier such as water or organic solvents, such as the alcohols (e.g. ethanol or isopropanol, acetone).

In some embodiments, the solution is an aqueous solution wherein a described isoprenyl compound may be appropriately buffered by means of saline, acetate, phosphate, citrate, acetate or other buffering agents, which may be at any physiologically acceptable pH, generally from about pH 4 to about pH 7. Combinations of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, suitable preservatives may be employed, to prevent or limit bacteria and other microbial growth. One such preservative that may be employed is 0.05% benzalkonium chloride.

In some embodiments, inventive compositions comprising a described isoprenyl compound, a carrier and other, optional ingredients are provided in the form of an emulsion. Emulsions are a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of two phases will not occur unless a third substance, an emulsifying agent, is incorporated. Thus, a basic emulsion in the context of the present invention typically contains two or more components (e.g., two immiscible liquid carriers, an emulsifying agent, and one or more described isoprenyl compounds). In some embodiments a isoprenyl compound can be an emulsifying agent. Typically, emulsions incorporate an aqueous phase into a non-aqueous phase (or vice versa). However, it is possible to prepare emulsions that are largely non-aqueous, for example, anionic and cationic surfactants of the non-aqueous immiscible system glycerin and olive oil. Exemplary emulsifying agents are described herein.

In some embodiments compositions of the present invention comprise an emulsion including AFC. In some embodiments, non-lipid-based vehicles are useful in an emulsion comprising AFC due to the lipophilic nature of AFC.

In some embodiments, inventive compositions comprising one or more described isoprenyl compounds, are provided in the form of gel suspensions, (a semi-solid carrier) or solid carrier to form a paste, powder, ointment, cream, lotion, hydrogel or the like. Exemplary ointments that may be prepared as a gel-suspension include semi-solid preparations intended for external application to the epithelium. Generally, ointment bases are categorized into hydrocarbon bases (oleaginous), which may use white petroleum as a base; adsorption bases (anhydrous), which might use hydrophilic petroleum or anhydrous lanolin; emulsion bases (water and oil type); emulsion bases (oil and water type); and water soluble bases, which often use polyethylene glycol as an ointment base.

Additional compositions comprising one or more of a described isoprenyl compound can be readily prepared using technology known in the art as described in Remington's Pharmaceutical Sciences, $18^{th}$ or $19^{th}$ editions, published by the Mack Publishing Company of Easton, Pa.

It is also possible and contemplated herein that described isoprenyl compounds may be in a dried and particulate form. In certain embodiments, particles are between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, described isoprenyl compounds may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Exemplary devices include dry powder inhalers, designed to form a cloud or aerosol of fine powder with a particle size that is always less than about 6.0 μm.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

In some embodiments, described isoprenyl compounds may be therapeutically administered by means of an injection, typically a deep intramuscular injection, such as in the gluteal or deltoid muscle, of a time release injectable formulation. In some embodiments, described isoprenyl compounds are formulated with a PEG, such as poly(ethylene glycol) 3350, and optionally one or more additional excipients and preservatives, including but not limited to excipients such as salts, polysorbate 80, sodium hydroxide or hydrochloric acid to adjust pH, and the like. In some embodiments, a described compound of the present invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer (PLGA polymer) is employed, preferably a PLGA polymer with a hydrophilic end group, such as PLGA RG502H from Boehringer Ingelheim, Inc. (Ingelheim, Germany).

Such formulations may be made, for example, by combining a described one or more described isoprenyl compounds in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which are preferably also adhesive polymers, may be employed in a time release injectable formulation. The teachings of U.S. Pat. Nos. 4,938,763, 6,432,438, and 6,673,767, and the biodegradable polymers and methods of formulation disclosed therein, are incorporated herein by reference. The formulation may be such that an injection is required on a weekly, monthly or other periodic basis, depending on the concentration and amount of a described compound, the biodegradation rate of the polymer, and other factors known to those of skill in the art.

In some embodiments, compositions comprising one or more described isoprenyl compounds are formulated as aqueous suspensions wherein the one or more described isoprenyl compound is in admixture with excipients additives and/or suitable for the manufacture of aqueous suspensions. Such additives and/or excipients are suspending agents, for example, sodium carboxymethylcellulose, methylcellulose, hydroxy propylmethylcellulose, sodium alginate, polyvinylpyrrolidone, gum tragacanth, and gum acacia; dispersing or wetting agents may be a naturally occurring phosphatide such as lecithin, or condensation products of an alkylene oxide with fatty acids, for example, polyoxyethylene stearate, or condensation products of ethylene oxide with long chain aliphatic alcohols, for example, heptadecaethyl eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Aqueous suspensions also may contain one or more coloring agents, one or more flavoring agents, and one or more sweetening agents, such as sucrose or saccharin.

In some embodiments, compositions comprising one or more described isoprenyl compounds are formulated as oily suspensions by suspending the one or more described isoprenyl compound in a vegetable oil (e.g., arachis oil, olive oil, sesame oil, coconut oil, or a mineral oil, such as liquid paraffin). Oily suspensions may contain a thickening agent (e.g., beeswax, hard paraffin or cetyl alcohol). Sweetening agents, such as those described herein, and flavoring agents may be added to provide a palatable oral composition. Such compositions may be preserved by the addition of an anti-oxidant (e.g., ascorbic acid).

In some embodiments, compositions comprising one or more described isoprenyl compounds are formulated as dispersible powders and/or granules are suitable for compositions of an aqueous suspension by adding water. One or more described isoprenyl compounds formulated in such dispersible powders and/or granules are provided in admixture with a dispersing or wetting agent, suspending agent, and one or more preservatives. Suitable dispersing or wetting agents and suspending agents are exemplified by those already mentioned herein. Additional excipients, for example, sweetening, flavoring and coloring agents also may be present.

Compositions of the invention also may be in the form of oil in water emulsions. The oily phase may be a vegetable oil, for example, olive oil or arachis oil, or a mineral oil, for example a liquid paraffin, or a mixture thereof. Suitable emulsifying agents may be naturally occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate. The emulsions also may contain sweetening and flavoring agents.

Compositions of the invention also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

Combination Therapy

In some embodiments of the present invention, the one or more described isoprenyl compound is administered in combination with one or more other therapeutically active agents. In some embodiments, active agents administered in combination are administered as part of a single composition; in some embodiments, active agents administered in combination are administered as separate compositions.

To give but a few examples, in some embodiments, different inventive complexes are administered in combination.

In some embodiments, described isoprenyl compounds are administered together with one or more other anti-inflammatory agents. Representative such anti-inflammatory agents include, for example, NSAIDs such as Acetominaphen (Tylenol), Aspirin, Celecoxib (Celebrex), Diclofenac (Voltaren), Diflunisal (Dolobid), Etodolac (Lodine), Ibuprofen (Motrin), Indomethacin (Indocin), Ketoprofen (Orudis), Ketorolac (Toradol), Nabumetone (Relafen), Naproxen (Aleve, Naprosyn), Oxaprozin (Daypro), Piroxicam (Feldene), Salsalate (Amigesic), Sulindac (Clinoril), Tolmetin (Tolectin), salicylic acid; and/or steroids such as glucocorticoids, for example, clobetasol (Clobex or Olux), dexamethasone, cortisol, testoterone, estrogen, estradiol, progesterone, etc In some embodiments, described isoprenyl compounds are administered together with one or more pain-relieving agents. Representative such pain relieving agents include, for example, NSAIDs such as Acetominaphen (Tylenol), Aspirin, Celecoxib (Celebrex), Diclofenac (Voltaren), Diflunisal (Dolobid), Etodolac (Lodine), Ibuprofen (Motrin), Indomethacin (Indocin), Ketoprofen (Orudis), Ketorolac (Toradol), Nabumetone (Relafen), Naproxen (Aleve, Naprosyn), Oxaprozin (Daypro), Piroxicam (Feldene), Salsalate (Amigesic), Sulindac (Clinoril), Tolmetin (Tolectin); and/or steroids such as glucocorticoids, for example, clobetasol (Clobex or Olux), dexamethasone, cortisol, testoterone, estrogen, estradiol, progesterone, etc. Alternatively or additionally, representative pain-relieving agents include, for example, articaine, benzocaine, bupivacaine, carticaine, chloroprocaine, cinchocaine/dibucaine, cocaine, cyclomethycaine, dimethyocaine/larocaine, etidocaine, levobupivacaine, lidocaine/lignocaine, mepvacaine, piperocaine, prilocaine, propoxycaine, procaine/novocaine, proparacaine, ropivacaine, saxitoxin, tetracaine/amethocaine, trimecaine, and/or combinations thereof.

In some embodiments, described isoprenyl compounds are administered together with glucocortocoids, aspirin, diclofenac, lidocaine, etc., and/or combinations thereof.

In some embodiments, described isoprenyl compounds are administered together with one or more other anti-bacterial agents. Representative such anti-bacterial agents include antibiotic agents such as penicillins, cephalosporins, carbacephems, cephamycins, carbapenems, monobactams, aminoglycosides, glycopeptides, quinolones, tetracyclines, macrolides, sulfonamides, fluoroquinolones, and lincosamides; and other anti-bacterial agents such as benzoyl peroxide and sulfur.

In some embodiments, described isoprenyl compounds are administered together with one or more keratolytic agents. Representative keratolytic agents include benzoyl peroxide, fluorouracil, resorcinol, salicylic acid, tretinoin, and the like.

EXAMPLES

Described isoprenyl compounds as provided by the present invention may be prepared by any method known if the art. Non-limiting examples for preparing inventive complexes are illustrated below.

Described isoprenyl compounds may be prepared or synthesized according to methods known in the art. To give but some examples, described isoprenyl compounds may be prepared or synthesized by methods disclosed in one or more of U.S. Pat. Nos. 5,043,268, 5,202,456, 5,705,528, United States Patent Publication No. 2005/0277694, United States Patent Publication No. 2007/0004803, United States Patent Publication No. 2009/0155186, United States Patent Publication No. 2009/0170917, World Publication No. WO 2009/102997, and U.S. patent application Ser. No. 12/616,781, the disclosures of which are incorporated by reference herein.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all classes, subclasses and species of each of these compounds, disclosed herein.

The described isoprenyl compounds, including S-trans, trans-farnesyl-L-cysteine, utilized as starting materials may be synthesized according to methods known in the art or synthesized by the methods disclosed in Brown et al., *J Am Chem Soc,* 1991, 113: 3176-3177, the disclosure of which is incorporated by reference herein. Other starting materials such as S-trans, trans-farnesyl-L-cysteine methyl ester, may be synthesized according to methods known in the art or synthesized by the methods disclosed in Troutman et al., *Bioconjugate Chem,* 2005, 16: 1209-1217.

The following general experimental procedures were used for Examples 1-9 as described below. Proton Nuclear Magnetic Resonance ($^1$H-NMR) spectroscopy was recorded on a Bruker 500 MHz spectrometer, dimethyl sulfoxide (DMSO-d6), methanol (CD$_3$OD) or chloroform (CDCl$_3$) was used as $^1$H-NMR solvent. The residual proton absorption of the deuterated solvent was used as the internal standard. All $^1$H-NMR chemical shift are reported as δ values in the parts per million (ppm). The splitting pattern abbreviations are as follows: s, singlet; d, doublet; t, triplet; q, quartet; br, broad; m, multiplet; dd, doublet of doublet; dt, doublet of triplets. The HPLC analysis was done using a phenomenex luna Cis(2)50×4.6 mm column. The mobile phase is 60% water, 40% acetonitrile containing 0.05% trifluoroacetic acid at 2 mL per minute flow rate for the first 2.5 minutes, followed by a gradient to 100% acetonitrile containing 0.05% TFA over 10 minutes. The eluent is observed at 214 nm.

Example 1

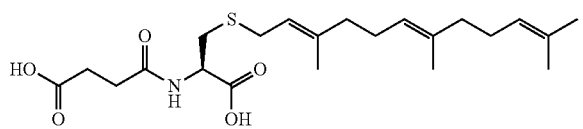 [SMILES: CC(C)=CCC/C(C)=C/CC/C(C)=C/CSC[C@H](NC(=O)CCC(=O)O)C(=O)O]

Synthesis of (4-((R)-1-carboxy-2-((2E,6E)-3,7,11-trimethyldodeca-2,6,10-trienylthio)ethylamino)-4-oxobutanoic acid) (Compound B)

To a solution of S-trans, trans-farnesyl-L-cysteine (500 mg, 1.54 mmol) in THF, a first portion of $K_2CO_3$ (2 mmol) was added and the resultant solution was cooled to 5° C. with vigorous stirring. To this stirred solution was added succinic anhydride (308 mg, 3.1 mmol) dropwise while maintaining the pH at 9.0-10.0 with another portion of $K_2CO_3$ (4 mmol). The mixture was stirred at room temperature for 2 h, HPLC analysis showed completion of the reaction. The pH of the reaction mixture then adjusted to 2.0 by the addition of 2 N HCl solution. The acidic solution was extracted three times with 10 mL of ethyl acetate. The combined organic extract was washed with water, brine and dried over $Na_2SO_4$, the solvent was removed on rotary evaporator to afford crude Compound B, which was further purified by preparative HPLC (535 mg, 82%) to yield Compound B. $^1$H-NMR (500 MHz, $CDCl_3$): δ 1.59 (s, 6H), 1.66 (s, 6H), 2.05 (m, 8H), 2.60 (m, 2H), 2.48 (m, 2H), 2.86 (dd, 1H), 2.94 (dd, 1H), 3.10 (dd, 1H), 3.12 (dd, 1H), 4.68 (dd, 1H), 5.06 (m, 2H), 5.20 (t, 1H). $^{13}$C-NMR (125 MHz, $CDCl_3$): δ 16.0, 16.1, 17.7, 25.7, 26.5, 26.7, 29.4, 29.8, 30.5, 32.6, 39.6, 39.7, 52.2, 119.3, 123.8, 124.3, 131.3, 135.4, 140.3, 173.4, 174.2, 176.8; ES-MS: mass calcd for Chemical Formula: $C_{22}H_{35}NO_5S$, 425.6. Found (M+Na) m/z 448.

Example 2

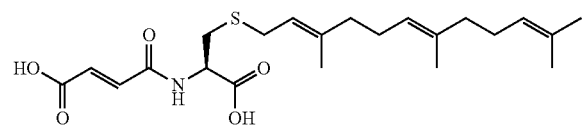 [SMILES: CC(C)=CCC/C(C)=C/CC/C(C)=C/CSC[C@H](NC(=O)/C=C/C(=O)O)C(=O)O]

Synthesis of ((E)-4-((R)-1-carboxy-2-((2E,6E)-3,7,11-trimethyldodeca-2,6,10-trienylthio)ethylamino)-4-oxobut-2-enoic acid) (Compound A)

A solution of S-trans, trans-farnesyl-L-cysteine (500 mg, 1.54 mmol) in THF and a first portion of $K_2CO_3$ (3 mmol) was cooled to 5° C. with vigorous stirring. To this stirred solution was added maleic anhydride (302 mg, 3.07 mmol) portionwise while maintaining the pH at 9.0-10.0 with another portion of $K_2CO_3$ (3 mmol). The mixture was stirred at room temperature for 3 h, HPLC analysis showed completion of the reaction. The pH of the reaction mixture then adjusted to 2.0 by the addition of 2 N HCl solution. The acidic solution was extracted three times with 15 mL of ethyl acetate. The combined organic extract was washed with water, brine and dried over $Na_2SO_4$ and then concentrated to afford crude Compound A, which was further purified by preparative HPLC (552 mg, 85%) to yield Compound A. $^1$H-NMR (500 MHz, $CD_3OD$): δ 1.50 (bs, 6H), 1.57 (s, 3H), 1.59 (s, 3H), 1.85-2.10 (m, 8H), 2.68 (dd, J=6.5, 14.5, 1H), 2.95 (dd, J=4.5, 14.0 Hz, 1H), 3.07 (dd, J=7.0, 13.0 Hz, 1H), 3.17 (dd, J=8.5, 13.5 Hz, 1H), 4.59 (dd, J=4.5, 8.5), 4.97-5.02 (m, 2H), 5.12 (t, J=7.5, 1H), 6.21 (d, J=13.0 Hz, 1H), 6.47 (d, J=13.0 Hz, 1H). $^{13}$C-NMR (125 MHz, $CDCl_3$): δ 16.2, 16.3, 17.8, 25.3, 26.0, 27.4, 27.8, 30.3, 33.3, 40.8, 40.9, 54.0, 121.5, 125.1, 125.5, 132.1, 133.3, 134.4, 136.3, 140.7, 167.7, 168.0, 172.9; ES-MS: mass calcd for Chemical Formula: $C_{22}H_{33}NO_5S$, 423.6. Found (M+Na) m/z 446.

Example 3

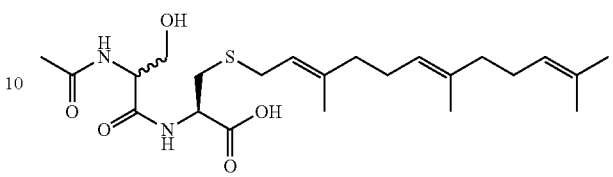

Synthesis of a mixture of ((R)-2-((S)-2-acetamido-3-hydroxypropanamido)-3-((2E,6E)-3,7,11-trimethyldodeca-2,6,10-trienylthio)propanoic acid) and ((R)-2-((R)-2-acetamido-3-hydroxypropanamido)-3-((2E,6E)-3,7,11-trimethyldodeca-2,6,10-trienylthio)propanoic acid))(Compound D)

In a 100 mL round bottom flask, N-acetyl-L-serine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture and stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (160 mg, 35%) to yield a 1:1 ratio mixture of isomeric compounds: (R)-2-((S)-2-acetamido-3-hydroxypropanamido)-3-((2E,6E)-3,7,11-trimethyldodeca-2,6,10-trienylthio)propanoic acid) and ((R)-2-((R)-2-acetamido-3-hydroxypropanamido)-3-((2E,6E)-3,7,11-trimethyldodeca-2,6,10-trienylthio)propanoic acid), i.e., isomers of Compound D. $^1$H-NMR (500 MHz, $CD_3OD$): δ 1.50 (s, 6H), 1.57 (s, 3H), 1.58 (s, 3H), 1.85-2.03 (m, 11H), 2.72-2.79 (m, 1H), 2.87-2.96 (m, 1H), 3.07-3.14 (m, 2H), 3.65-3.69 (m, 1H), 3.70-3.77 (m, 1H), 4.33 (dd, J=5.0, 10.0 Hz, 1H), 4.40 (dd, J=5.0, 10.0 Hz, 1H), 4.98-5.02 (m, 2H), 5.14 (dd, J=5.0, 15.0 Hz, 1H). $^{13}$C-NMR (125 MHz, $CD_3OD$): δ 16.12, 16.28, 17.79, 22.61, 22.71, 25.95, 27.52, 27.80, 30.74, 30.78, 35.19, 35.25, 40.79, 40.90, 55.57, 55.94, 56.87, 57.17, 63.18, 63.37, 121.78, 121.80, 125.24, 125.48, 132.09, 136.15, 140.03, 140.11, 171.84, 171.91, 173.35, 173.54, 177.14, 177.15; ES-MS: mass calcd for Chemical Formula: $C_{23}H_{98}N_2O_5S$, 454.62. Found (M+) m/z 455.3, (M+Na) m/z 477.3.

Example 4

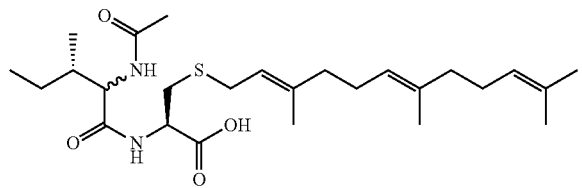 [SMILES: CC[C@H](C)C(NC(C)=O)C(=O)N[C@@H](CSC/C=C(\C)CC/C=C(\C)CCC=C(C)C)C(=O)O]

Synthesis of a mixture of ((R)-2-((2S,3S)-2-acet-amido-3-methylpentanamido)-3-((2E,6E)-3,7,11-trimethyldodeca-2,6,10-trienylthio)propanoic acid and (R)-2-((2R,3S)-2-acetamido-3-methylpentana-mido)-3-((2E,6E)-3,7,11-trimethyldodeca-2,6,10-trienylthio)propanoic acid)(Compound E)

In a 100 mL round bottom flask, N-acetyl-L-isoleucine (1.0 mmol), coupling reagent (520 mg of PBOP or 380 mg of HATU, 1 mmol) and N,N-diisopropyl-ethyl-amine (650 mg, 5 mmol) were mixed in $CH_2Cl_2$ (10 mL). The reaction mixture was stirred at room temperature for 30 minutes. S-trans, trans-farnesyl-L-cysteine (325 mg, 1 mmol) was added to the reaction mixture and stirred at room temperature overnight. $CH_2Cl_2$ was removed by rotary evaporation. The resulting residue was dissolved in ethyl acetate (50 mL). The organic solution was washed with an $NH_4Cl$ saturated solution (50 mL), dried over $Na_2SO_4$, and concentrated to afford a crude mixture. The crude mixture was purified by preparative HPLC (220 mg, 46%) to yield an isomeric mixture of (R)-2-((2S,3S)-2-acetamido-3-methylpentana-mido)-3-((2E,6E)-3,7,11-trimethyldodeca-2,6,10-trienyl-thio)propanoic acid (Compound E-1) and (R)-2-((2R,3 S)-2-acetamido-3-methylpentanamido)-3-((2E,6E)-3,7,11-trimethyldodeca-2,6,10-trienylthio)propanoic acid (Compound E-2), wherein the ratio of E-1 to E-2 is 1:1. $^1$H-NMR (500 MHz, $CD_3OD$): δ 0.80-0.86 (m, 6H), 1.06-1.33 (m, 3H), 1.50 (s, 6H), 1.57 (s, 3H), 1.60 (s, 3H), 1.79-2.01 (m, 11H), 2.71-2.77 (m, 1H), 2.87-2.94 (m, 1H), 3.09-3.11 (m, 2H), 4.17-4.43 (m, 2H), 4.99-5.00 (m, 2H), 5.26 (t, J=10.0 Hz, 1H). $^{13}$C-NMR (125 MHz, $CD_3OD$): δ 11.68, 12.14, 15.00, 16.13, 16.28, 17.80, 22.52, 22.58, 25.86, 25.96, 27.48, 27.52, 27.53, 27.80, 30.80, 30.88, 35.51, 35.56, 38.02, 38.31, 40.80, 40.90, 55.37, 55.62, 57.97, 59.80, 121.83, 121.88, 125.23, 125.48, 132.08, 136.14, 139.92, 140.02, 172.89, 173.01, 173.39, 173.46, 176.84, 177.09; ES-MS: mass calcd for Chemical Formula: $C_{26}H_{44}N_2O_4S$, 480.70. Found (M+) m/z 481.4, (M+Na) m/z 503.4.

Example 5

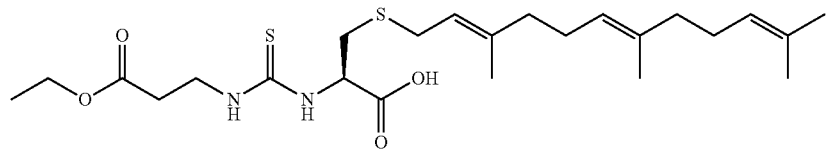 [SMILES: CCOC(=O)CCNC(=S)N[C@@H](CSC/C=C(\C)CC/C=C(\C)CCC=C(C)C)C(=O)O]

Synthesis of ((R)-2-(3-(3-ethoxy-3-oxopropyl)thiou-reido)-3-((2E,6E)-3,7,11-trimethyldodeca-2,6,10-trienylthio)propanoic acid)(Compound F)

In a 100 mL round bottom flask, to a suspension of ethyl-3-isothiocynato propionate (159 mg, 1 mmol) and S-trans, trans-farnesyl-L-cysteine (325 mg, 1 mmol) in THF (5 mL) was added N,N-diisopropyl-ethyl-amine (0.87 mL, 5 mmol) dropwise. The solution was stirred at room temperature overnight. The mixture was diluted with ethyl acetate (60 mL) and washed by 0.5 N HCl (10 mL×1), $H_2O$ (10 mL×1) and brine (10 mL×1). The organic layer was dried over $Na_2SO_4$ and concentrated in vacuo. The residue was purified by preparative HPLC (220 mg, 45%) to yield Compound F. $^1$H-NMR (500 MHz, $CD_3OD$): δ 1.17 (t, J=5.0 Hz, 3H), 1.50 (s, 3H), 1.51 (s, 3H), 1.57 (s, 3H), 1.59 (s, 3H), 1.86-2.06 (m, 8H), 2.54 (t, J=5.0 Hz, 2H), 2.77 (dd, J=5.0, 15.0 Hz, 1H), 2.95-2.96 (m, 1H), 3.05-3.06 (m, 1H), 3.16-3.20 (m, 1H), 3.68 (broad, 2H), 4.06 (q, J=5.0 Hz, 2H), 5.00-5.01 (m, 2H), 5.09-5.14 (m, 2H). $^{13}$C-NMR (125 MHz, $CD_3OD$): δ 14.65, 16.19, 16.31, 17.83, 25.97, 27.39, 27.80, 30.70, 33.22, 33.91, 34.80, 40.80, 40.90, 57.89, 61.03, 61.71, 61.93, 121.35, 121.70, 125.16, 132.11, 136.24, 140.52, 173.76, 174.47, 210.16; ES-MS: mass calcd for Chemical Formula: $C_{24}H_{40}N_2O_4S_2$ 484.72. Found (M+) m/z 485.3, (M+Na) m/z 507.3.

Example 6

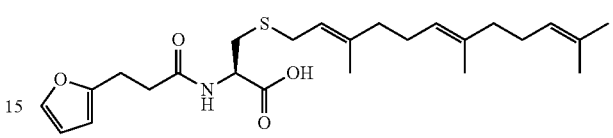

Synthesis of ((R)-2-(3-(furan-2-yl)propanamido)-3-((2E,6E)-3,7,11-trimethyldodeca-2,6,10-trienylthio)propanoic acid)(Compound G)

To a solution of 3-(2-furyl) propionic acid (168 mg, 1.2 mmol) and 4-(4,6-dimethoxy-1,3,5-triazin-2yl)-4-methyl-morpholinium chloride (DMTMM, 332 mg, 1.2 mmol) in $CH_2Cl_2$ (5 mL) was added N,N-diisopropyl-ethyl-amine (0.52 mL, 3 mmol). After stirring for 10 min, S-trans, trans-farnesyl-L-cysteine (325 mg, 1 mmol) was added slowly. The solution was stirred at room temperature overnight and then diluted with ethyl acetate (60 mL). The solution was washed by 0.5 N HCl (10 mL×1), $H_2O$ (10 mL×1) and brine (10 mL×1). The organic layer was dried over $Na_2SO_4$ and concentrated in vacuo. The residue was purified by preparative HPLC (333 mg, 74%) to yield Compound G. $^1$H-NMR (500 MHz, $CD_3OD$): δ 1.50 (s, 6H), 1.57 (s, 3H), 1.59 (s, 3H), 1.86-1.89 (m, 2H), 1.95-2.06 (m, 6H), 2.51 (t, J=8.0 Hz, 2H), 2.57-2.62 (m, 1H), 2.83-2.869 (m, 3H), 3.05 (dd, J=7.5, 13.5 Hz, 1H), 3.12-3.16 (m, 1H), 4.49 (dd, J=4.5, 8.0 Hz, 1H), 4.99-5.01 (m, 2H), 5.13 (t, J=7.5 Hz, 1H). $^{13}$C-NMR (125 MHz, $CD_3OD$): δ 16.15, 16.24, 17.80, 24.96, 25.95, 27.39, 27.79, 30.11, 33.41, 35.08, 40.79, 40.89, 53.30, 106.28, 111.19, 121.61, 125.14, 125.46, 132.12, 136.27, 140.49, 142.36, 155.72, 174.00, 174.78; ES-MS: mass calcd for Chemical Formula: $C_{25}H_{37}NO_4S$, 447.63. Found (M+1) m/z 448.3, (M+23) m/z 470.2.

Example 7

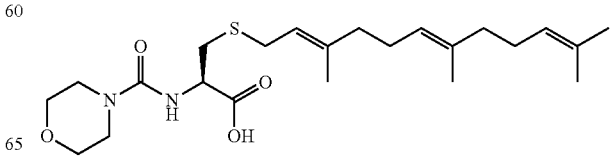

Synthesis of ((R)-2-(morpholine-4-carboxamido)-3-((2E,6E)-3,7,11-trimethyldodeca-2,6,10-trienylthio)propanoic acid)(Compound H)

In 100 mL round bottom flask, S-trans, trans-farnesyl-L-cysteine (325 mg, 1.0 mmole) and potassium carbonate (1.3 g, 10 mmole) were dissolved in THF (50 mL). 4-morpholine carbonyl chloride (160 mg, 1.2 mmole) was added. The reaction mixture was stirred at room temperature for 47 hours. THF was removed by rotary evaporation. The crude material was washed with water (10 mL) and 1N HCl solution (10 mL). The remaining crude material was purified by preparative HPLC (120 mg, 27% yield) to yield Compound H: $^1$H-NMR (500 MHz, CDCl$_3$) δ 1.60 (bs, 6H), 1.66 (s, 3H), 1.67 (s, 3H), 1.95-2.12 (m, 8H), 2.94-3.02 (m, 2H), 3.10-3.20 (m, 2H), 3.40-3.44 (m, 4H), 3.71 (t, J=4.8 Hz, 4H), 4.55 (dd, J=6.3, 11.6 Hz, 1H), 5.09 (t, J=6.9 Hz, 2H), 5.19 (t, J=7.6 Hz, 1H). $^{13}$C-NMR (125 MHz, CDCl$_3$): δ 16.0, 16.2, 17.7, 25.7, 26.4, 26.7, 29.9, 33.0, 39.6, 39.7, 44.0, 53.0, 66.3, 119.4, 123.7, 124.3, 131.3, 135.4, 140.2, 157.7, 174.1; ES-MS: mass calcd for Chemical Formula: C$_{23}$H$_{38}$N$_2$O$_4$S, 438.3 (M+). Found (M+Na) m/z 461.4.

Example 8

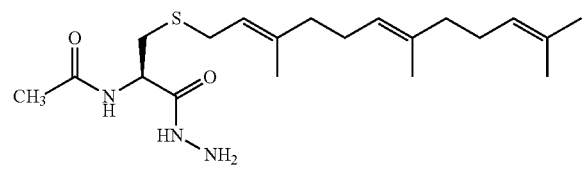 [SMILES: CC(=O)N[C@@H](CSC/C=C(\C)CC/C=C(\C)CCC=C(C)C)C(=O)NN]

Synthesis of (N—((R)-1-hydrazinyl-1-oxo-3-((2E,6E)-3,7,11-trimethyldodeca-2,6,10-trienylthio)propan-2-yl)acetamide)(Compound I)

In 50 mL round bottom flask, N-acetyl-S-farnesyl-L-cysteine (368 mg, 1.0 mmole) was dissolved in dichloromethane (10 mL). N-Cyclohexylcarbodiimide,N'-methyl polystyrene HL (1.7 g, 3.3 mole, from NovabioChem) was added followed by sufficient dichloromethane to swell the resin and keep the reaction mobile and the mixture gently magnetically stirred in 30 minutes. 5 mL of hydrazine in THF (1M) was added to the reaction solution and the reaction mixture was stirred in 3 hours at room temperature. The used resin was removed by filtration and washed with dichloromethane. Evaporation of the filtrate provided crude reaction mixture. The desired product was purified by preparative HPLC (305 mg, 80% yield) to yield Compound I: $^1$H-NMR (500 MHz, CDCl3): δ 1.60 (s, 6H), 1.67 (s, 6H), 1.70 (S, 3H), 1.92-2.09 (m, 8H), 2.75 (dd, J=7.9, 13.9 Hz, 1H), 2.88 (dd, J=5.7, 13.6 Hz, 1H), 3.20 (d, J=7.9 Hz, 2H), 4.51 (dd, J=7.6, 13.6 Hz, 1H), 5.10 (m, 2H), 5.24 (t, J=7.6 Hz, 1H). $^{13}$C-NMR (125 MHz, CDCl3): δ 16.0, 16.1, 16.2, 17.6, 17.7, 23.2, 23.4, 23.5, 25.7, 25.8, 26.2, 26.3, 26.5, 26.7, 30.0, 31.8, 31.9, 32.9, 33.2, 39.6, 39.7, 39.9, 51.3, 51.4, 119.6, 120.3, 123.6, 124.2, 131.4, 131.6, 135.5, 135.6, 135.8, 140.2, 140.3, 170.2, 171.1; ES-MS: mass calcd for Chemical Formula: C$_{20}$H$_{35}$N$_3$O$_2$S, 381.2 (M+). Found (M+Na) m/z 404.3.

Example 9

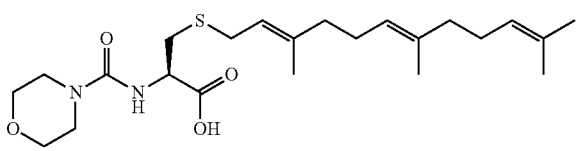 [SMILES: CC(C)=CCC/C(C)=C/CC/C(C)=C/CSC[C@H](NC(=O)N1CCOCC1)C(=O)O]

Synthesis of Compound H

In 100 mL round bottom flask, S-trans, trans-farnesyl-L-cysteine (325 mg, 1.0 mmole) and potassium carbonate (1.3 g, 10 mmole) were dissolved in THF (50 mL). 4-morpholine carbonyl chloride (160 mg, 1.2 mmole) was added. The reaction mixture was stirred at room temperature for 47 hours. THF was removed by rotary evaporation. The crude material was washed with water (10 mL) and 1N HCl solution (10 mL). The remaining crude material was purified by preparative HPLC (120 mg, 27% yield): $^1$H-NMR (500 MHz, CDCl$_3$) δ 1.60 (bs, 6H), 1.66 (s, 3H), 1.67 (s, 3H), 1.95-2.12 (m, 8H), 2.94-3.02 (m, 2H), 3.10-3.20 (m, 2H), 3.40-3.44 (m, 4H), 3.71 (t, J=4.8 Hz, 4H), 4.55 (dd, J=6.3, 11.6 Hz, 1H), 5.09 (t, J=6.9 Hz, 2H), 5.19 (t, J=7.6 Hz, 1H); $^{13}$C-NMR (125 MHz, CDCl$_3$) δ 16.0, 16.2, 17.7, 25.7, 26.4, 26.7, 29.9, 33.0, 39.6, 39.7, 44.0, 53.0, 66.3, 119.4, 123.7, 124.3, 131.3, 135.4, 140.2, 157.7, 174.1; ES-MS: mass calcd for Chemical Formula: C$_{23}$H$_{38}$N$_2$O$_4$S, 438.3 (M+). Found (M+Na) m/z 461.4.

Example 10

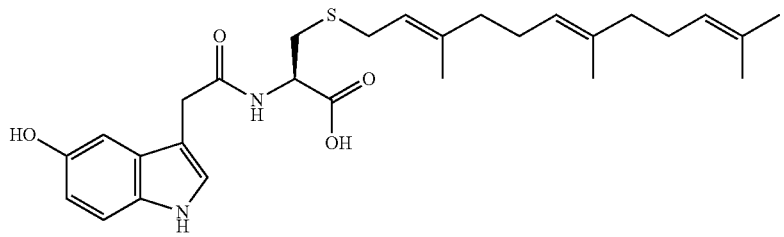 [SMILES: CC(C)=CCC/C(C)=C/CC/C(C)=C/CSC[C@H](NC(=O)Cc1c[nH]c2ccc(O)cc12)C(=O)O]

Synthesis of ((R)-2-(2-(5-hydroxy-1H-indol-3-yl)acetamido)-3-((2E,6E)-3,7,11-trimethyldodeca-2,6,10-trienylthio)propanoic acid)(Compound J)

In 24 mL vial, 5-hydroxyl indole-3-acetic acid (191 mg, 1.0 mmol), HATU (380 mg, 1 mmol) and N,N-diisopropyl-ethyl-amine (650 mg, 5 mmol) were mixed in THF (10 mL). The reaction mixture was stirred at room temperature for 30 minutes. S-trans, trans-Farnesyl-L-cysteine (325 mg, 1 mmol) was added to the reaction mixture. The reaction mixture was stirred at room temperature overnight. THF was removed by rotary evaporation. The resulting residue was dissolved in ethyl acetate (50 mL). The organic solution was 140.47, 144.46, 174.98, 174.64; ES-MS: mass calcd for Chemical Formula: $C_{25}H37NO_3S_2$ 463.70. Found (M+23) m/z 486.2.

Example 12

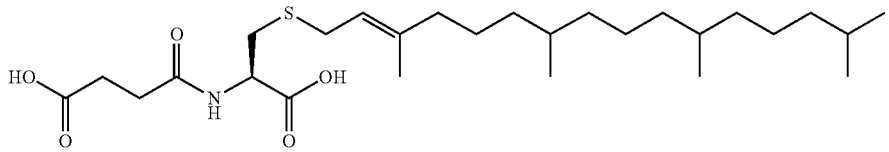

washed with water (50 mL) and brain (50 mL), dried over $Na_2SO_4$, and concentrated to afford a crude mixture. The crude mixture was purified by preparative HPLC (210 mg, 42%) to yield Compound J. $^1$H-NMR (500 MHz, $CD_3OD$): δ 1.49 (s, 9H), 1.56 (S, 3H), 1.85-1.98 (m, 6H), 2.62 (dd, J=8.0, 14.0 Hz, 1H), 2.80 (dd, J=4.5, 14.0 Hz, 1H), 2.88 (dd, J=7.0, 13.0 Hz, 1H), 2.98 (dd, J=8.5, 13.0 Hz, 1H), 3.55 (dd, J=6.5, 22.5 Hz, 2H), 4.49 (dd, J=5.0, 8.0 Hz, 1H), 4.98 (bs, 2H), 6.57 (d, J=8.5 Hz, 1H), 6.84 (s, 1H), 7.07 (d, J=6.5 Hz, 2H). $^{13}$C-NMR (125 MHz, $CD_3OD$): δ 16.2, 17.8, 26.0, 27.3, 27.4, 27.8, 28.8, 30.2, 33.3, 33.8, 40.7, 40.9, 53.4, 103.7, 108.2, 112.7, 112.8, 121.5, 125.2, 125.5, 125.8, 129.3, 132.1, 133.0, 136.2, 140.5, 151.5, 173.9, 174.9; ES-MS: mass calcd for Chemical Formula: C28H38N2O4S, 498.3 (M+). Found (M+1) m/z 499.2.

Example 11

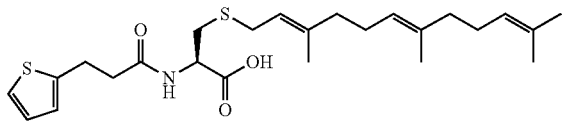 [SMILES: CC(C)=CCC/C(C)=C/CC/C(C)=C/CSC[C@H](NC(=O)CCc1cccs1)C(=O)O]

Synthesis of ((R)-2-(3-(thiophen-2-yl)propana-mido)-3-((2E,6E)-3,7,11-trimethyldodeca-2,6,10-trienylthio)propanoic acid)(Compound K)

To a solution of 3-(2-thienyl) propanoic acid (187 mg, 1.2 mmol) and 4-(4,6-dimethoxy-1,3,5-triazin-2yl)-4-methyl-morpholinium chloride (DMTMM, 332 mg, 1.2 mmol) in $CH_2Cl_2$ (5 mL) was added N,N-diisopropyl-ethyl-amine (0.52 mL, 3 mmol). After stirring for 5 min, S-trans, trans-farnesyl-L-cysteine (325 mg, 1 mmol) was added slowly. The solution was stirred at room temperature for 4 h and then diluted with ethyl acetate (60 mL). The solution was washed sequentially with an $NH_4Cl$ saturated solution (15 mL×2), $H_2O$ (10 mL×1) and brine (15 mL×1). The organic layer was dried over $Na_2SO_4$ and concentrated in vacuo. The residue was purified by preparative HPLC (310 mg, 67%) to yield Compound K. $^1$H-NMR (500 MHz, $CD_3OD$): δ 1.50 (s, 6H), 1.57 (s, 3H), 1.59 (s, 3H), 1.86-1.89 (m, 2H), 1.96-2.06 (m, 6H), 2.54 (t, J=7.5 Hz, 2H), 2.56-2.61 (m, 1H), 2.87 (dd, J=4.5, 14.0 Hz, 1H), 3.00-3.06 (m, 3H), 3.11-3.15 (m, 1H), 4.49 (dd, J=5.0, 8.5 Hz, 1H), 5.00-5.01 (m, 2H), 5.12 (t, J=7.5 Hz, 1H). $^{13}$C-NMR (125 MHz, $CD_3OD$): δ 16.16, 16.25, 17.81, 25.96, 26.74, 27.40, 27.79, 30.13, 33.42, 38.74, 40.79, 40.89, 53.32, 121.62, 124.36, 125.14, 125.47, 125.75, 127.81, 132.11, 136.27, Synthesis of (N-[1-Carboxy-2-(3,7,11,15-tetram-ethyl-hexadec-2-enylsulfanyl)-ethyl]-succinamic acid)(Compound L)

In a 100 mL round bottom flask, phytol (trans: cis (2:1) isomeric mixture of 34.9 mL, 100 mmol) and triethylamine (1.4 mL, 10 mmol) were added to toluene (100 mL), the reaction mixture was cooled down to −78° C. Phosphorus tribromide (4.7 mL, 50 mmol) was added dropwise. After addition complete, the reaction mixture was warmed up to room temperature and stirred for 4 hours. Water (100 mL) was added dropwise to quench the reaction. Ethyl acetate (200 mL) was added and then washed with water (50 mL×2) and brine (50 mL×2) sequentially. The ethyl acetate solution was dried by $Na_2SO_4$ and concentrated in vacuo to afford a crude mixture of 1:1 trans isomers and 1:1 cis isomers of compound L, wherein the ratio of trans isomers to cis isomers is 7:3. The crude mixture (1 mmol) and LiOH (126 mg, 3 mmol) were mixed in THF (3 mL) and water (3 mL). The reaction solution was stirred at room temperature for 4 hours. Ethyl acetate (50 mL) was added and then washed with IN HCl (20 mL×2) and brine (20 mL×2) sequentially. The ethyl acetate solution was dried by $Na_2SO_4$ and concentrated in vacuo to afford a partially purified mixture that was purified by HPLC to yield two fractions.

The first fraction yielded a mixture of 1:1 trans isomers and 1:1 cis isomers of compound L, wherein the ratio of trans isomers to cis isomers is 1:1 (50 mg, 20%). $^1$H-NMR (500 MHz, MeOH-$d_4$): δ 0.76-0.79 (m, 12H), 1.00-1.46 (m, 19H), 1.58 and 1.63 (s, 3H), 1.90-1.93 (m, 2H), 2.46-2.49 (m, 4H), 2.62-2.66 (m, 1H), 2.87 (dd, J=4.5, 14.0 Hz, 1H), 3.04-3.07 (m, 1H), 3.14-3.18 (m, 1H), 4.46-4.49 (m, 1H), 5.12 (t, J=7.5 Hz, 1H). $^{13}$C-NMR (125 MHz, MeOH-$d_4$): δ 16.11, 20.13, 20.17, 20.23, 23.06, 23.15, 23.59, 25.53, 25.95, 26.31, 26.65, 29.19, 30.25, 30.29, 30.41, 31.41, 31.44, 32.88, 33.56, 33.79, 33.83, 33.94, 33.98, 37.62, 37.72, 37.92, 38.01, 38.41, 38.47, 38.51, 40.57, 40.96, 53.43, 53.44, 53.56, 121.44, 121.90, 140.86, 141.00, 174.02, 174.05, 174.47, 174.52, 176.17, 176.19; ES-MS: mass calcd for Chemical Formula: $C_{27}H_{49}NO_5S$, 499.3. Found (M+Na) m/z 522.3.

The second fraction yielded a 1:1 mixture of trans isomers of compound L (45 mg, 23%). $^1$H-NMR (500 MHz, MeOH-$d_4$): δ 0.76-0.79 (m, 12H), 1.00-1.46 (m, 19H), 1.58 (s, 3H), 1.90-1.93 (m, 2H), 2.46-2.49 (m, 4H), 2.63 (dd, J=8.5, 13.5 Hz, 1H), 2.87 (dd, J=4.5, 14.0 Hz, 1H), 3.02-3.07 (m, 1H), 3.14-3.18 (m, 1H), 4.46-4.49 (m, 1H), 5.11 (t, J=7.5 Hz, 1H). $^{13}$C-NMR (125 MHz, MeOH-$d_4$): δ 16.10, 16.11, 20.11, 20.16, 20.22, 23.05, 23.14, 25.52, 25.94, 25.95, 26.30, 26.32, 29.19, 30.23, 30.23, 30.28, 31.40, 33.54, 33.55, 33.79, 33.82, 33.94, 33.97, 37.61, 37.71, 38.40, 38.47, 38.50, 38.53, 40.56, 40.95, 53.43, 121.44, 140.87, 174.03, 174.53, 176.19; ES-MS: mass calcd for Chemical Formula: $C_{27}H_{49}NO_5S$, 499.3. Found (M+Na) m/z 522.3.

Example 13

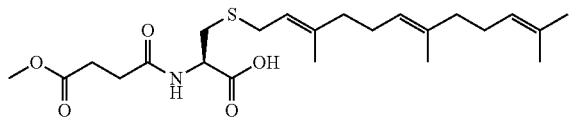 [SMILES: COC(=O)CCC(=O)N[C@@H](CSC/C=C(\C)CC/C=C(\C)CCC=C(C)C)C(=O)O]

Synthesis of ((R)-2-(4-methoxy-4-oxobutanamido)-3-((2E,6E)-3,7,11-trimethyldodeca-2,6,10-trienyl-thio)propanoic acid)(Compound M)

In a 100 mL round bottom flask, mono-methyl succinate (132 mg, 1 mmol), 2-(7-Aza-1H-benzotriazole-1-yl)-1,1,3,3-tetramethyluronium hexafluorophosphate 1.1 mg, 1.1 mmol) and N,N-diisopropyl-ethyl-amine (0.52 mL, 3 mmol) were mixed in THF (5 mL). The reaction solution was stirred at room temperature for ten minutes. S-trans, trans-Farnesyl-L-cysteine (325 mg, 1 mmol) was added to reaction mixture. The reaction solution was stirred at room temperature overnight. Ethyl acetate (50 mL) was added and then washed with saturated ammonium chloride aqueous solution (20 mL×2), DI water (20 mL×2) and brine (20 mL×2) sequentially. The ethyl acetate solution was dried by $Na_2SO_4$ and concentrated in vacuo to afford a crude Compound M. The crude Compound M was purified by HPLC (110 mg, 25%) to yield Compound M. $^1$H-NMR (500 MHz, MeOH-$d_4$): δ 1.50 (s, 6H), 1.57 (s, 3H), 1.58 (s, 3H), 1.85-1.88 (m, 2H), 1.91-1.96 (m, 4H), 1.99-2.03 (m, 2H), 2.46-2.54 (m, 4H), 2.68 (dd, J=7.5, 13.5 Hz, 1H), 2.90 (dd, J=4.5, 13.5 Hz, 1H), 3.09-3.12 (m, 2H), 3.21 (s, 3H), 4.35 (dd, J=4.5, 7.0 Hz, 1H), 4.98-5.02 (m, 2H), 5.14 (t, J=7.5 Hz, 1H). $^{13}$C-NMR (125 MHz, MeOH-$d_4$): δ 16.12, 16.25, 17.79, 25.94, 27.48, 27.79, 30.40, 30.69, 31.73, 35.49, 40.77, 40.89, 52.24, 55.45, 121.82, 125.22, 125.47, 132.08, 136.15, 139.97, 173.57, 174.80, 177.17; ES-MS: mass calcd for Chemical Formula: $C_{23}H_{37}NO_5S$, 439.2. Found (M+Na) m/z 462.2.

Biological Examples

Described below are assays used to measure the biological activity of described compounds, including the anti-bacterial properties of the compounds, as measured by inhibition of bacterial growth (Example 14) and determination of minimum bactericidal concentration ("MBC") (Example 15).

Example 14

Inhibition of *Propionibacterium acnes* Growth

The present example demonstrates that certain described isoprenyl compounds exhibit superior or similar anti-bacterial activity when compared to benzoyl peroxide, a well-known anti-bacterial and anti-acne agent. The assay for the inhibition of growth of *Propionibacterium acnes* bacteria was described elsewhere (Nakatsuji et al., *J Invest Dermatol*, 2009, 129: 2480-2488). In brief, the strain ATCC 6919 of *P. acnes* (American Type Culture Collection, Manassas, Va.) was cultured on *Brucella* agar (RO1254, Remel, Lenexa, Kans.) supplemented with 5% (v/v) defibrinated sheep blood, vitamin K (5 mg/ml, Remel, Lenexa, Kans.), and hemin (50 mg/ml, Remel, Lenexa, Kans.), under an anaerobic condition using Gas-Pak (BD, Sparks, MD) at 37° C. A single colony was inoculated in Reinforced *Clostridium* Medium (Oxford, Hampshire, England) and cultured at 37° C. under the anaerobic condition. Each of the described isoprenyl compounds A, B, C, D, E, F, G, H, I, J, K and L were dissolved in 100% (v/v) DMSO. Samples of each described isoprenyl compound and a solution of benzoyl peroxide ("BPO") were then each incubated with an inoculum of *P. acnes* at a concentration of 1×10$^6$ CFU per mL in Reinforced *Clostridium* Medium in a 96-well microplate (100 µL per well) under anaerobic conditions for 72 hours. Samples of each described isoprenyl compound were tested at final concentrations per well of 0.25 µg/mL, 0.5 µg/mL, 1.0 µg/mL, 1.95 µg/mL, 3.9 µg/mL, 7.8 µg/mL, 15.625 µg/mL, 31.25 µg/mL, 62.5 µg/mL, 125 µg/mL, 250 µg/mL, and 500 µg/mL. A control well received only 5% (v/v) of DMSO in place of a sample of a described isoprenyl compound. After 72 hours incubation under anaerobic conditions, the *P. acnes* cultures in the 96-well microplate were mixed well and then absorbance readings at 600 nm were taken to determine bacterial growth. *P. acnes* growth curves was plotted and the concentration of each described isoprenyl compound tested that yielded 50% inhibition of bacterial growth (IC50) was determined using SigmaPlot. IC50 ranges demonstrating the effect of provided isoprenyl compounds on inhibition of *P. acnes* growth for BPO, deoxycycline, AFC, compounds A, B, C, D, E, F, G, H, I, J, K, and L, are listed in column 1 of FIG. 1. Growth curves of *P. acnes* determined for BPO, AFC, compound G and compound H are depicted in FIG. 2.

Example 15

Determination of Minimum Bactericidal Concentration

Figure 3:
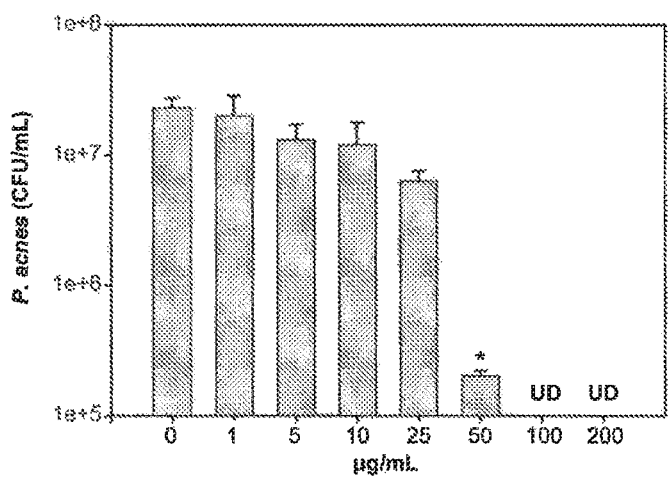
FIG. 3 presents bar graphs depicting the concentration of *P. acnes* bacteria obtained with different concentrations of AFC and compound A, demonstrating the minimum bactericidal concentration for the compounds.
Figure 3:
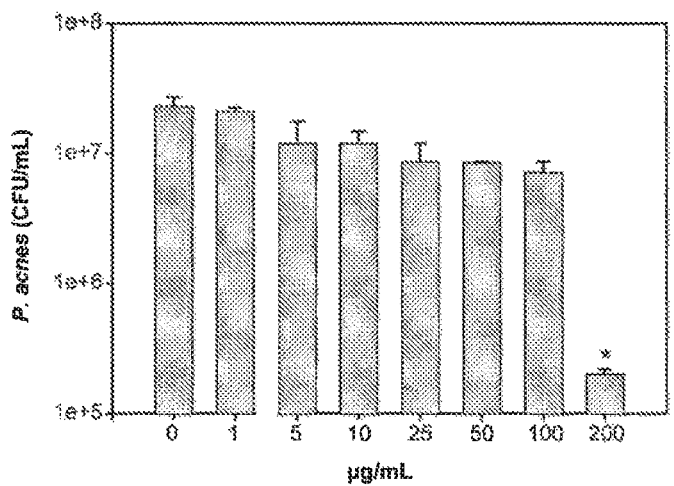

The present example demonstrates that certain described isoprenyl compounds exhibit anti-bacterial activity and exhibit low minimum bactericidal concentrations. The Minimal Bactericidal Concentration ("MBC") of the described isoprenyl compounds against *P. acnes* was determined using the following method. Sample solutions of described isoprenyl compounds, for example, AFC and compound A, dissolved in 100% (v/v) DMSO, were each incubated with an inoculum of *P. acnes* at a concentration of 1×10$^7$ CFU/mL in a 96-well microplate with a total culture of 100 µl per well under anaerobic conditions, to yield final compound concentrations per well of 1 µg/mL, 5 µg/mL, 10 µg/mL, 25 µg/mL, 50 µg/mL, 100 µg/mL and 200 µg/mL. A control well received only 5% (v/v) of DMSO in place of the test solution of a described isoprenyl compound. Following 5 hours of incubation, the reaction mixture was serially (1:10-1:10$^6$) diluted with PBS. The MBC was determined by inoculating the diluted culture (5 µl) onto a *brucella* agar plate (RO1254, Remel, Lenexa, Kans.). 72 hours after inoculation, colonies on the plates were counted, CFUs (Colony Forming Units) were calculated and the data was plotted by using Sigma-Plot. The bacterial concentration (CFU/mL) of *P. acnes*, obtained with different concentrations of AFC (panel A) and compound A (panel B) to determine the MBC of each compound are depicted in FIG. 3.

Example 16

*P. acnes*-Induced Mouse Ear Model of Inflammation—MPO Endpoint

The methods for a model of *P. acnes*-inflammation are described elsewhere (Nakatsuji et al., *J. Invest. Dermatol.*, 2008, 128: 2451-2457). Using this mouse in vivo model for *P. acnes*-induced inflammation, the present example demonstrates that certain described isoprenyl compounds, when topically applied to a site of inflammation induced by bacterial challenge exhibit in vivo anti-inflammatory activity, as evidenced by the effect on the commonly-used inflammatory end-points such as neutrophil infiltration (MPO neutrophil marker). Using this mouse in vivo model for *P. acnes*-inflammation, the present example further demonstrates that certain described isoprenyl compounds, when topically applied to a site of inflammation induced by bacterial challenge, for example by *P. acnes* exhibit in vivo anti-inflammatory activity, as evidenced by the effect on the commonly-used inflammatory end-points such as neutrophil infiltration (MPO neutrophil marker), and are therefore useful as anti-acne agents.

The protocol for inducing inflammation using *P. acnes* bacterial challenge on the mouse ear was slightly modified from the method described previously (Natatsuji et al., 2008). Briefly, Swiss Webster (ICR, 6-8 weeks old) mouse ears were injected with living *P. acnes* culture intradermally. An amount of 20 µl aliquots of living *P. acnes* (ATCC 6919, $3\times10^6$ CFU) suspended in PBS was intradermally injected in the central portion of the ear. As a control, 20 µl of PBS was injected into control animals. Significant cutaneous erythema, ear swelling (edema), and granulomatous response (MPO activity) were observed in *P. acnes*-injected ear 24 hours after the bacterial injection, but not induced by phosphate-buffered saline (PBS) injection.

To assay for inhibition of dermal neutrophil infiltration by described isoprenyl compounds, a standard method was used (see Bradley et al., *J Invest Dermatol*, 1982, 78: 206-209; Young et al., *J Invest Dermatol*, 1983, 80: 48-52; De Young et al, *Agents Actions*, 1989, 26: 335-41; and Rao et al., *Inflammation*, 1993, 17: 723-41). Briefly, 6 mm biopsy punches taken from both compound-treated ears as well as non-treated control ears were homogenized in 400 µl of 0.5% hexadecyltrimethylammonium bromide in 50 mM potassium phosphate buffer (pH 6.0) using the Fast Prep 24 (MP Biomedicals, Solon, Ohio). Supernatants were assayed for MPO activity using a model EL 340 96-well plate reader (BioTek Instruments, Winooski, Vt.). The percent inhibition of neutrophil infiltration by each described isoprenyl compound was determined by comparing the average MPO levels in the presence and absence of these compounds. The percent inhibition of MPO was determined by taking the average MPO activity of compound-treated ears and dividing it by the average MPO activity of 12 ears that only received the *P. acnes* challenge and subtracting that value from 100%. These values were corrected for the MPO activity of normal, non *P. acnes*-treated mouse ears of littermate controls. Summary of MPO activity ranges determined from an MPO activity assay for dexamethasone (administered at a dose of 1.6 mg/20 µL), clobetasol (administered at a dose of 0.1 mg/20 µL), salicylic acid (administered at a dose of 0.4 mg/20 µL), AFC (administered at a dose of 0.8 mg/20 µL), compound A (administered at a dose of 0.8 mg/20 µL), compound D (administered at a dose of 0.4 mg/20 µL), compound F (administered at a dose of 0.4 mg/20 µL), compound G (administered at a dose of 0.4 mg/20 µL), compound I (administered at a dose of 0.4 mg/20 µL), compound J (administered at a dose of 0.4 mg/20 µL), K (administered at a dose of 0.4 mg/20 µL), and L (administered at a dose of 0.4 mg/20 µL) are presented in FIG. 4.

Example 17

*P. acnes*-Induced Mouse Ear Model of Inflammation—Cytokine Release

The protocol for inducing acute inflammation in mouse ears using *P. acnes* has been described elsewhere (Nakatsuji et al., *J Invest Dermatol*, 2008, 128: 2451-2457) and similar to the protocol described in Example 15. Using this mouse in vivo model for contact irritation, the present example demonstrates that certain described isoprenyl compounds, when topically applied, exhibit in vivo anti-inflammatory activities at sites of inflammation induced by *P. acnes*, in part, by inhibiting the levels of pro-inflammatory cytokines, such as IL-6, TNF-α, IL-8 and IL-1β, resulting in the observed effects on the inflammatory end-point of neutrophil infiltration (MPO neutrophil marker), as demonstrated in Example 15. The present example therefore demonstrates that certain described isoprenyl compounds are useful for treating bacterial induced inflammation and are therefore useful as anti-acne agents.

The protocol for inducing inflammation using *P. acnes* bacterial challenge on the mouse ear was slightly modified from the method described previously (Natatsuji et al., 2008). Briefly, Swiss Webster (ICR, 6-8 weeks old) mouse ears were injected with living *P. acnes* (strain ATCC 6919) culture intradermally. An amount of 20 µl aliquots of living *P. acnes* (ATCC 6919, $3\times10^6$ CFU) suspended in PBS was intradermally injected in the central portion of the ear. As a control, 20 µl of PBS was injected into control animals. Significant cutaneous erythema, ear swelling (edema), and granulomatous response (MPO activity) were observed in *P. acnes*-injected ear 24 hours after the bacterial injection, but not induced by phosphate-buffered saline (PBS) injection. Ear tissue biopsies (6 mm), taken from both compound-treated ears and non-treated control ears were obtained and homogenized using a Fast Prep 24 (MP Biomedicals, Solon, Ohio) for two cycles of 45 seconds with Lysing Matrix A in mammalian extraction buffer (Pierce) with protease inhibitors cocktail (Roche). Supernatants were assayed by enzyme-linked immunosorbent assays (ELISA) for the stimulated release of IL-6, TNF-α, IL-8, and IL-1β, using appropriate protein standards (BD Pharmigen).

Summary of cytokine activity ranges determined with dexamethasone (administered at a dose of 1.6 mg/20 µL), clobetasol (administered at a dose of 0.1 mg/20 µL), salicylic acid (administered at a dose of 0.4 mg/20 µL), AFC (administered at a dose of 0.8 mg/20 µL), compound A (administered at a dose of 0.8 mg/20 µL), compound D (administered at a dose of 0.4 mg/20 µL), compound F (administered at a dose of 0.4 mg/20 µL), compound G (administered at a dose of 0.4 mg/20 µL), compound I (administered at a dose of 0.4 mg/20 µL), compound B (administered at a dose of 0.4 mg/20 µL), compound J (administered at a dose of 0.4 mg/20 µL), K (administered at a dose of 0.4 mg/20 µL), and L (administered at a dose of 0.4 mg/20 µL) for IL-6 levels are presented in FIG. 5, for TNF-α levels are presented in FIG. 6, for IL-8 levels are presented in FIG. 7, and for IL-1β levels are presented in FIG. 8.

Example 18

*P. acnes*-Induced Cytokine Release in NHEK Cells

Figure 9:
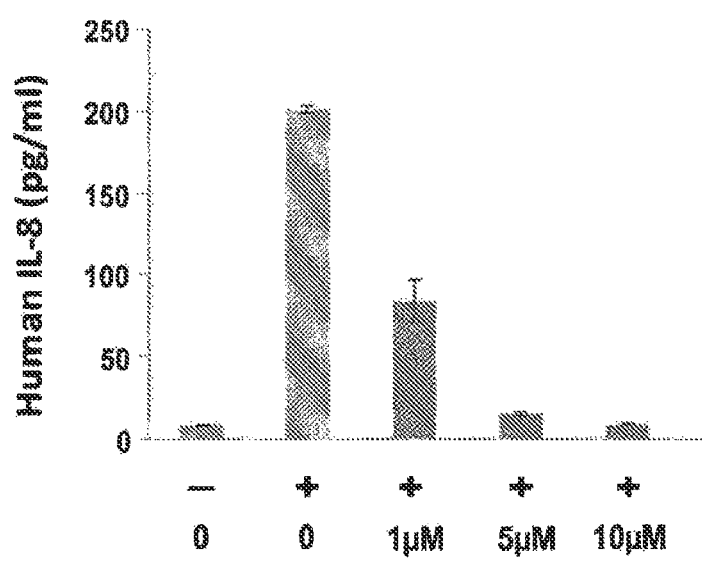
FIG. 9 presents a bar graph depicting IL-8 levels (pg/mL) demonstrating a dose dependent inhibition of *P. acnes*-induced IL-8 release with compound K, determined using Normal Human Epidermal Keratinocyte (NHEK) cell cultures.

The protocol for inducing inflammatory response in human cell lines using *P. acnes* has been described elsewhere (Nakatsuji et al., *J Invest Dermatol*, 2008, 128: 2451-2457). Using this *P. acnes*-induced inhibition of cytokine release model in NHEK cell line, the present example demonstrates that certain described isoprenyl compounds exhibit anti-inflammatory activities in human keratinocyte cultures when induced by *P. acnes*, in part, by inhibiting the levels of pro-inflammatory cytokines, such as IL-8. Briefly, normal primary adult human keratinocytes (NHEKs) were obtained from pooled donors and purchased from Cascade Biologics (Gibco; Carlsbad, Calif.) or Scien-Cell Research Labs (Carlsbad, Calif.). Cell treatments were performed only in the second and third passage in 96-well plates seeded with $5\text{-}10 \times 10^3$ cells per well. NHEK cells were cultured in keratinocyte growth medium (KGM; Gibco), in a serum-free environment, supplemented with EGF (10 ng/ml), hydrocortisone (1 µg/ml), bovine insulin (5 µg/ml) and human pituitary gland extract (2 mL) at 37° C. with 5% $CO_2$. To avoid any possible immunomodulating effects of these agents during agonist/antagonist treatments, cells were kept in KGM supplemented without EGF or hydrocortisone (depleted medium) 24 hours before treatments. The day of treatment, cells were pre-incubated with described isoprenyl compounds (0.1-100 µM; 1% v/v ethanol) in fresh depleted media in triplicates. After pre-incubation, cells were treated with *P. acnes* ($1 \times 10^7$ CFU/ml) in DMSO for 24 hours at 37° C. Later, supernatants were harvested and stored in −80° C. and cells were subjected to viability tests by the MTT assay (Promega; Madison, Wis.). IL-8 levels (pg/mL), obtained with Compound K using the *P. acnes*-induced inflammation model in NHEK cells are depicted in FIG. 9.

Example 19

Figure 10:
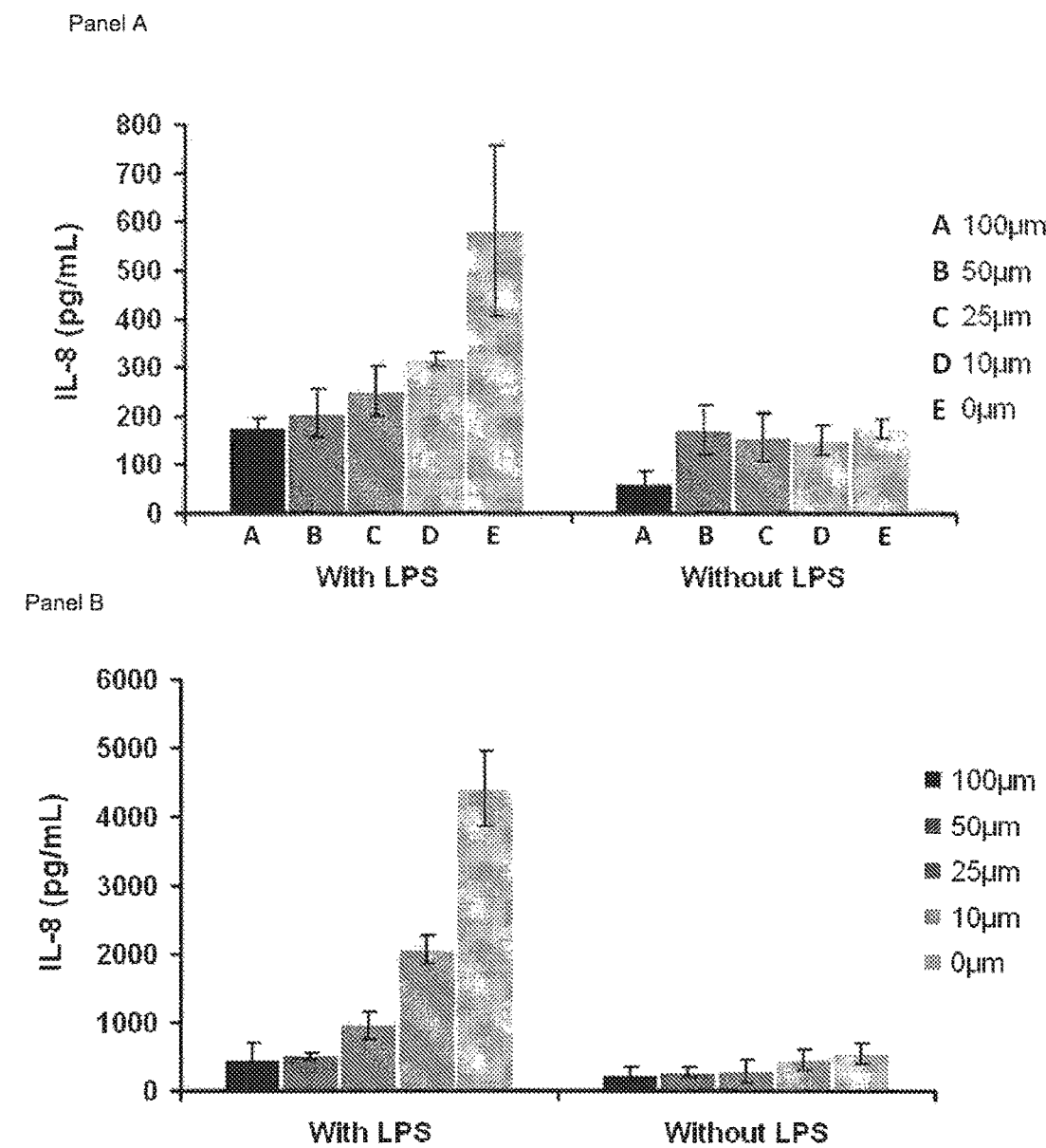
FIG. 10 presents a bar graph depicting IL-8 levels (pg/mL) demonstrating a dose dependent inhibition of LPS-TLR4 induced IL-8 release with AFC (Panel A) and Compound A (Panel B), determined using human microvascular endothelial cell line-1 (HMEC-1) cultures.

LPS-TLR4-Induced Inflammation Model in HMEC-1 Cells—Inhibition of Cytokine Levels The activation of Toll-like receptor 4 (TLR4) by lipopolysaccharide (LPS), a common class of bacterial endotoxin, induces the release of proinflammatory cytokines that are necessary to mediate key immune and inflammatory responses (reviewed in Yong-Chen et al., *Cytokines*, 2008, 42: 145-151). The present example demonstrates that certain described isoprenyl compounds inhibit TLR4 inflammatory signaling pathways resulting in reduction of proinflammatory cytokine release, for example of IL-8. Human Microvascular Endothelial cells (HMECs) were cultured in EC basal medium (EBM; Cambrex, Walkersville, Md.), supplemented with 0.5% fetal bovine serum (FBS), epidermal growth factor (EGF) (10 ng/mL) hydrocortisone (1 µg/mL) and 100 U/mL penicillin/100 µg/mL streptomycin at 37° C. with 5% $CO_2$ (referred to as supplemented media). In order to avoid possible immunomodulating effects of these agents during agonist/antagonist treatments, for some periods, cells were kept in EBM supplemented only with 0.5% FBS and penicillin/streptomycin without EGF or hydrocortisone (referred to as depleted media). Cells were plated at a concentration of $0.25 \times 10^6$ cells/well in supplemented media in 12-well plates. After cells were allowed to adhere (6-8 hours), media was changed to depleted media. After 24 hours, depleted media was removed and fresh depleted media containing various concentrations of AFC and Compound A in triplicate were added to the appropriate wells. Two hours later, to induce a pro-inflammatory response, LPS was added (100 µM) in separate wells (in triplicate) (Bender et al., *Exp Dermatol*, 2008, 17: 752-60; and Seiffert et al., *J Invest Dermatol*, 2006, 126: 1017-27). Cell cultures were examined for viability by Trypan blue exclusion and the reduction of 3-(4,5-dimethylthiazol-2-yl)-5-(3-carboxymethoxyphenyl)-2-(4-sulfophenyl)-2H-tetrazolium (MTS assay; Promega, Madison, Wis.) to determine the percentage of viable cells of various treatment concentrations of AFC and Compound A. After 6 hours of incubation, supernatants were harvested and assayed by enzyme-linked immunosorbent assays (ELISA) for the stimulated release of IL-8 using appropriate protein standards (BD Pharmigen). IL-8 levels (pg/mL), obtained with AFC (panel A) and Compound A (panel B) using an LPS-TLR4-induced inflammation model in HMEC-1 cells are depicted in FIG. 10.

Example 20

PGN-TLR2-Induced Inflammation Model in NHEK Cells—Inhibition of Cytokine Levels

Figure 11:
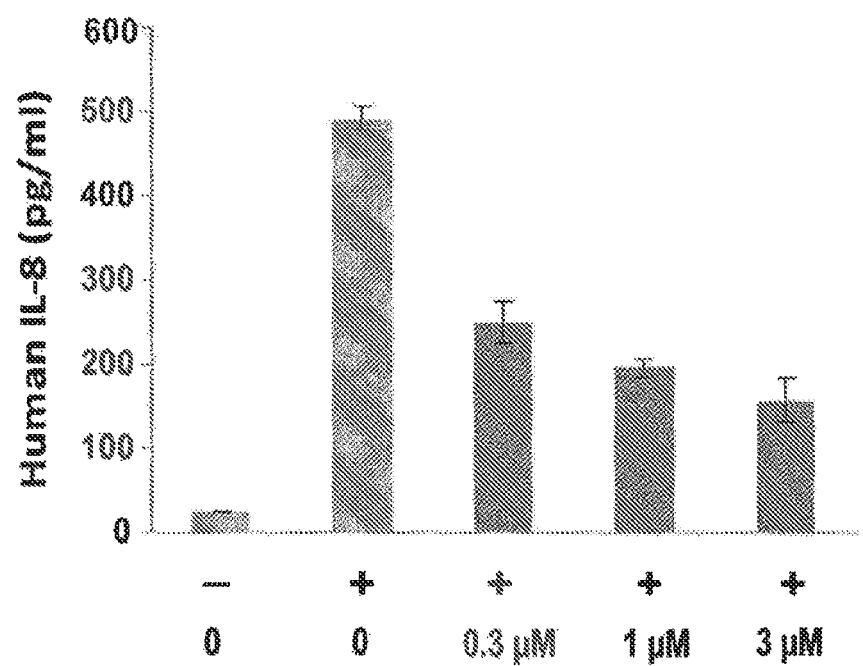
FIG. 11 presents a bar graph depicting IL-8 levels (pg/mL) demonstrating a dose dependent inhibition of PGN-TLR2-induced IL-8 release with compound K, determined using Normal Human Epidermal Keratinocyte (NHEK) cell cultures.

The activation of Toll-like receptor 2 (TLR2) by peptidoglycans (PGN), a common class of bacterial endotoxin, induces the release of proinflammatory cytokines that are necessary to mediate key immune and inflammatory responses (Lin et al., *Int Immunopharmacol*, 2010, 10, 883-891). The present example demonstrates that certain described isoprenyl compounds inhibit TLR2 inflammatory signaling pathways resulting in reduction of proinflammatory cytokine release, for example of IL-8. Briefly, normal primary adult human keratinocytes (NHEKs) were obtained from pooled donors and purchased from Cascade Biologics (Gibco; Carlsbad, Calif.) or ScienCell Research Labs (Carlsbad, Calif.). Cell treatments were performed only in the second and third passage in 96-well plates seeded with $5\text{-}10 \times 10^3$ cells per well. NHEK cells were cultured in keratinocyte growth medium (KGM; Gibco), in a serum-free environment, supplemented with EGF (10 ng/ml), hydrocortisone (1 µg/ml), bovine insulin (5 µg/ml) and human pituitary gland extract (2 mL) at 37° C. with 5% $CO_2$. To avoid any possible immunomodulating effects of these agents during agonist/antagonist treatments, cells were kept in KGM supplemented without EGF or hydrocortisone (depleted medium) 24 hours before treatments. The day of treatment, cells were pre-incubated with described isoprenyl compounds (0.1-100 µM; 1% v/v ethanol) in fresh depleted media in triplicates. After pre-incubation, cells were treated with PGN (10 g/ml) in DMSO for 24 hours at 37° C. Later, supernatants were harvested and stored in −80° C. and cells were subjected to viability tests by the MTT assay (Promega; Madison, Wis.). IL-8 levels (pg/mL), obtained with Compound K using the PGN-TLR2-induced inflammation model in NHEK cells are depicted in FIG. 11.

Example 21

ATPγS-Purinergic Receptor-Induced Inflammation Model in HMEC-1 Cells—Inhibition of Cytokine Levels Bacterial challenges, particularly on the epithelial surfaces, have been show to trigger the release of extracellular signaling nucleotide molecules, such as ATP. ATP, serving as an extra-cellular signaling molecule, is known to activate purinergic P2 receptors which are expressed on a variety of cells involved in immune and inflammatory responses, including macro- and microvascular endothelial cells (ECs). During the pathophysiology of such epithelial-related disorders, dermal microvascular ECs recruit inflammatory cells, including leukocytes, to the sites of bacterial challenge, such as on the skin, triggered, in part, by the release of proinflammatory mediators, such as IL-6, IL-8, Groα and MCP-1 (Swerlick et al., *J Invest Dermatol*, 1993, 100: 111S-115S). It has been previously demonstrated that the non-hydrolyzable analog of ATP, i.e., ATPγS induces the production of proinflammatory cytokines in human dermal microcascular endothelial cells through the modulation of the P2 purinergic receptor signaling (Seiffert et al., *J Invest Dermatol*, 2006, 126: 1017-27).

Figure 12:
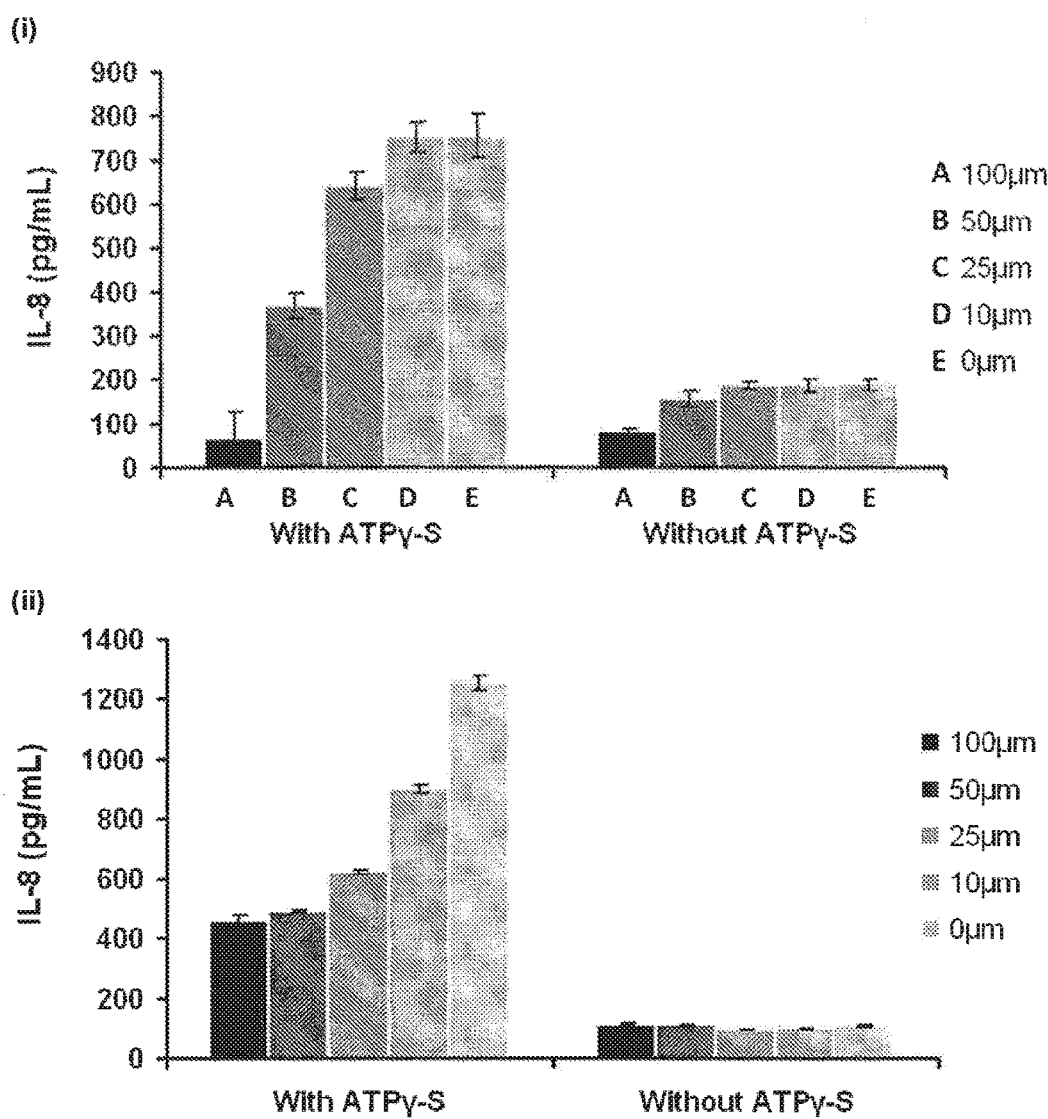
FIG. 12 presents bar graphs depicting IL-8 levels (pg/mL) obtained for AFC (Panel (i)) and Compound A (Panel (ii)) in the presence (panel A) and absence (panel B) of ATP-γS, demonstrating a dose dependent inhibition of ATP-γS-purinergic receptor-induced IL-8 release, determined using human microvascular endothelial cell line-1 (HMEC-1) cultures.
Figure 13:
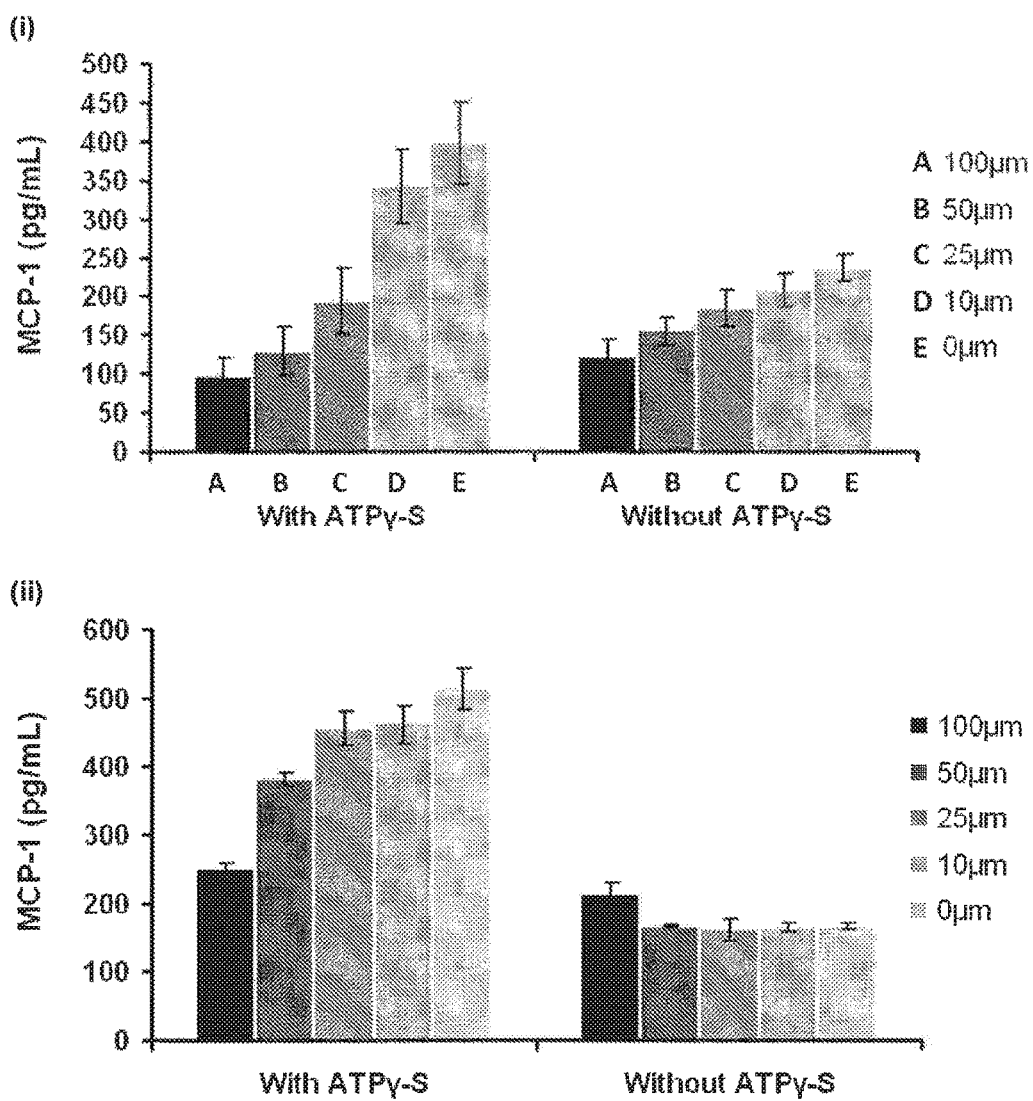
FIG. 13 presents bar graphs depicting MCP-1 levels (pg/mL) obtained for AFC (Panel (i)) and Compound A (Panel (ii)) in the presence (panel A) and absence (panel B) of ATP-γS, demonstrating a dose dependent inhibition of ATP-γS-purinergic receptor-induced MCP-1 release, determined using human microvascular endothelial cell line-1 (HMEC-1) cultures.
Figure 14:
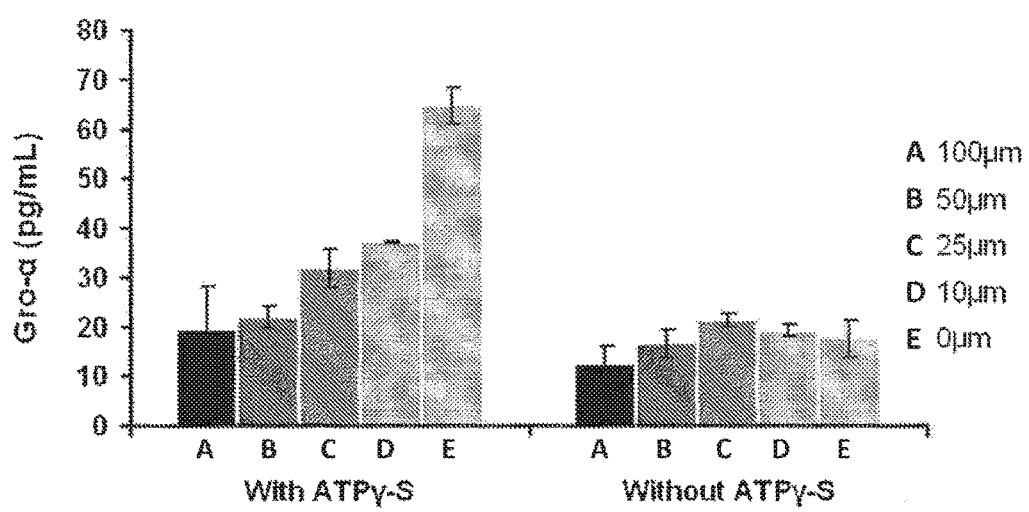
FIG. 14 presents bar graphs depicting Groα levels (pg/mL) obtained for AFC in the presence (panel A) and absence (panel B) of ATP-γS, demonstrating a dose dependent inhibition of ATP-γS-purinergic receptor-induced Groα release, determined using human microvascular endothelial cell line-1 (HMEC-1) cultures.

The protocol for inducing the production of proinflammatory cytokines in human microvascular endothelial cells (HMECs) with ATPγS, as previously described, serves as a cell-based model for studying the anti-inflammatory activities of test compounds. Using this cell-based model, the present example demonstrates that certain described isoprenyl compounds exhibit anti-inflammatory activity, as evidenced by the inhibition of ATPγS-induced-purinergic receptor-mediated release of proinflammatory mediators such as IL-8 and MCP-1. Briefly, HMECs were cultured in EC basal medium (EBM; Cambrex, Walkersville, Md.), supplemented with 0.5% fetal bovine serum (FBS), epidermal growth factor (EGF) (10 ng/mL) hydrocortisone (1 µg/mL) and 100 U/mL penicillin/100 µg/mL streptomycin at 37° C. with 5% $CO_2$ (referred to as supplemented media). In order to avoid possible immunomodulating effects of these agents during agonist/antagonist treatments, for some periods, cells were kept in EBM supplemented only with 0.5% FBS and penicillin/streptomycin without EGF or hydrocortisone (referred to as depleted media). Cells were plated at a concentration of $0.25 \times 10^6$ cells/well in supplemented media in 12-well plates. After cells are allowed to adhere (6-8 hours), media is changed to depleted media. After 24 hours, depleted media was removed and fresh depleted media containing various concentrations of Compound A in triplicate was added to the appropriate wells. Two hours later, to induce a pro-inflammatory response, ATPγS was added (100 µM) in separate wells (in triplicate) (Bender et al., Exp Dermatol, 2008, 17: 752-60; and Seiffert et al., J Invest Dermatol, 2006, 126: 1017-27). Cell cultures were examined for viability by Trypan blue exclusion and the reduction of 3-(4,5-dimethylthiazol-2-yl)-5-(3-carboxymethoxyphenyl)-2-(4-sulfophenyl)-2H-tetrazolium (MTS assay; Promega, Madison, Wis.) to determine the percentage of viable cells of various treatment concentrations of Compound A. After 6 hours of incubation, supernatants were harvested and assayed by enzyme-linked immunosorbent assays (ELISA) for the stimulated release of MCP-1, and IL-8 using appropriate protein standards (BD Pharmigen). IL-8 levels (pg/mL), obtained with AFC (panel (i)) and Compound A (panel (ii)) using an ATPγS-purinergic Receptor-induced Inflammation model in HMEC-1 cells are depicted in FIG. 12. MCP-1 levels (pg/mL), obtained with AFC (panel (i)) and Compound A (panel (ii)) using an ATPγS-purinergic Receptor-induced Inflammation model in HMEC-1 cells are depicted in FIG. 13. Groα levels (pg/mL), obtained with AFC using an ATPγS-purinergic Receptor-induced Inflammation model in HMEC-1 cells are depicted in FIG. 14.

Example 22

TPA-Induced Inflammation Model in NHEK Cells—Inhibition of Cytokine Levels

Figure 15:
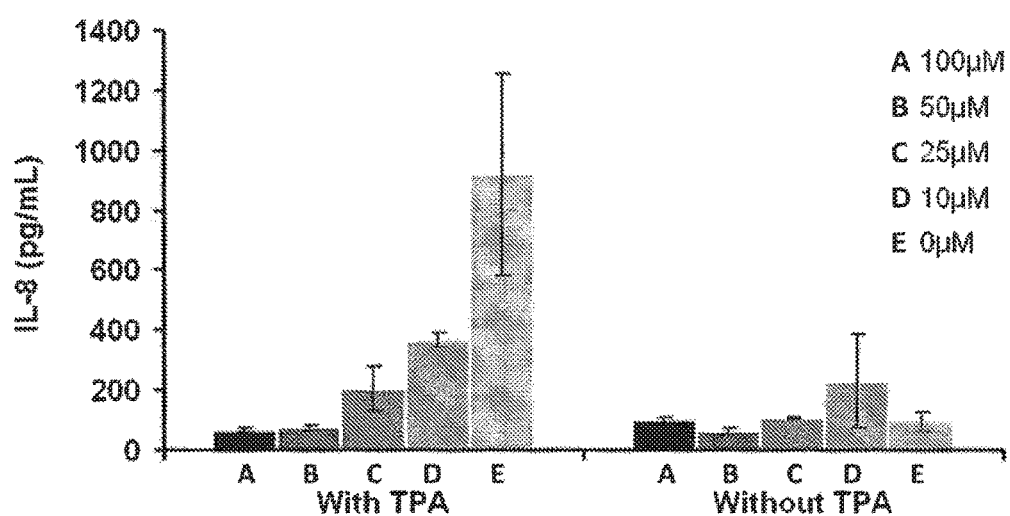
FIG. 15 is a bar graph depicting IL-8 levels (pg/mL) obtained for Compound A, demonstrating a dose dependent inhibition of TPA-induced IL-8 release, as determined using Normal Human Epidermal Keratinocyte (NHEK) cell cultures.

The present example demonstrates that certain described isoprenyl compounds of the present invention exhibit anti-inflammatory activity, as evidenced by the inhibition of TPA-induced release of proinflammatory mediators such as IL-8, in a human keratinocyte cell line (NHEK), similar to the effect on TPA-induced in vivo mouse ear model of inflammation. NHEK cells were cultured in keratinocyte growth medium (KGM; Gibco, Carlsbad, Calif.), in a serum-free environment, supplemented with EGF (10 ng/mL), hydrocortisone (1 µg/mL), bovine insulin (5 µg/mL) and human pituitary gland extract (2 mL) at 37° C. with 5% $CO_2$. To avoid any possible modulating effects of these agents during agonist/antagonist treatments, cells were kept in KGM supplemented without EGF or hydrocortisone (depleted medium). Cells were plated at a concentration of $0.25 \times 10^6$ cells/mL in 12 well plates in supplemented media. After the cells were allowed to adhere (6-8 hours), media will was changed to depleted media. After 24 hours, the depleted media was removed and fresh depleted media containing various concentrations of Compound A in triplicate was added to appropriate wells. After 8 hours, the media was changed to media without Compound A. After 16 hours, cell viability was determined by Trypan blue exclusion and MTS assay to determine the percent viability of various treatment concentrations of Compound A. Cells were cultured in TPA (5 ng/mL) to induce a pro-inflammatory response and release of IL-8. After 5 hours of incubation, supernatants were harvested and assayed by ELISA for the stimulated release of IL-8. Various concentrations of Compound A were added to tissue culture wells in triplicate 2 hours before addition of TPA as well as cells not exposed to TPA. Cell viability was determined by Trypan blue exclusion and MTS assay 16 hours after stimulation in a duplicate experiment where cells were washed and fresh media added without TPA or Compound A at the end of the stimulation period. IL-8 levels (pg/mL), obtained with Compound A using an TPA-induced inflammation model in NHEK cells are depicted in FIG. 15.

Example 23

Figure 16:
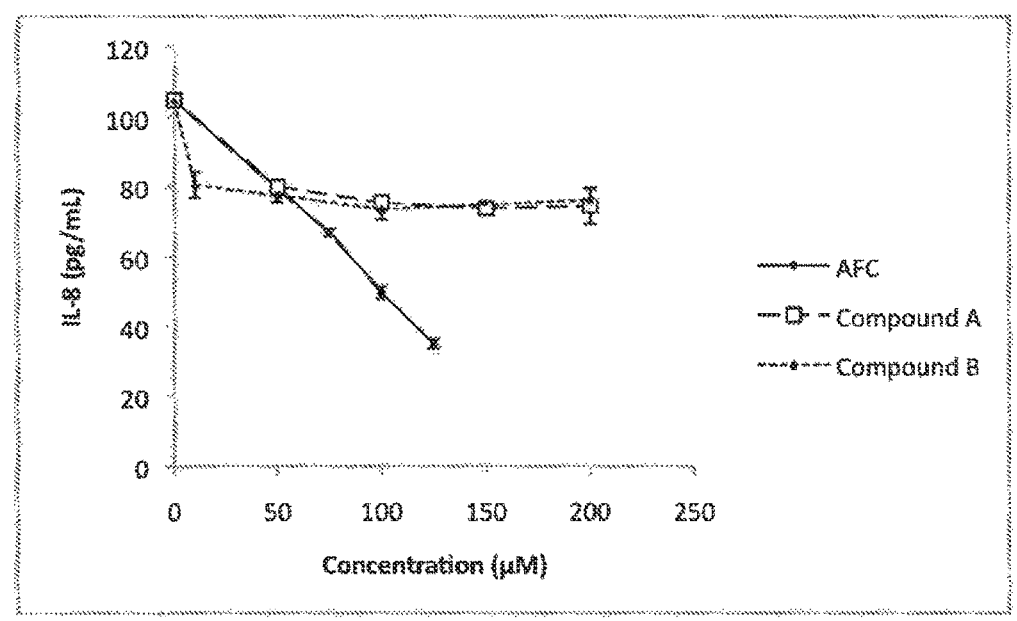
FIG. 16 is a graph depicting IL-8 levels (pg/mL) obtained for AFC, Compound A and Compound B, demonstrating a dose dependent inhibition of TNF-alpha induced IL-8 release, as determined using Human Umbilical Vein Endothelial cell (HUVEC) cultures.

TNFα-Induced Inflammation Model in HUVEC Cells—Inhibition of TNFα-Induced Cytokine Release TNF-α is a plieotropic cytokine with proinflammatory and immunomodulatory functions. The pathogenic role of TNF-α in inflammation is mediated through the interaction of TNF-α with TNF receptors that in turn result in induction of proinflammatory cytokines, such as TNF-α (itself), IL-8 and others. The present example demonstrates that certain described isoprenyl compounds of the present invention exhibit anti-inflammatory activity, as evidenced by the reduction of proinflammatory cytokines such as IL-8, mediated through TNF receptor mediated signaling in human umbilical vein endothelial cells (HUVECs). Breifly, HUVEC cells were cultured in endothelial growth medium-2 (EGM-2; Lonza; Walkersville, Md.), in a low serum environment (2% FBS), and supplemented with EGM-2 Bullet Kit (Lonza) at 37° C. with 5% $CO_2$. To avoid any possible modulating effects of these agents during agonist/antagonist treatments, cells were kept in EGM-2 supplemented without serum or growth factors (depleted medium). Cells were plated at a concentration of $1 \times 10^5$ cells/mL in 96-well plates in supplemented media. After the cells were allowed to adhere (6-8 hours), media will was changed to depleted media. Twenty-four hours later, media was removed and fresh depleted media containing various concentrations of AFC, Compound A and Compound B in triplicate was added to appropriate wells. After 30 minutes of pre-incubation, cells were stimulated with recombinant Human TNF-α ($1 \times 10^4$ U/mL; Millipore, Billerica, Mass.) to induce a pro-inflammatory response and release of IL-8. After 4 hours of incubation, supernatants were harvested and assayed by ELISA for the stimulated release of IL-8. Cell viability was determined by Trypan blue exclusion and MTS assay to determine the percent viability of various treatment concentrations of AFC, Compound A and Compound B. IL-8 levels (pg/mL), obtained with AFC, Compound A and Compound B using TNF-α-induced inflammation model in HUVEC cells are depicted in FIG. 16.

Example 24

Human Acne Study

A double-blind vehicle-controlled study in the treatment of mild to moderate facial acne is conducted for 12 weeks to demonstrate the efficacy and tolerability of described isoprenyl compounds in subjects with mild to moderate facial acne. 50 Female and male subjects 18+ years with mild to moderate acne are enrolled in this 12-week double-blind vehicle controlled study to demonstrate the efficacy and tolerability of described isoprenyl compounds in vehicle in subjects with mild to moderate facial acne characterized by erythema and inflammatory papules. 25 Subjects use a test compound in the vehicle to their entire face and the remaining 25 subjects use a vehicle control. Subjects are randomized between the two groups, which are balanced for age and severity of acne. Investigator evaluations, subject evaluations, photography, and dermospectrophotometer readings are taken at baseline, week 2, week 4, week 8, and week 12. Dermospectrophotometer readings are taken from each malar eminence. Subjects complete a Dermatology Life Quality Index and Visual Analog Scale evaluation at baseline and week 12. Subjects are evaluated at the following time points: Baseline, Week 2, Week 4, Week 8, Week 12. The baseline visit occur following a 2-week washout to ensure that subjects are not experiencing an acne flare.

EQUIVALENTS

Those skilled in the art will recognize, or be able to ascertain using no more than routine experimentation, that while the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., some embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any targeting moiety, any disease, disorder, and/or condition, any method of administration, any therapeutic application, etc.) can be excluded from any one or more claims, for any reason, whether or not related to the existence of prior art.

Publications discussed above and throughout the text are described solely for their disclosure prior to the filing date of the present application. Nothing herein is to be construed as an admission that the inventors are not entitled to antedate such disclosure by virtue of prior disclosure.

Thus, although the invention has been described in detail with particular reference to these embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference.

We claim:

1. A method of treating or ameliorating the symptoms of acne comprising steps of: administering to a subject in need thereof an effective amount of a compound selected from the group consisting of:

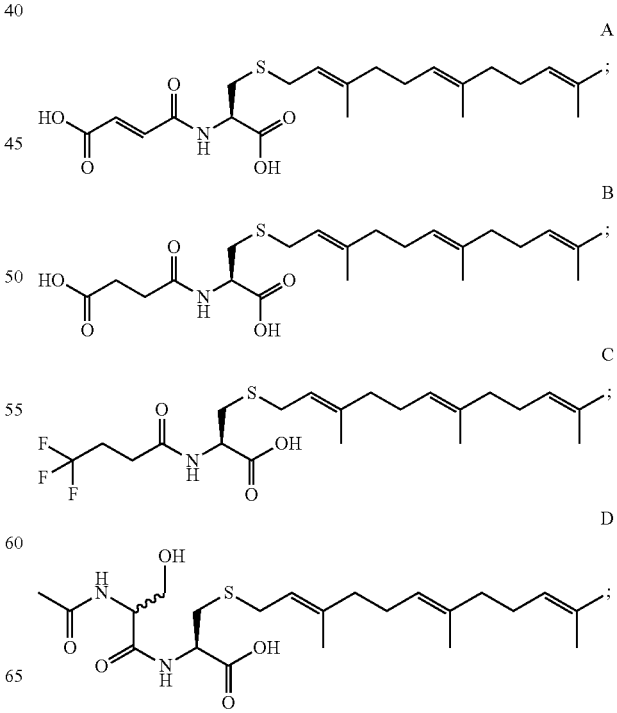

-continued

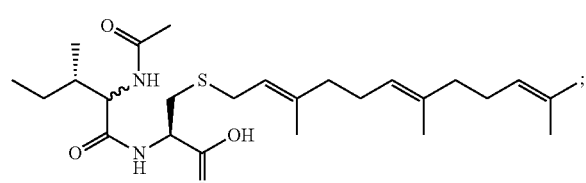
E

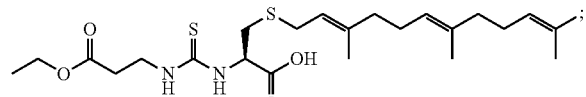
F

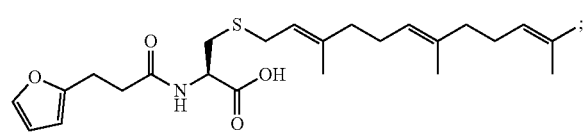
G

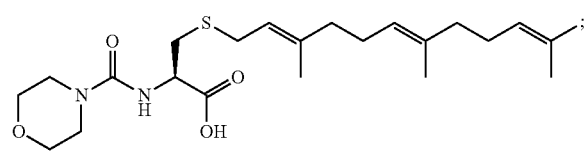
H

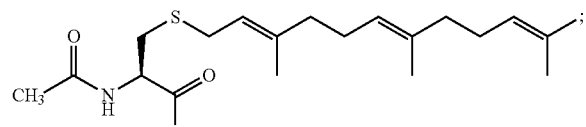
I

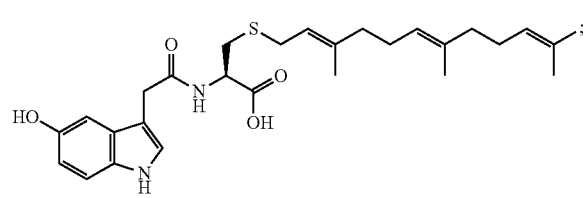
J

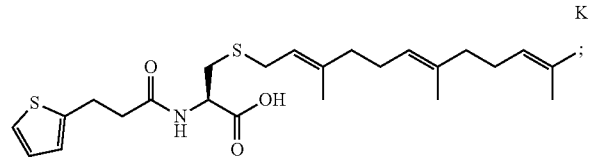
K

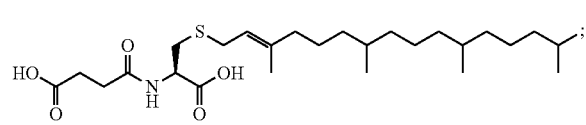
L and pharmaceutically acceptable salts of each of the foregoing.

2. The method according to claim 1, wherein the compound exhibits an anti-inflammatory activity and an antibacterial activity.

3. The method according to claim 1, wherein administration is topical.

4. The method according to claim 1, wherein administration is by inhalation.

5. The method according to claim 1, wherein administration is parenteral.

6. The method according to claim 1, wherein the compound is:

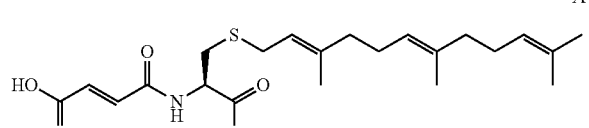
A or a pharmaceutically acceptable salt thereof.

7. The method according to claim 1, wherein the compound is:

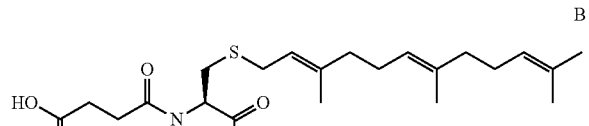
B or a pharmaceutically acceptable salt thereof.

8. The method according to claim 1, wherein the compound is:

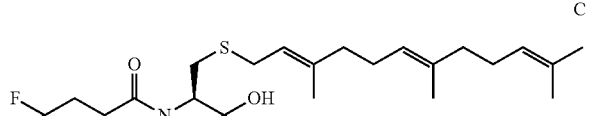
C or a pharmaceutically acceptable salt thereof.

9. The method of claim 1, wherein the compound is:

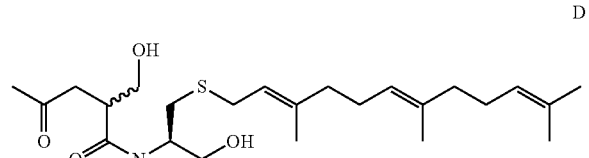
D or a pharmaceutically acceptable salt thereof.

10. The method of claim 1, wherein the compound is:

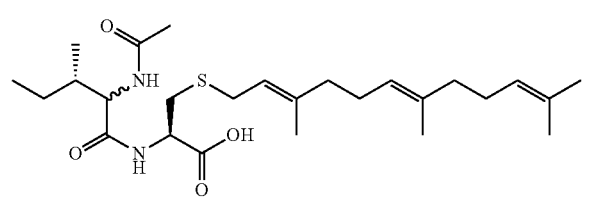
E or a pharmaceutically acceptable salt thereof.

11. The method of claim 1, wherein the compound is:

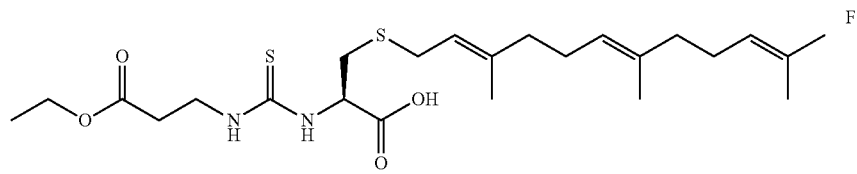 [SMILES: CCOC(=O)CCNC(=S)N[C@@H](CSC/C=C(\C)CC/C=C(\C)CCC=C(C)C)C(=O)O]

or a pharmaceutically acceptable salt thereof.

12. The method of claim 1, wherein the compound is:

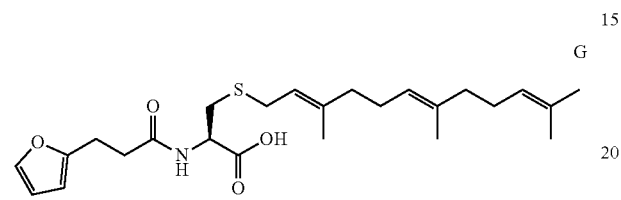

or a pharmaceutically acceptable salt thereof.

13. The method of claim 1, wherein the compound is:

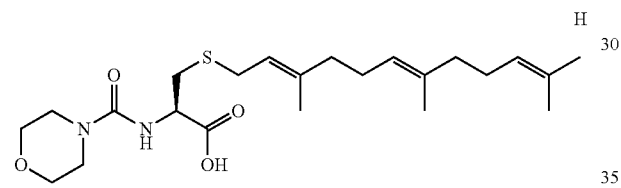

or a pharmaceutically acceptable salt thereof.

14. The method of claim 1, wherein the compound is:

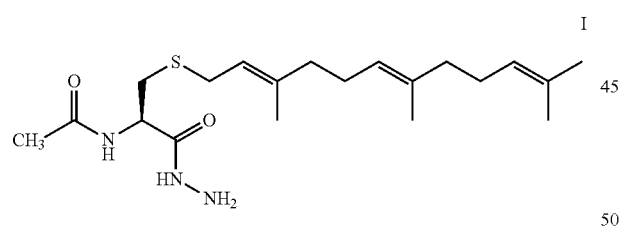

or a pharmaceutically acceptable salt thereof.

15. The method of claim 1, wherein the compound is:

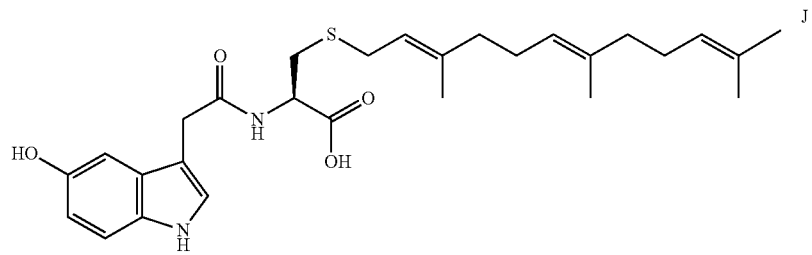 [SMILES: CC(C)=CCC/C(C)=C/CC/C(C)=C/CSC[C@H](NC(=O)Cc1c[nH]c2ccc(O)cc12)C(=O)O]

or a pharmaceutically acceptable salt thereof.

16. The method of claim 1, wherein the compound is:
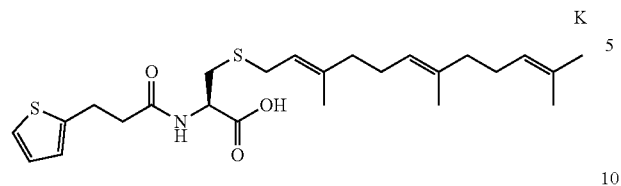
or a pharmaceutically acceptable salt thereof.
17. The method of claim 1, wherein the compound is:
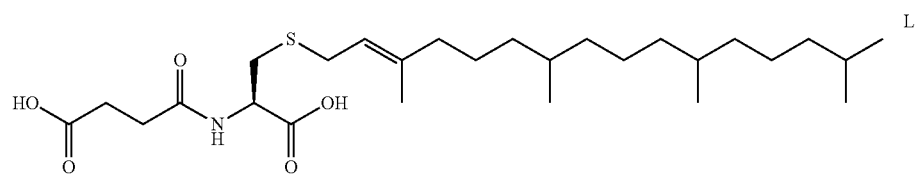 [SMILES: C/C(=C\CSC[C@H](NC(=O)CCC(=O)O)C(=O)O)CCCC(C)CCCC(C)CCCC(C)C]
or a pharmaceutically acceptable salt thereof.
* * * * *